United States Patent
Hayday et al.

(10) Patent No.: US 10,081,676 B2
(45) Date of Patent: Sep. 25, 2018

(54) HUMAN ANTI-IL-32 ANTIBODIES AND METHODS OF MAKING AND USING THE SAME

(71) Applicant: IMMUNOQURE AG, Dusseldorf (DE)

(72) Inventors: Adrian Hayday, Orpington (GB); Kai Kisand, Tartu (EE); Kai Krohn, Salmentaka (FI); Annalisa Macagno, Schlieren (CH); Shimobi Onuoha, Bishop's Stortford (GB); Paert Peterson, Tallinn (EE); Mike Rothe, Krailling (DE); Martin Woodward, London (GB); Syeda F. Y. Haque, London (GB)

(73) Assignee: ImmunoQure AG, Dusseldorf (DE)

( * ) Notice: Subject to any disclaimer, the term of this patent is extended or adjusted under 35 U.S.C. 154(b) by 0 days.

(21) Appl. No.: 14/902,394

(22) PCT Filed: Jul. 3, 2014

(86) PCT No.: PCT/EP2014/064163
§ 371 (c)(1),
(2) Date: Dec. 31, 2015

(87) PCT Pub. No.: WO2015/001010
PCT Pub. Date: Jan. 8, 2015

(65) Prior Publication Data
US 2016/0368981 A1 Dec. 22, 2016

(30) Foreign Application Priority Data
Jul. 3, 2013 (EP) .................................... 13174937

(51) Int. Cl.
*A61K 39/395* (2006.01)
*C12N 15/09* (2006.01)
*C07K 16/24* (2006.01)
*G01N 33/68* (2006.01)
*A61K 39/00* (2006.01)

(52) U.S. Cl.
CPC ....... *C07K 16/244* (2013.01); *G01N 33/6869* (2013.01); *A61K 2039/505* (2013.01); *A61K 2039/57* (2013.01); *C07K 2317/21* (2013.01); *C07K 2317/76* (2013.01); *C07K 2317/92* (2013.01); *G01N 2800/52* (2013.01); *G01N 2800/7095* (2013.01)

(58) Field of Classification Search
None
See application file for complete search history.

(56) References Cited

U.S. PATENT DOCUMENTS 6,309,636 B1 * 10/2001 do Couto ........... A61K 51/1051
424/133.1
2008/0219995 A1 9/2008 Kim et al.

FOREIGN PATENT DOCUMENTS

| JP | 2013-515477 | 5/2013 |
|---|---|---|
| WO | WO 2005/047478 A2 | 5/2005 |
| WO | WO 2013/098419 A1 | 7/2013 |

OTHER PUBLICATIONS

International Preliminary Report on Patentability for International Patent Application No. PCT/EP2014/064163, dated Jan. 14, 2016, 9 pages.
International Search Report and Written Opinion prepared by the European Patent Office dated Oct. 8, 2014, for International Application No. PCT/EP2014/064163.
Lee Siyoung et al: "Interleukin-32 Gamma Specific Monoclonal Antibody and Developing IL-32 Specific ELISA", Hybridoma, vol. 29, No. 6, Dec. 2010 (Dec. 2010), pp. 501-509, XPO=002716825.
Kim et al: "Interleukin-32 monoclonal antibodies for Immunohistochemistry, Western blotting, and ELISA", Journal of Immunological Methods, Elsevier Science Publishers B.V., Amsterdam, NL, vol. 333, No. 1-2, Jan. 28, 2008 (Jan. 28, 2008), pp. 38-50, XP022576406.
Shoda Hirofumi et al: "Interactions between IL-32 and tumor necrosis factor alpha contribute to the exacerbation of immune-inflammatory diseases", Arthritis Research and Therapy, Biomed Central, London, GB, vol. 8, No. 6, Nov. 1, 2006 (Nov. 1, 2006), p. R66, XP021026922.
Joosten Leo A B et al: "IL-32, a proinflammatory cytokine in rheumatoid arthritis", Proceedings of the National Academy of Sciences—PNAS,National Academy of Sciences, US, vol. 103, No. 9, Feb. 1, 2006 (Feb. 1, 2006), pp. 3298-3303, XP002716294.
Heinhuis et al. "Inflammation-dependent secretion and splicing of IL-32γ in rheumatoid arthritis," PNAS, Mar. 22, 2011, vol. 108, No. 12, pp. 4962-4967.

\* cited by examiner

*Primary Examiner* — Dong Jiang
(74) *Attorney, Agent, or Firm* — Sheridan Ross P.C.

(57) ABSTRACT

Provided are novel IL-32 binding molecules of human origin, particularly human anti-IL-32 antibodies as well as IL-32 binding fragments, derivatives and variants thereof. In addition, pharmaceutical compositions, kits and methods for use in diagnosis and therapy are described.

35 Claims, 18 Drawing Sheets

Specification includes a Sequence Listing.

A   2C2 (IgG3, variable heavy chain sequence VH) – SEQ ID NO: 2
```
FR1---------------------------CDR1----FR2----------CDR2-------------
QLRVQESGPGLLKPAETLSLTCSVSSGSVSNSRYYWAWIRQSPGKGLEWIGSMYYRGRSYYNPSLKS FR3------------------------------CDR3------FR4------
RLTISIDTSKNQFSLKLTSLTAADTAVYYCAAAVYHDLDYWGQGTLVTVSS
```

2C2 (variable lamda chain sequence VL) – SEQ ID NO: 4
```
FR1-------------------CDR1---------FR2------------CDR2---
QSVLTQPPSVSAAPGQKVTISCSGSGSSIGNNYVSWYQQLPGAAPKLLIYDNTKRPS FR3-------------------------------CDR3--------FR4-------
GIPDRFSGSKSGTSATLAITGLQPGDAADYYCGTWDSSFSVFWVFGGGTKLTVL
```

B   14B3 (IgG1, variable heavy chain sequence VH) – SEQ ID NO: 10
```
FR1----------------------------CDR1-FR2----------CDR2-------------
QVQLVESGGGVVQPGRSLRLSCVASGLTFRTYGMHWVRQAPGNGLEWVAIIWHDGNKKYYADSVKG FR3------------------------------CDR3---FR4--------
RFTISRDNSKNSLYLQMNSLRVEDTAVYYCAREMNGIDVWGQGTTVTVSS
```

14B3 (variable lambda chain sequence VL) – SEQ ID NO: 12
```
FR1-------------------CDR1-------FR2------------CDR2---
SYELTQPPSVSVSPGQTARITCSGDALPETYVYWYQQKSGQAPVKLIYEDSERPS FR3-----------------------------CDR3------FR4-------
GIPERFSGSSSGTLATLTISGAHVEDEADYYCYSTDSSGIGVFGGGTKLTVL
```

C   19A1 (IgG1, variable heavy chain sequence VH) – SEQ ID NO: 18
```
FR1----------------------------CDR1-FR2----------CDR2-------------
QVHLVESGGGVVQPGRSLRLSCVASGLTFRTYGMHWVRQAPGNGLEWVAIIWHDGNKKYYADSVKG FR3------------------------------CDR3---FR4--------
RFTISRDNSKNSLYLQMNSLRVEDTAVYYCAREMNGIDVWGQGTTVTVSS
```

19A1 (variable lambda chain sequence VL) – SEQ ID NO: 20
```
FR1-------------------CDR1-------FR2------------CDR2---
SYELTQPPSVSVSPGQTARITCSGDALPETYVYWYQQKSGQAPVKLIYEDSERPS FR3-----------------------------CDR3------FR4-------
GIPERFSGSSSGTLATLTISGAHVEDEADYYCYSTDSSGIGVFGGGTKLTVL
```

Fig. 1

D    26A6 (IgG1, variable heavy chain sequence VH) – SEQ ID NO: 26
```
FR1---------------------------CDR1-FR2-----------CDR2-------------
QVQLVESGGGVVQPGRSLRLSCVASGLTFRTYGMHWVRQAPGNGLEWVAIIWHDGNKKYFADSVKG

FR3-----------------------------CDR3---FR4--------
RFTISRDNSKNSLYLQMNSLRVEDTAVYYCAREMNGIDVWGQGTTVTVSS
```

26A6 (variable lambda chain sequence VL) – SEQ ID NO: 28
```
FR1------------------CDR1-------FR2------------CDR2---
SYELTQPPSVSVSPGQTARITCSGDALPETYVYWYQQKSGQAPVKLIYEDSERPS

FR3-------------------------------CDR3-------FR4-------
GIPERFSGSSSGTLATLTISGAHVEDEADYYCYSTDSSGIGVFGGGTKVTVL
```

Fig. 1 (continued)

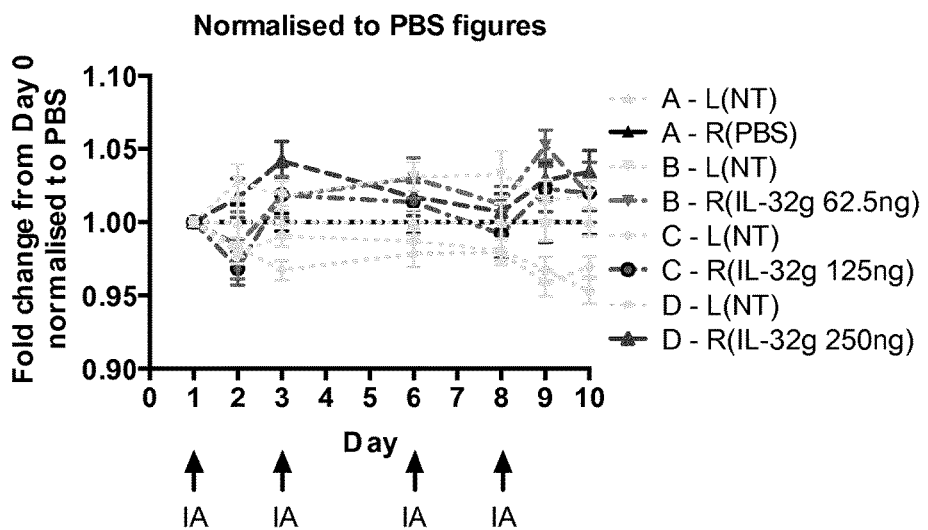
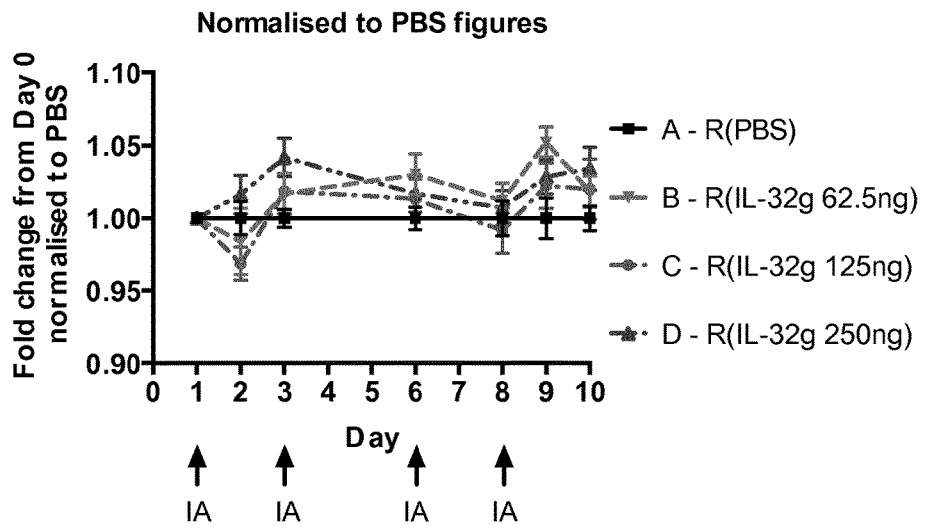
Fig. 11 (continued)

C
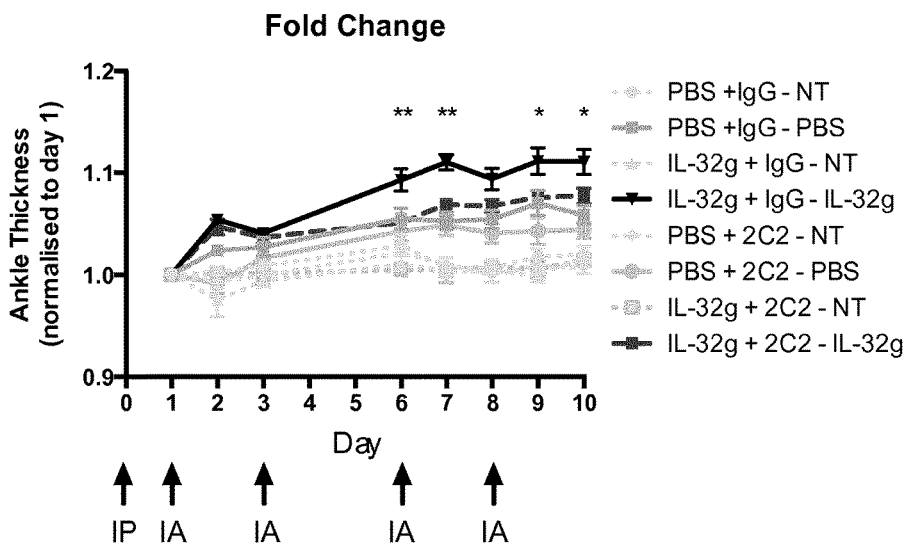
D
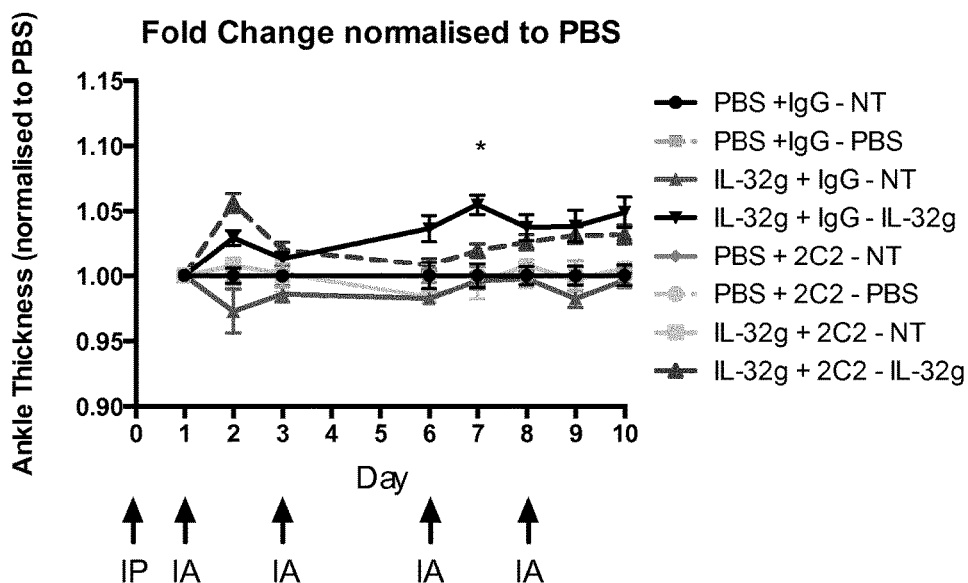
Fig. 12 (continued)

SEQUENCE LISTING

<160> NUMBER OF SEQ ID NOS: 30

<210> SEQ ID NO 1
<211> LENGTH: 354
<212> TYPE: DNA
<213> ORGANISM: Homo sapiens
<220> FEATURE:
<221> NAME/KEY: CDS
<222> LOCATION: (1)..(354)
<223> OTHER INFORMATION: 2C2-VH variable heavy chain (VH) sequence;
      2C2: IgG3, lambda
<220> FEATURE:
<221> NAME/KEY: V_region
<222> LOCATION: (91)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(321)
<223> OTHER INFORMATION: complementarity determining region (CDR)
      VH-CDR3

<400> SEQUENCE: 1

```
cag ctg cgg gtg cag gag tcg ggc cca gga ctg ttg aag cct gcg gag      48
Gln Leu Arg Val Gln Glu Ser Gly Pro Gly Leu Leu Lys Pro Ala Glu
1               5                  10                  15 acg ctg tcc ctc acc tgc agt gtc tct agt ggc tcc gtc agc aat agt      96
Thr Leu Ser Leu Thr Cys Ser Val Ser Ser Gly Ser Val Ser Asn Ser
            20                  25                  30 cgt tat tac tgg gcc tgg atc cgc cag tcc cca ggg aag gga ctg gag     144
Arg Tyr Tyr Trp Ala Trp Ile Arg Gln Ser Pro Gly Lys Gly Leu Glu
        35                  40                  45 tgg att ggg agt atg tat tat cgt ggg agg tcc tac tac aac ccg tcc     192
Trp Ile Gly Ser Met Tyr Tyr Arg Gly Arg Ser Tyr Tyr Asn Pro Ser
    50                  55                  60 ctc aag agt cgc ctc acc att tcg att gac acg tcc aag aat cag ttc     240
Leu Lys Ser Arg Leu Thr Ile Ser Ile Asp Thr Ser Lys Asn Gln Phe
65                  70                  75                  80 tcc ctg aaa ctg acc tct ctg acc gcc gca gac acg gcc gtc tat tat     288
Ser Leu Lys Leu Thr Ser Leu Thr Ala Ala Asp Thr Ala Val Tyr Tyr
                85                  90                  95 tgt gcc gca gtt tat cac gac ctt gac tac tgg ggc cag gga acc         336
Cys Ala Ala Val Tyr His Asp Leu Asp Tyr Trp Gly Gln Gly Thr
            100                 105                 110 ctg gtc acc gtc tcc tca                                             354
Leu Val Thr Val Ser Ser
        115
```

<210> SEQ ID NO 2
<211> LENGTH: 118
<212> TYPE: PRT
<213> ORGANISM: Homo sapiens

<400> SEQUENCE: 2

```
Gln Leu Arg Val Gln Glu Ser Gly Pro Gly Leu Leu Lys Pro Ala Glu
1               5                  10                  15

Thr Leu Ser Leu Thr Cys Ser Val Ser Ser Gly Ser Val Ser Asn Ser
            20                  25                  30

Arg Tyr Tyr Trp Ala Trp Ile Arg Gln Ser Pro Gly Lys Gly Leu Glu
        35                  40                  45
```

```
Trp Ile Gly Ser Met Tyr Tyr Arg Gly Arg Ser Tyr Tyr Asn Pro Ser
        50                  55                  60

Leu Lys Ser Arg Leu Thr Ile Ser Ile Asp Thr Ser Lys Asn Gln Phe
65                  70                  75                  80

Ser Leu Lys Leu Thr Ser Leu Thr Ala Ala Asp Thr Ala Val Tyr Tyr
                85                  90                  95

Cys Ala Ala Val Tyr His Asp Leu Asp Tyr Trp Gly Gln Gly Thr
                100                 105                 110

Leu Val Thr Val Ser Ser
        115
```

<210> SEQ ID NO 3
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: 2C2-VL variable light chain (VL) sequence,
      lambda type
<220> FEATURE:
<221> NAME/KEY: V_region
<222> LOCATION: (67)..(105)
<223> OTHER INFORMATION: complementarity determining region (CDR)
      VL-CDR1
<220> FEATURE:
<221> NAME/KEY: V_region
<222> LOCATION: (151)..(171)
<223> OTHER INFORMATION: complementarity determining region (CDR)
      VL-CDR2
<220> FEATURE:
<221> NAME/KEY: V_region
<222> LOCATION: (268)..(303)
<223> OTHER INFORMATION: complementarity determining region (CDR)
      VL-CDR3

<400> SEQUENCE: 3

```
cag tct gtg ttg acg cag ccg ccc tca gtg tct gcg gcc cca gga cag     48
Gln Ser Val Leu Thr Gln Pro Pro Ser Val Ser Ala Ala Pro Gly Gln
1               5                   10                  15 aag gtc acc atc tcc tgc tct gga agc ggc tcc agc att ggg aac aat     96
Lys Val Thr Ile Ser Cys Ser Gly Ser Gly Ser Ser Ile Gly Asn Asn
                20                  25                  30 tat gtc tcc tgg tac cag caa ctc cca gga gca gcc ccc aaa ctc ctc    144
Tyr Val Ser Trp Tyr Gln Gln Leu Pro Gly Ala Ala Pro Lys Leu Leu
            35                  40                  45 att tat gac aat act aag cga ccc tca ggg att cct gac cga ttc tct    192
Ile Tyr Asp Asn Thr Lys Arg Pro Ser Gly Ile Pro Asp Arg Phe Ser
        50                  55                  60 ggc tcc aag tct ggc acg tca gcc acc ctg gcc atc acc gga ctc caa    240
Gly Ser Lys Ser Gly Thr Ser Ala Thr Leu Ala Ile Thr Gly Leu Gln
65                  70                  75                  80 cct ggg gac gcg gcc gat tat tac tgc gga aca tgg gat agt agt ttc    288
Pro Gly Asp Ala Ala Asp Tyr Tyr Cys Gly Thr Trp Asp Ser Ser Phe
                85                  90                  95 agt gtt ttt tgg gta ttc ggc gga ggg acc aag ctg acc gtc cta         333
Ser Val Phe Trp Val Phe Gly Gly Gly Thr Lys Leu Thr Val Leu
                100                 105                 110
```

<210> SEQ ID NO 4
<211> LENGTH: 111
<212> TYPE: PRT
<213> ORGANISM: Homo sapiens

<400> SEQUENCE: 4

```
Gln Ser Val Leu Thr Gln Pro Pro Ser Val Ser Ala Ala Pro Gly Gln
1               5                   10                  15

Lys Val Thr Ile Ser Cys Ser Gly Ser Gly Ser Ile Gly Asn Asn
            20                  25                  30

Tyr Val Ser Trp Tyr Gln Gln Leu Pro Gly Ala Ala Pro Lys Leu Leu
            35                  40                  45

Ile Tyr Asp Asn Thr Lys Arg Pro Ser Gly Ile Pro Asp Arg Phe Ser
50                  55                  60

Gly Ser Lys Ser Gly Thr Ser Ala Thr Leu Ala Ile Thr Gly Leu Gln
65                  70                  75                  80

Pro Gly Asp Ala Ala Asp Tyr Tyr Cys Gly Thr Trp Asp Ser Ser Phe
                85                  90                  95

Ser Val Phe Trp Val Phe Gly Gly Gly Thr Lys Leu Thr Val Leu
            100                 105                 110
```

<210> SEQ ID NO 5
<211> LENGTH: 1134
<212> TYPE: DNA
<213> ORGANISM: Homo sapiens
<220> FEATURE:
<221> NAME/KEY: CDS
<222> LOCATION: (1)..(1134)
<223> OTHER INFORMATION: 2C2-CH constant heavy chain (CH) sequence

<400> SEQUENCE: 5

```
gct tcc acc aag ggc cca tcg gtc ttc ccc ctg gcg ccc tgc tcc agg      48
Ala Ser Thr Lys Gly Pro Ser Val Phe Pro Leu Ala Pro Cys Ser Arg
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac acc tgc aac gta aat cac aag ccc agc aac acc aag gtg gac aag     288
Tyr Thr Cys Asn Val Asn His Lys Pro Ser Asn Thr Lys Val Asp Lys
                85                  90                  95 aga gtt gag ctc aaa acc cca ctt ggt gac aca act cac aca tgc cca     336
Arg Val Glu Leu Lys Thr Pro Leu Gly Asp Thr Thr His Thr Cys Pro
            100                 105                 110 cgg tgc cca gag ccc aaa tct tgt gac aca cct ccc ccg tgc cca cgg     384
Arg Cys Pro Glu Pro Lys Ser Cys Asp Thr Pro Pro Pro Cys Pro Arg
        115                 120                 125 tgc cca gag ccc aaa tct tgt gac aca cct ccc cca tgc cca cgg tgc     432
Cys Pro Glu Pro Lys Ser Cys Asp Thr Pro Pro Pro Cys Pro Arg Cys
    130                 135                 140 cca gag ccc aaa tct tgt gac aca cct ccc ccg tgc cca agg tgc cca     480
Pro Glu Pro Lys Ser Cys Asp Thr Pro Pro Pro Cys Pro Arg Cys Pro
145                 150                 155                 160 gca cct gaa ctc ctg gga gga ccg tca gtc ttc ctc ttc ccc cca aaa     528
Ala Pro Glu Leu Leu Gly Gly Pro Ser Val Phe Leu Phe Pro Pro Lys
                165                 170                 175
```

| | | |
|---|---|---|
| ccc aag gat acc ctt atg att tcc cgg acc cct gag gtc acg tgc gtg<br>Pro Lys Asp Thr Leu Met Ile Ser Arg Thr Pro Glu Val Thr Cys Val<br>                180                      185                  190 | 576 |
| gtg gtg gac gtg agc cac gaa gac ccc gag gtc cag ttc aag tgg tac<br>Val Val Asp Val Ser His Glu Asp Pro Glu Val Gln Phe Lys Trp Tyr<br>       195                     200                      205 | 624 |
| gtg gac ggc gtg gag gtg cat aat gcc aag aca aag ctg cgg gag gag<br>Val Asp Gly Val Glu Val His Asn Ala Lys Thr Lys Leu Arg Glu Glu<br>210                      215                      220 | 672 |
| cag tac aac agc acg ttc cgt gtg gtc agc gtc ctc acc gtc ctg cac<br>Gln Tyr Asn Ser Thr Phe Arg Val Val Ser Val Leu Thr Val Leu His<br>225                      230                      235                240 | 720 |
| cag gac tgg ctg aac ggc aag gag tac aag tgc aag gtc tcc aac aaa<br>Gln Asp Trp Leu Asn Gly Lys Glu Tyr Lys Cys Lys Val Ser Asn Lys<br>                245                      250                      255 | 768 |
| gcc ctc cca gcc ccc atc gag aaa acc atc tcc aaa acc aaa gga cag<br>Ala Leu Pro Ala Pro Ile Glu Lys Thr Ile Ser Lys Thr Lys Gly Gln<br>                260                      265                      270 | 816 |
| ccc cga gaa cca cag gtg tac acc ctg ccc cca tcc cgg gag gag atg<br>Pro Arg Glu Pro Gln Val Tyr Thr Leu Pro Pro Ser Arg Glu Glu Met<br>       275                     280                      285 | 864 |
| acc aag aac cag gtc agc ctg acc tgc ctg gtc aaa ggc ttc tac ccc<br>Thr Lys Asn Gln Val Ser Leu Thr Cys Leu Val Lys Gly Phe Tyr Pro<br>290                      295                      300 | 912 |
| agc gac atc gcc gtg gag tgg gag agc aat ggg cag ccg gag aac aac<br>Ser Asp Ile Ala Val Glu Trp Glu Ser Asn Gly Gln Pro Glu Asn Asn<br>305                      310                      315                320 | 960 |
| tac aac acc acg cct ccc atg ctg gac tcc gac ggc tcc ttc ttc ctc<br>Tyr Asn Thr Thr Pro Pro Met Leu Asp Ser Asp Gly Ser Phe Phe Leu<br>                325                      330                      335 | 1008 |
| tac agc aag ctc acc gtg gac aag agc agg tgg cag cag ggg aac atc<br>Tyr Ser Lys Leu Thr Val Asp Lys Ser Arg Trp Gln Gln Gly Asn Ile<br>                340                      345                      350 | 1056 |
| ttc tca tgc tcc gtg atg cat gag gct ctg cac aac cgc tac acg cag<br>Phe Ser Cys Ser Val Met His Glu Ala Leu His Asn Arg Tyr Thr Gln<br>       355                     360                      365 | 1104 |
| aag agc ctc tcc ctg tct ccg ggt aaa tga<br>Lys Ser Leu Ser Leu Ser Pro Gly Lys<br>370                      375 | 1134 |

<210> SEQ ID NO 6
<211> LENGTH: 377
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1                    5                      10                      15

Ser Thr Ser Gly Gly Thr Ala Ala Leu Gly Cys Leu Val Lys Asp Tyr
                20                      25                      30

Phe Pro Glu Pro Val Thr Val Ser Trp Asn Ser Gly Ala Leu Thr Ser
                    35                      40                      45

Gly Val His Thr Phe Pro Ala Val Leu Gln Ser Ser Gly Leu Tyr Ser
50                      55                      60

Leu Ser Ser Val Val Thr Val Pro Ser Ser Ser Leu Gly Thr Gln Thr
65                    70                      75                      80

Tyr Thr Cys Asn Val Asn His Lys Pro Ser Asn Thr Lys Val Asp Lys
                    85                      90                      95

```
Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Tyr Thr Gln
        355                 360                 365

Lys Ser Leu Ser Leu Ser Pro Gly Lys
    370                 375

<210> SEQ ID NO 7
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 2C2-CL constant lambda chain (CL) sequence
<220> FEATURE:
<221> NAME/KEY: misc_feature
<222> LOCATION: (271)..(321)
<223> OTHER INFORMATION: not sequenced but obtained from database

<400> SEQUENCE: 7 agt cag ccc aag gct gcc ccc tcg gtc act ctg ttc ccg ccc tcc tct    48
Ser Gln Pro Lys Ala Ala Pro Ser Val Thr Leu Phe Pro Pro Ser Ser
1               5                   10                  15 gag gag ctt caa gcc aac aag gcc aca ctg gtg tgt ctc ata agt gac    96
Glu Glu Leu Gln Ala Asn Lys Ala Thr Leu Val Cys Leu Ile Ser Asp
            20                  25                  30
```

```
ttc tac ccg gga gcc gtg aca gtg gcc tgg aag gca gat agc agc ccc    144
Phe Tyr Pro Gly Ala Val Thr Val Ala Trp Lys Ala Asp Ser Ser Pro
        35                  40                  45 gtc aag gcg gga gtg gag acc acc aca ccc tcc aaa caa agc aac aac    192
Val Lys Ala Gly Val Glu Thr Thr Thr Pro Ser Lys Gln Ser Asn Asn
 50                  55                  60 aag tac gcg gcc agc agc tac ctg agc ctg acg cct gag cag tgg aag    240
Lys Tyr Ala Ala Ser Ser Tyr Leu Ser Leu Thr Pro Glu Gln Trp Lys
 65                  70                  75                  80 tcc cac aaa agc tac agc tgc cag gtc aca cat gaa ggg agc acc gtg    288
Ser His Lys Ser Tyr Ser Cys Gln Val Thr His Glu Gly Ser Thr Val
                 85                  90                  95 gag aag aca gtg gcc cct aca gaa tgt tca tag                        321
Glu Lys Thr Val Ala Pro Thr Glu Cys Ser
            100                 105
```

<210> SEQ ID NO 8
<211> LENGTH: 106
<212> TYPE: PRT
<213> ORGANISM: Homo sapiens

<400> SEQUENCE: 8

```
Ser Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                 85                  90                  95

Glu Lys Thr Val Ala Pro Thr Glu Cys Ser
             100                 105
```

<210> SEQ ID NO 9
<211> LENGTH: 348
<212> TYPE: DNA
<213> ORGANISM: Homo sapiens
<220> FEATURE:
<221> NAME/KEY: CDS
<222> LOCATION: (1)..(348)
<223> OTHER INFORMATION: 14B3-VH variable heavy chain (VH) sequence;
      14B3: IgG1, lambda
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(315)
<223> OTHER INFORMATION: complementarity determining region (CDR)
      VH-CDR3

-continued

```
<400> SEQUENCE: 9 cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gta gcg tct gga ctc act ttc agg acc tat      96
Ser Leu Arg Leu Ser Cys Val Ala Ser Gly Leu Thr Phe Arg Thr Tyr
            20                  25                  30 ggc atg cac tgg gtc cgc cag gct cca ggc aac ggg ctg gag tgg gtg     144
Gly Met His Trp Val Arg Gln Ala Pro Gly Asn Gly Leu Glu Trp Val
        35                  40                  45 gca atc ata tgg cat gat ggt aat aaa aaa tac tat gca gac tcc gta     192
Ala Ile Ile Trp His Asp Gly Asn Lys Lys Tyr Tyr Ala Asp Ser Val
    50                  55                  60 aag ggc cga ttc acc atc tcc agg gac aat tcc aag aac agt cta tat     240
Lys Gly Arg Phe Thr Ile Ser Arg Asp Asn Ser Lys Asn Ser Leu Tyr
65                  70                  75                  80 ctc caa atg aac agc ctg aga gtc gag gac acg gct gtg tat tac tgt     288
Leu Gln Met Asn Ser Leu Arg Val Glu Asp Thr Ala Val Tyr Tyr Cys
                85                  90                  95 gcg aga gaa atg aat ggc atc gac gtc tgg ggc caa ggg acc acg gtc     336
Ala Arg Glu Met Asn Gly Ile Asp Val Trp Gly Gln Gly Thr Thr Val
            100                 105                 110 acc gtc tcc tca                                                     348
Thr Val Ser Ser
        115

<210> SEQ ID NO 10
<211> LENGTH: 116
<212> TYPE: PRT
<213> ORGANISM: Homo sapiens

<400> SEQUENCE: 10

Gln Val Gln Leu Val Glu Ser Gly Gly Gly Val Val Gln Pro Gly Arg
1               5                   10                  15

Ser Leu Arg Leu Ser Cys Val Ala Ser Gly Leu Thr Phe Arg Thr Tyr
            20                  25                  30

Gly Met His Trp Val Arg Gln Ala Pro Gly Asn Gly Leu Glu Trp Val
        35                  40                  45

Ala Ile Ile Trp His Asp Gly Asn Lys Lys Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Glu Met Asn Gly Ile Asp Val Trp Gly Gln Gly Thr Thr Val
            100                 105                 110

Thr Val Ser Ser
        115

<210> SEQ ID NO 11
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 14B3-VL variable light chain (VL) sequence,
      lambda type
```

```
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(291)
<223> OTHER INFORMATION: complementarity determining region (CDR)
      VL-CDR3

<400> SEQUENCE: 11 tcc tat gag ctg acc cag cca ccc tcg gtg tca gtg tcc cca gga caa      48
Ser Tyr Glu Leu Thr Gln Pro Pro Ser Val Ser Val Ser Pro Gly Gln
1               5                   10                  15 acg gcc agg atc acc tgc tct gga gat gcg ttg cca gaa aca tat gtt      96
Thr Ala Arg Ile Thr Cys Ser Gly Asp Ala Leu Pro Glu Thr Tyr Val
                20                  25                  30 tat tgg tac cag cag aag tca ggc cag gcc cct gtg aag ctc atc tat    144
Tyr Trp Tyr Gln Gln Lys Ser Gly Gln Ala Pro Val Lys Leu Ile Tyr
            35                  40                  45 gag gac agc gaa cga ccc tcc ggg atc cct gag aga ttc tct ggc tcc    192
Glu Asp Ser Glu Arg Pro Ser Gly Ile Pro Glu Arg Phe Ser Gly Ser
50                  55                  60 agc tca ggg aca ttg gcc acc ttg act atc agt ggg gcc cat gtg gag    240
Ser Ser Gly Thr Leu Ala Thr Leu Thr Ile Ser Gly Ala His Val Glu
65                  70                  75                  80 gat gaa gct gac tac tac tgt tac tca aca gac agt agt ggt atc ggg    288
Asp Glu Ala Asp Tyr Tyr Cys Tyr Ser Thr Asp Ser Ser Gly Ile Gly
                85                  90                  95 gtg ttc gga gga ggg acc aag ctg acc gtc cta                        321
Val Phe Gly Gly Gly Thr Lys Leu Thr Val Leu
                100                 105

<210> SEQ ID NO 12
<211> LENGTH: 107
<212> TYPE: PRT
<213> ORGANISM: Homo sapiens

<400> SEQUENCE: 12

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Glu Thr Tyr Val
                20                  25                  30

Tyr Trp Tyr Gln Gln Lys Ser Gly Gln Ala Pro Val Lys Leu Ile Tyr
            35                  40                  45

Glu Asp Ser Glu Arg Pro Ser Gly Ile Pro Glu Arg Phe Ser Gly Ser
50                  55                  60

Ser Ser Gly Thr Leu Ala Thr Leu Thr Ile Ser Gly Ala His Val Glu
65                  70                  75                  80

Asp Glu Ala Asp Tyr Tyr Cys Tyr Ser Thr Asp Ser Ser Gly Ile Gly
                85                  90                  95

Val Phe Gly Gly Gly Thr Lys Leu Thr Val Leu
                100                 105
```

<210> SEQ ID NO 13
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 14B3-CH constant heavy chain (CH) sequence

<400> SEQUENCE: 13

```
gcc tcc acc aag ggc cca tcg gtc ttc ccc ctg gca ccc tcc tcc aag        48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc       240
Leu Ser Ser Val Val Thr Val Pro Ser Ser Leu Gly Thr Gln Thr
65                  70                  75                  80 tac atc tgc aac gtg aat cac aag ccc agc aac acc aag gtg gac aag       288
Tyr Ile Cys Asn Val Asn His Lys Pro Ser Asn Thr Lys Val Asp Lys
                85                  90                  95 aga gtt gag ccc aaa tct tgt gac aaa act cac aca tgc cca ccg tgc       336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca       384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc       432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg       480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag       528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg       576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac       624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg       672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gag gag       720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat       768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac       816
Pro Ser Asp Ile Ala Val Glu Trp Glu Ser Asn Gly Gln Pro Glu Asn
            260                 265                 270
```

|  |  |  |  |  |  |  |  |  |  |  | | |
|---|---|---|---|---|---|---|---|---|---|---|---|---|
| aac | tac | aag | acc | acg | cct | ccc | gtg | ctg | gac | tcc | gac ggc tcc ttc ttc | 864 |
| Asn | Tyr | Lys 275 | Thr | Thr | Pro | Pro 280 | Val | Leu | Asp | Ser | Asp Gly Ser Phe Phe 285 | |
| ctc | tat | agc | aag | ctc | acc | gtg | gac | aag | agc | agg | tgg cag cag ggg aac | 912 |
| Leu | Tyr | Ser 290 | Lys | Leu | Thr | Val 295 | Asp | Lys | Ser | Arg | Trp Gln Gln Gly Asn 300 | |
| gtc | ttc | tca | tgc | tcc | gtg | atg | cat | gag | gct | ctg | cac aac cac tac acg | 960 |
| Val | Phe 305 | Ser | Cys | Ser | Val 310 | Met | His | Glu | Ala | Leu 315 | His Asn His Tyr Thr 320 | |
| cag | aag | agc | ctc | tcc | ctg | tcc | ccg | ggt | aaa | tga | | 993 |
| Gln | Lys | Ser | Leu | Ser 325 | Leu | Ser | Pro | Gly | Lys 330 | | | |

<210> SEQ ID NO 14
<211> LENGTH: 330
<212> TYPE: PRT
<213> ORGANISM: Homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

```
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 14B3-CL constant lambda chain (CL) sequence
<220> FEATURE:
<221> NAME/KEY: misc_feature
<222> LOCATION: (271)..(321)
<223> OTHER INFORMATION: not sequenced but obtained from database

<400> SEQUENCE: 15 agt cag ccc aag gct gcc ccc tcg gtc act ctg ttc ccg ccc tcc tct      48
Ser Gln Pro Lys Ala Ala Pro Ser Val Thr Leu Phe Pro Pro Ser Ser
1               5                   10                  15 gag gag ctt caa gcc aac aag gcc aca ctg gtg tgt ctc ata agt gac      96
Glu Glu Leu Gln Ala Asn Lys Ala Thr Leu Val Cys Leu Ile Ser Asp
            20                  25                  30 ttc tac ccg gga gcc gtg aca gtg gcc tgg aag gca gat agc agc ccc     144
Phe Tyr Pro Gly Ala Val Thr Val Ala Trp Lys Ala Asp Ser Ser Pro
        35                  40                  45 gtc aag gcg gga gtg gag acc acc aca ccc tcc aaa caa agc aac aac     192
Val Lys Ala Gly Val Glu Thr Thr Thr Pro Ser Lys Gln Ser Asn Asn
50                  55                  60 aag tac gcg gcc agc agc tac ctg agc ctg acg cct gag cag tgg aag     240
Lys Tyr Ala Ala Ser Ser Tyr Leu Ser Leu Thr Pro Glu Gln Trp Lys
65                  70                  75                  80 tcc cac aaa agc tac agc tgc cag gtc aca cat gaa ggg agc acc gtg     288
Ser His Lys Ser Tyr Ser Cys Gln Val Thr His Glu Gly Ser Thr Val
                85                  90                  95 gag aag aca gtg gcc cct aca gaa tgt tca tag                         321
Glu Lys Thr Val Ala Pro Thr Glu Cys Ser
            100                 105

<210> SEQ ID NO 16
<211> LENGTH: 106
<212> TYPE: PRT
<213> ORGANISM: Homo sapiens

<400> SEQUENCE: 16

Ser Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80
```

```
Ser His Lys Ser Tyr Ser Cys Gln Val Thr His Glu Gly Ser Thr Val
            85                  90                  95

Glu Lys Thr Val Ala Pro Thr Glu Cys Ser
        100                 105

<210> SEQ ID NO 17
<211> LENGTH: 348
<212> TYPE: DNA
<213> ORGANISM: Homo sapiens
<220> FEATURE:
<221> NAME/KEY: CDS
<222> LOCATION: (1)..(348)
<223> OTHER INFORMATION: 19A1-VH variable heavy chain (VH) sequence;
      19A1: IgG1, lambda
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(315)
<223> OTHER INFORMATION: complementarity determining region (CDR)
      VH-CDR3

<400> SEQUENCE: 17 cag gtg cac ctg gtg gag tct ggg gga ggc gtg gtc cag cct ggg agg     48
Gln Val His Leu Val Glu Ser Gly Gly Gly Val Val Gln Pro Gly Arg
1               5                   10                  15 tcc ctg aga ctc tcc tgt gtc gcg tct gga ctc act ttc agg acc tat     96
Ser Leu Arg Leu Ser Cys Val Ala Ser Gly Leu Thr Phe Arg Thr Tyr
            20                  25                  30 ggc atg cac tgg gtc cgc cag gct cca ggc aac ggg ctg gag tgg gtg    144
Gly Met His Trp Val Arg Gln Ala Pro Gly Asn Gly Leu Glu Trp Val
        35                  40                  45 gca att ata tgg cat gat ggt aat aaa aaa tac tat gca gac tcc gta    192
Ala Ile Ile Trp His Asp Gly Asn Lys Lys Tyr Tyr Ala Asp Ser Val
    50                  55                  60 aag ggc cga ttc acc atc tcc agg gac aat tcc aag aac agt cta tat    240
Lys Gly Arg Phe Thr Ile Ser Arg Asp Asn Ser Lys Asn Ser Leu Tyr
65                  70                  75                  80 ctc caa atg aac agc ctg aga gtc gag gac acg gct gtg tat tac tgt    288
Leu Gln Met Asn Ser Leu Arg Val Glu Asp Thr Ala Val Tyr Tyr Cys
            85                  90                  95 gcg aga gaa atg aat ggc atc gac gtc tgg ggc caa ggg acc acg gtc    336
Ala Arg Glu Met Asn Gly Ile Asp Val Trp Gly Gln Gly Thr Thr Val
        100                 105                 110 acc gtc tcc tca                                                    348
Thr Val Ser Ser
        115

<210> SEQ ID NO 18
<211> LENGTH: 116
<212> TYPE: PRT
<213> ORGANISM: Homo sapiens

<400> SEQUENCE: 18

Gln Val His Leu Val Glu Ser Gly Gly Gly Val Val Gln Pro Gly Arg
1               5                   10                  15

Ser Leu Arg Leu Ser Cys Val Ala Ser Gly Leu Thr Phe Arg Thr Tyr
            20                  25                  30
```

```
Gly Met His Trp Val Arg Gln Ala Pro Gly Asn Gly Leu Glu Trp Val
         35                  40                  45

Ala Ile Ile Trp His Asp Gly Asn Lys Lys Tyr Tyr Ala Asp Ser Val
 50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Val Glu Asp Thr Ala Val Tyr Tyr Cys
                 85                  90                  95

Ala Arg Glu Met Asn Gly Ile Asp Val Trp Gly Gln Gly Thr Thr Val
                100                 105                 110

Thr Val Ser Ser
        115

<210> SEQ ID NO 19
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 19A1-VL variable light chain (VL) sequence,
      lambda type
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(291)
<223> OTHER INFORMATION: complementarity determining region (CDR)
      VL-CDR3

<400> SEQUENCE: 19 tcc tat gag ctg acc cag cca ccc tcg gtg tca gtg tcc cca gga caa    48
Ser Tyr Glu Leu Thr Gln Pro Pro Ser Val Ser Val Ser Pro Gly Gln
 1               5                  10                  15 acg gcc agg atc acc tgc tct gga gat gcg ttg cca gaa aca tat gtt    96
Thr Ala Arg Ile Thr Cys Ser Gly Asp Ala Leu Pro Glu Thr Tyr Val
             20                  25                  30 tat tgg tac cag cag aag tca ggc cag gcc cct gtg aag ctc atc tat   144
Tyr Trp Tyr Gln Gln Lys Ser Gly Gln Ala Pro Val Lys Leu Ile Tyr
         35                  40                  45 gag gac agc gaa cga ccc tcc ggg atc cct gag aga ttc tct ggc tcc   192
Glu Asp Ser Glu Arg Pro Ser Gly Ile Pro Glu Arg Phe Ser Gly Ser
 50                  55                  60 agc tca ggg aca ttg gcc acc ttg act atc agt ggg gcc cat gtg gag   240
Ser Ser Gly Thr Leu Ala Thr Leu Thr Ile Ser Gly Ala His Val Glu
 65                  70                  75                  80 gat gaa gct gac tac tac tgt tac tca aca gac agt agt ggt atc ggg   288
Asp Glu Ala Asp Tyr Tyr Cys Tyr Ser Thr Asp Ser Ser Gly Ile Gly
                 85                  90                  95 gtg ttc gga gga ggg acc aag ctg acc gtc cta                       321
Val Phe Gly Gly Gly Thr Lys Leu Thr Val Leu
            100                 105

<210> SEQ ID NO 20
<211> LENGTH: 107
<212> TYPE: PRT
<213> ORGANISM: Homo sapiens
```

<400> SEQUENCE: 20

| Ser | Tyr | Glu | Leu | Thr | Gln | Pro | Pro | Ser | Val | Ser | Val | Ser | Pro | Gly | Gln |
| 1 | | | | 5 | | | | | 10 | | | | | 15 | |

| Thr | Ala | Arg | Ile | Thr | Cys | Ser | Gly | Asp | Ala | Leu | Pro | Glu | Thr | Tyr | Val |
| | | | 20 | | | | | 25 | | | | | 30 | | |

| Tyr | Trp | Tyr | Gln | Gln | Lys | Ser | Gly | Gln | Ala | Pro | Val | Lys | Leu | Ile | Tyr |
| | | 35 | | | | | 40 | | | | | 45 | | | |

| Glu | Asp | Ser | Glu | Arg | Pro | Ser | Gly | Ile | Pro | Glu | Arg | Phe | Ser | Gly | Ser |
| 50 | | | | | 55 | | | | | 60 | | | | | |

| Ser | Ser | Gly | Thr | Leu | Ala | Thr | Leu | Thr | Ile | Ser | Gly | Ala | His | Val | Glu |
| 65 | | | | 70 | | | | | 75 | | | | | 80 | |

| Asp | Glu | Ala | Asp | Tyr | Tyr | Cys | Tyr | Ser | Thr | Asp | Ser | Ser | Gly | Ile | Gly |
| | | | | 85 | | | | | 90 | | | | | 95 | |

| Val | Phe | Gly | Gly | Gly | Thr | Lys | Leu | Thr | Val | Leu |
| | | | 100 | | | | | 105 | | |

<210> SEQ ID NO 21
<211> LENGTH: 993
<212> TYPE: DNA
<213> ORGANISM: Homo sapiens
<220> FEATURE:
<221> NAME/KEY: CDS
<222> LOCATION: (1)..(993)
<223> OTHER INFORMATION: 19A1-CH constant heavy chain (CH) sequence

<400> SEQUENCE: 21

| gcc tcc acc aag ggc cca tcg gtc ttc ccc ctg gca ccc tcc tcc aag | 48 |
| Ala Ser Thr Lys Gly Pro Ser Val Phe Pro Leu Ala Pro Ser Ser Lys | |
| 1               5                   10                  15     | |

| agc acc tct ggg ggc aca gcg gcc ctg ggc tgc ctg gtc aag gac tac | 96 |
| Ser Thr Ser Gly Gly Thr Ala Ala Leu Gly Cys Leu Val Lys Asp Tyr | |
|             20                  25                  30         | |

| ttc ccc gaa ccg gtg acg gtg tcg tgg aac tca ggc gcc ctg acc agc | 144 |
| Phe Pro Glu Pro Val Thr Val Ser Trp Asn Ser Gly Ala Leu Thr Ser | |
|         35                  40                  45             | |

| ggc gtg cac acc ttc ccg gct gtc cta cag tcc tca gga ctc tac tcc | 192 |
| Gly Val His Thr Phe Pro Ala Val Leu Gln Ser Ser Gly Leu Tyr Ser | |
|     50                  55                  60                 | |

| ctc agc agc gtg gtg acc gtg ccc tcc agc agc ttg ggc acc cag acc | 240 |
| Leu Ser Ser Val Val Thr Val Pro Ser Ser Ser Leu Gly Thr Gln Thr | |
| 65                  70                  75                  80 | |

| tac atc tgc aac gtg aat cac aag ccc agc aac acc aag gtg gac aag | 288 |
| Tyr Ile Cys Asn Val Asn His Lys Pro Ser Asn Thr Lys Val Asp Lys | |
|                 85                  90                  95     | |

| aga gtt gag ccc aaa tct tgt gac aaa act cac aca tgc cca ccg tgc | 336 |
| Arg Val Glu Pro Lys Ser Cys Asp Lys Thr His Thr Cys Pro Pro Cys | |
|             100                 105                 110        | |

| cca gca cct gaa ctc ctg ggg gga ccg tca gtc ttc ctc ttc ccc cca | 384 |
| Pro Ala Pro Glu Leu Leu Gly Gly Pro Ser Val Phe Leu Phe Pro Pro | |
|         115                 120                 125            | |

| aaa ccc aag gac acc ctc atg atc tcc cgg acc cct gag gtc aca tgc | 432 |
| Lys Pro Lys Asp Thr Leu Met Ile Ser Arg Thr Pro Glu Val Thr Cys | |
|     130                 135                 140                | |

| gtg gtg gtg gac gtg agc cac gaa gac cct gag gtc aag ttc aac tgg | 480 |
| Val Val Val Asp Val Ser His Glu Asp Pro Glu Val Lys Phe Asn Trp | |
| 145                 150                 155                 160 | |

| tac gtg gac ggc gtg gag gtg cat aat gcc aag aca aag ccg cgg gag | 528 |
| Tyr Val Asp Gly Val Glu Val His Asn Ala Lys Thr Lys Pro Arg Glu | |
|                 165                 170                 175    | |

```
gag cag tac aac agc acg tac cgt gtg gtc agc gtc ctc acc gtc ctg         576
Glu Gln Tyr Asn Ser Thr Tyr Arg Val Val Ser Val Leu Thr Val Leu
                180                 185                 190 cac cag gac tgg ctg aat ggc aag gag tac aag tgc aag gtc tcc aac         624
His Gln Asp Trp Leu Asn Gly Lys Glu Tyr Lys Cys Lys Val Ser Asn
            195                 200                 205 aaa gcc ctc cca gcc ccc atc gag aaa acc atc tcc aaa gcc aaa ggg         672
Lys Ala Leu Pro Ala Pro Ile Glu Lys Thr Ile Ser Lys Ala Lys Gly
        210                 215                 220 cag ccc cga gaa cca cag gtg tac acc ctg ccc cca tcc cgg gag gag         720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat         768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac         816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc         864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac         912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg         960
Val Phe Ser Cys Ser Val Met His Glu Ala Leu His Asn His Tyr Thr
305                 310                 315                 320 cag aag agc ctc tcc ctg tcc ccg ggt aaa tga                             993
Gln Lys Ser Leu Ser Leu Ser Pro Gly Lys
                325                 330

<210> SEQ ID NO 22
<211> LENGTH: 330
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
        260                 265                 270
Asn Tyr Lys Thr Thr Pro Pro Val Leu Asp Ser Asp Gly Ser Phe Phe
    275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 23
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 19A1-CL constant lambda chain (CL) sequence
<220> FEATURE:
<221> NAME/KEY: misc_feature
<222> LOCATION: (271)..(321)
<223> OTHER INFORMATION: not sequenced but obtained from database

<400> SEQUENCE: 23 agt cag ccc aag gct gcc ccc tcg gtc act ctg ttc ccg ccc tcc tct       48
Ser Gln Pro Lys Ala Ala Pro Ser Val Thr Leu Phe Pro Pro Ser Ser
1               5                   10                  15 gag gag ctt caa gcc aac aag gcc aca ctg gtg tgt ctc ata agt gac       96
Glu Glu Leu Gln Ala Asn Lys Ala Thr Leu Val Cys Leu Ile Ser Asp
            20                  25                  30 ttc tac ccg gga gcc gtg aca gtg gcc tgg aag gca gat agc agc ccc      144
Phe Tyr Pro Gly Ala Val Thr Val Ala Trp Lys Ala Asp Ser Ser Pro
        35                  40                  45 gtc aag gcg gga gtg gag acc acc aca ccc tcc aaa caa agc aac aac      192
Val Lys Ala Gly Val Glu Thr Thr Thr Pro Ser Lys Gln Ser Asn Asn
50                  55                  60 aag tac gcg gcc agc agc tac ctg agc ctg acg cct gag cag tgg aag      240
Lys Tyr Ala Ala Ser Ser Tyr Leu Ser Leu Thr Pro Glu Gln Trp Lys
65                  70                  75                  80 tcc cac aaa agc tac agc tgc cag gtc aca cat gaa ggg agc acc gtg      288
Ser His Lys Ser Tyr Ser Cys Gln Val Thr His Glu Gly Ser Thr Val
                85                  90                  95 gag aag aca gtg gcc cct aca gaa tgt tca tag                          321
Glu Lys Thr Val Ala Pro Thr Glu Cys Ser
            100                 105
```

```
<210> SEQ ID NO 24
<211> LENGTH: 106
<212> TYPE: PRT
<213> ORGANISM: Homo sapiens

<400> SEQUENCE: 24

Ser Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 25
<211> LENGTH: 348
<212> TYPE: DNA
<213> ORGANISM: Homo sapiens
<220> FEATURE:
<221> NAME/KEY: CDS
<222> LOCATION: (1)..(348)
<223> OTHER INFORMATION: 26A6-VH variable heavy chain (VH) sequence;
      26A6: IgG1, lambda
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(315)
<223> OTHER INFORMATION: complementarity determining region (CDR)
      VH-CDR3

<400> SEQUENCE: 25 cag gtg cag ctg gtg gag tct ggg gga ggc gtg gtc cag cct ggg agg      48
Gln Val Gln Leu Val Glu Ser Gly Gly Gly Val Val Gln Pro Gly Arg
1               5                   10                  15 tcc ctg aga ctc tcc tgt gta gcg tct gga ctc act ttc agg acc tat      96
Ser Leu Arg Leu Ser Cys Val Ala Ser Gly Leu Thr Phe Arg Thr Tyr
            20                  25                  30 ggc atg cac tgg gtc cgc cag gct cca ggc aac ggg ctg gag tgg gtg     144
Gly Met His Trp Val Arg Gln Ala Pro Gly Asn Gly Leu Glu Trp Val
        35                  40                  45 gca atc ata tgg cat gat ggt aat aaa aaa tac ttt gct gac tcc gta     192
Ala Ile Ile Trp His Asp Gly Asn Lys Lys Tyr Phe Ala Asp Ser Val
    50                  55                  60 aag ggc cga ttc acc atc tcc agg gac aat tcc aag aac agt cta tat     240
Lys Gly Arg Phe Thr Ile Ser Arg Asp Asn Ser Lys Asn Ser Leu Tyr
65                  70                  75                  80 ctc caa atg aac agc ctg aga gtc gag gac acg gct gtt tat tac tgt     288
Leu Gln Met Asn Ser Leu Arg Val Glu Asp Thr Ala Val Tyr Tyr Cys
                85                  90                  95
```

```
gcg aga gaa atg aat ggc atc gac gtc tgg ggc caa ggg acc acg gtc      336
Ala Arg Glu Met Asn Gly Ile Asp Val Trp Gly Gln Gly Thr Thr Val
                100                 105                 110 acc gtc tcc tca                                                      348
Thr Val Ser Ser
        115
```

<210> SEQ ID NO 26
<211> LENGTH: 116
<212> TYPE: PRT
<213> ORGANISM: Homo sapiens

<400> SEQUENCE: 26

```
Gln Val Gln Leu Val Glu Ser Gly Gly Gly Val Val Gln Pro Gly Arg
1               5                   10                  15

Ser Leu Arg Leu Ser Cys Val Ala Ser Gly Leu Thr Phe Arg Thr Tyr
            20                  25                  30

Gly Met His Trp Val Arg Gln Ala Pro Gly Asn Gly Leu Glu Trp Val
        35                  40                  45

Ala Ile Ile Trp His Asp Gly Asn Lys Lys Tyr Phe Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Glu Met Asn Gly Ile Asp Val Trp Gly Gln Gly Thr Thr Val
                100                 105                 110

Thr Val Ser Ser
        115
```

<210> SEQ ID NO 27
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 26A6-VL variable light chain (VL) sequence,
      lambda type
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(291)
<223> OTHER INFORMATION: complementarity determining region (CDR)
      VL-CDR3

<400> SEQUENCE: 27

```
tcc tat gag ctg acc cag cca ccc tcg gtg tca gtg tcc cca gga caa      48
Ser Tyr Glu Leu Thr Gln Pro Pro Ser Val Ser Val Ser Pro Gly Gln
1               5                   10                  15 acg gcc agg atc acc tgc tct gga gat gcg ttg cca gaa aca tat gtt      96
Thr Ala Arg Ile Thr Cys Ser Gly Asp Ala Leu Pro Glu Thr Tyr Val
            20                  25                  30 tat tgg tac cag cag aag tca ggc cag gcc cct gtg aag ctc atc tat     144
Tyr Trp Tyr Gln Gln Lys Ser Gly Gln Ala Pro Val Lys Leu Ile Tyr
        35                  40                  45
```

```
gag gac agc gaa cga ccc tcc ggg atc cct gag aga ttc tct ggc tcc    192
Glu Asp Ser Glu Arg Pro Ser Gly Ile Pro Glu Arg Phe Ser Gly Ser
 50                  55                  60 agc tca ggg aca ttg gcc acc ttg act atc agt ggg gcc cat gtg gag    240
Ser Ser Gly Thr Leu Ala Thr Leu Thr Ile Ser Gly Ala His Val Glu
 65                  70                  75                  80 gat gaa gct gac tac tac tgt tac tca aca gac agt agt ggt atc ggg    288
Asp Glu Ala Asp Tyr Tyr Cys Tyr Ser Thr Asp Ser Ser Gly Ile Gly
                 85                  90                  95 gtg ttc gga gga ggg acc aag gtg acc gtc cta                        321
Val Phe Gly Gly Gly Thr Lys Val Thr Val Leu
            100                 105

<210> SEQ ID NO 28
<211> LENGTH: 107
<212> TYPE: PRT
<213> ORGANISM: Homo sapiens

<400> SEQUENCE: 28

Ser Tyr Glu Leu Thr Gln Pro Pro Ser Val Ser Val Ser Pro Gly Gln
  1               5                  10                  15

Thr Ala Arg Ile Thr Cys Ser Gly Asp Ala Leu Pro Glu Thr Tyr Val
             20                  25                  30

Tyr Trp Tyr Gln Gln Lys Ser Gly Gln Ala Pro Val Lys Leu Ile Tyr
         35                  40                  45

Glu Asp Ser Glu Arg Pro Ser Gly Ile Pro Glu Arg Phe Ser Gly Ser
 50                  55                  60

Ser Ser Gly Thr Leu Ala Thr Leu Thr Ile Ser Gly Ala His Val Glu
 65                  70                  75                  80

Asp Glu Ala Asp Tyr Tyr Cys Tyr Ser Thr Asp Ser Ser Gly Ile Gly
                 85                  90                  95

Val Phe Gly Gly Gly Thr Lys Val Thr Val Leu
            100                 105

<210> SEQ ID NO 29
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 26A6-CL constant lambda chain (CL) sequence
<220> FEATURE:
<221> NAME/KEY: misc_feature
<222> LOCATION: (271)..(321)
<223> OTHER INFORMATION: not sequenced but obtained from database

<400> SEQUENCE: 29 agt cag ccc aag gct gcc ccc tcg gtc act ctg ttc ccg ccc tcc tct     48
Ser Gln Pro Lys Ala Ala Pro Ser Val Thr Leu Phe Pro Pro Ser Ser
  1               5                  10                  15 gag gag ctt caa gcc aac aag gcc aca ctg gtg tgt ctc ata agt gac     96
Glu Glu Leu Gln Ala Asn Lys Ala Thr Leu Val Cys Leu Ile Ser Asp
             20                  25                  30 ttc tac ccg gga gcc gtg aca gtg gcc tgg aag gca gat agc agc ccc    144
Phe Tyr Pro Gly Ala Val Thr Val Ala Trp Lys Ala Asp Ser Ser Pro
         35                  40                  45 gtc aag gcg gga gtg gag acc acc aca ccc tcc aaa caa agc aac aac    192
Val Lys Ala Gly Val Glu Thr Thr Thr Pro Ser Lys Gln Ser Asn Asn
 50                  55                  60
```

-continued

```
aag tac gcg gcc agc agc tac ctg agc ctg acg cct gag cag tgg aag    240
Lys Tyr Ala Ala Ser Ser Tyr Leu Ser Leu Thr Pro Glu Gln Trp Lys
65              70                  75                  80 tcc cac aaa agc tac agc tgc cag gtc aca cat gaa ggg agc acc gtg    288
Ser His Lys Ser Tyr Ser Cys Gln Val Thr His Glu Gly Ser Thr Val
                85                  90                  95 gag aag aca gtg gcc cct aca gaa tgt tca tag                         321
Glu Lys Thr Val Ala Pro Thr Glu Cys Ser
            100                 105

<210> SEQ ID NO 30
<211> LENGTH: 106
<212> TYPE: PRT
<213> ORGANISM: Homo sapiens

<400> SEQUENCE: 30

Ser Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65              70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105
```

HUMAN ANTI-IL-32 ANTIBODIES AND METHODS OF MAKING AND USING THE SAME

CROSS REFERENCE TO RELATED APPLICATIONS

This application is a U.S. national stage application under 35 U.S.C. 371 and claims the benefit of PCT Application No. PCT/EP2014/064163 having an international filing date of Jul. 3, 2014, which designated the United States, which PCT application claimed the benefit of European Patent Application No. 13174937.6 filed Jul. 3, 2013, the disclosures of each of which are incorporated herein by reference.

REFERENCE TO SEQUENCE LISTING

This application contains a Sequence Listing submitted in a computer readable format (CRF) as an electronic (ASCII) text file named "WO2015001010SequenceListing.txt", having a size in bytes of 61,000 bytes, and created on Jul. 2, 2014. The information contained in this electronic file is hereby incorporated by reference in its entirety pursuant to 37 CFR § 1.52(e)(5). The sequence listing content of the PDF copy forming part of the international application (paper copy) and this CRF ASCII text file copy are identical.

FIELD OF THE INVENTION

The present invention generally relates to novel molecules binding Interleukin-32 (IL-32) of mammal, preferably human origin, particularly human monoclonal antibodies as well as fragments, derivatives and variants thereof. In particular, the present invention relates to recombinant human patient-derived anti-IL-32 antibodies and IL-32 binding fragments thereof. In addition, compositions comprising such binding molecules, antibodies and mimics thereof useful in the treatment and diagnosis of disorders are described. Furthermore, the present invention relates to the anti-IL-32 antibodies and mentioned equivalents thereof for use in immunotherapy as well as targets in the therapeutic intervention of autoimmune and autoinflammatory disorders as well as malignancies, such as various forms of arthritis, inflammatory bowel disease (IBD), myasthenia gravis (MG), chronic obstructive pulmonary disease (COPD), asthma, vascular inflammation & atherosclerosis, atopic dermatitis and cancer.

BACKGROUND OF THE INVENTION

Inappropriate responses of the immune system may cause stressful symptoms to the involved organism. Exaggerated immune answers to foreign substances or physical states which usually do not have a significant effect on the health of an animal or human may lead to allergies with symptoms ranging from mild reactions, such as skin irritations to life-threatening situations such as an anaphylactic shock or various types of vasculitis. Immune answers to endogenous antigens may cause autoimmune disorders such as systemic lupus erythematosus, idiopathic autoimmune hemolytic anemia, pernicious anemia, type 1 diabetes mellitus, blistering skin diseases and different kinds of arthritis.

Immune responses occur in a coordinated manner, involving several cell types and requiring communication by signaling molecules such as cytokines between the cell types involved. This communication may be influenced or inhibited by, e.g., interception of the signals or block of the respective receptors.

Cytokines are secreted soluble proteins, peptides and glycoproteins acting as humoral regulators at nano- to picomolar concentrations behaving like classical hormones in that they act at a systemic level and which, either under normal or pathological conditions, modulate the functional activities of individual cells and tissues. Cytokines differ from hormones in that they are not produced by specialized cells organized in specialized glands, i.e. there is not a single organ or cellular source for these mediators as they are expressed by virtually all cells involved in innate and adaptive immunity such as epithelial cells, macrophages, dendritic cells (DC), natural killer (NK) cells and especially by T cells, prominent among which are T helper (Th) lymphocytes.

Depending on their respective functions, cytokines may be classified into three functional categories: regulating innate immune responses, regulating adaptive immune responses and stimulating hematopoiesis. Due to their pleiotropic activities within said three categories, e.g., concerning cell activation, proliferation, differentiation, recruitment, or other physiological responses, e.g., secretion of proteins characteristic for inflammation by target cells, disturbances of the cell signaling mediated by aberrantly regulated cytokine production have been found as a cause of many disorders associated with defective immune response, for example, inflammation and cancer.

Interleukin-32 (IL-32, also known as Natural killer cells protein 4) is a recently discovered cytokine with important functions in host defense and innate immunity. The human IL-32 gene is located on chromosome 16p13.3. Besides human and simian, so far bovine, swine and equine homologues have been found, however no mouse homologues are known so far. Six IL-32 isoforms are known, produced by alternative splicing (Chen et al., *Vitam Horm* 74 (2006), 207-228). The longest isoform, IL-32gamma (IL-32γ or IL-32g), comprises 234aa (UniProtKB/Swiss-Prot identifier: P24001-1). The second isoform, also known as IL-32beta (IL-32β or IL-32b; UniProtKB/Swiss-Prot identifier: P24001-2) has 188aa. The third isoform of 178aa is also known as IL-32delta (IL-32δ or IL-32d; UniProtKB/Swiss-Prot identifier: P24001-3). IL-32alpha (IL-32α or IL-32a) of 131aa is the fourth isoform (UniProtKB/Swiss-Prot identifier: P24001-4). Isoform 5 (UniProtKB/Swiss-Prot identifier: P24001-5) and isoform 6 UniProtKB/Swiss-Prot identifier: P24001-6) have 168aa respective 179aa. However, also further isotypes may exist, e.g., a 112 aa potential new isotype has been reported by Imaeda et al., (*Mol Med Rep.* 4 (2011), 483-487).

The receptor for IL-32 is unknown so far. However, some data exist indicating that IL-32 may be bound and cleaved at the cell membrane by proteinase 3 implicating this molecule as a possible receptor, wherein the produced fragments may have biological activity and activate macrophage inflammatory protein-2 and IL-8 (Dinarello and Kim, *Ann Rheum Dis.* 65 Suppl. 3 (2006); iii 61-64). IL-32 is implicated as a major controller of inflammatory pathways with a pronounced synergy with TNFα in form of a self-perpetuating loop where IL-32 promotes TNFα expression and vice versa resulting in the amplification of proinflammatory mediators. It has been reported to induce various cytokines such as TNFA/TNF-alpha, IL-1β, IL-6, IL-8, and macrophage inflammatory protein-2 (MIP-2), to activate typical cytokine signaling pathways of NF-kappa-B and p38 MAPK and it is an IL-18 inducible gene (Kim et al., *Immunity* 22 (2005), 131-142; Netea et al., *Proc Natl Acad Sci USA.* 105 (2008), 3515-3520; Netea et al., *Proc Natl Acad Sci USA.* 102 (2005), 16309-16314; Joosten et al., *Proc. Natl. Acad. Sci. USA* 103 (2006), 3298-3303). Recently, it was also shown that IL-32 increases IFN-γ production by Peripheral Blood Mononuclear Cells (PBMCs; Nold et al., *J Immunol.* 181 (2008), 557-565; Netea et al., *PLoS Med.* 3 (2006), e277).

IL-32 has been reported as being produced mainly by NK cells, T lymphocytes, epithelial cells, and blood monocytes stimulated by IL-2 or IFN-γ (Dahl et al., *J Immunol.* 148 (1992), 597-603; Kim et al., (2005)). Furthermore, IL-32 has been observed to be overexpressed in rheumatoid arthritis (RA) synovial tissue biopsies, wherein the level of IL-32 expression correlated positively with the severity of inflammation (Alsaleh et al., *Arthritis Res Ther.* 12 (2010), R135; Cagnard et al., *Eur Cytokine Netw.* 16 (2005), 289-292.). Besides various forms of arthritis, such as rheumatoid arthritis (RA) or ankylosing spondylitis (Ciccia et al., *Rheumatology* 51 (2012), 1966-1972), which belongs to the family of spondyloarthropathies, IL-32 was found functionally associated with several other inflammatory bowel disease (IBD), myasthenia gravis (MG), chronic obstructive pulmonary disease (COPD), asthma, Crohn's disease, psoriasis, atopic dermatitis and cancer (Alsaleh et al., (2010); Breenan and Beech, *Curr. Opin. Rheumatol.*, 19 (2007), 296-301; Asquith and McInnes, *Curr. Opin. Rheumatol.*, 19 (2007), 246-251; Dinarello and Kim, *Ann Rheum Dis.* 65 Suppl 3 (2006); iii 61-64; Fantini et al., *Inflamm Bowel Dis.* 13 (2007), 1419-1423; Lee et al., *Oncology Letters* 3 (2012), 490-496). The high rate of atherosclerosis in RA suggested also a possible role of IL-32 in the inflammatory pathways of vascular inflammation and atherosclerosis, which implications have been also verified, e.g., by detection of IL-32 expression, with the expression of IL-32β and IL-32γ mRNA significantly enhanced in human atherosclerotic arterial vessel wall (Kobayashi et al., *PLoS One.* 5 (2010); e9458; Heinhuis et al., Cytokine. (2013), S1043-4666). IL-32 may also play a role in immune responses to tuberculosis (Kundu and Basu, *PLoS Med.*, 3 (2006), e274; Netea et al., 2006). Also, increased transcription of IL-32 has been observed after infection by bacteria and viruses, such as *Mycobacterium tuberculosis* (Netea et al., 2006) or Influenza A (Li at al., *PLoS One.* 3 (2008), e1985) indicating its possible role in host defense.

Accordingly, IL-32 represents a not yet fully understood, however, important new therapeutic target and there is requirement for IL-32 specific binding molecules, which neutralize the function of all IL-32 isotypes, selected subranges thereof or singular IL-32 isotypes, e.g., IL-32γ.

First attempts to provide such molecules have been already met. For example, U.S. Pat. No. 7,641,904 B2 by Kim et al. provides murine IL-32 monoclonal antibodies, wherein one of the antibodies selectively recognizes IL-32α, wherein another antibody binds IL-32α, IL-32ß, and IL-32γ. International application WO 2005/047478 describes the generation of murine antibody fragments specific for IL-32α and IL-32β. However, apparently no antibodies specific for IL-32γ have been provided yet.

Furthermore, due to immunological responses to foreign antibodies, as mouse antibodies in humans (HAMA-response; Schroff et al., *Cancer Res.* 45 (1985), 879-885; Shawler et al., *J. Immunol.* 135 (1985), 1530-1535), mostly humanized versions of antibodies are used in present therapeutic approaches (Chan et Carter, *Nature Reviews Immunology* 10 (2010), 301-316; Nelson et al., *Nature Reviews Drug Discovery* 9 (2010), 767-774). One approach to gain such antibodies was to transplant the complementarity determining regions (CDR) into a completely human framework, a process known as antibody humanization (Jones et al., *Nature* 321 (1986), 522-525). This approach is often complicated by the fact that mouse CDR do not easily transfer to a human variable domain framework, resulting in lower affinity of the humanized antibody over their parental murine antibody. Therefore, additional and elaborate mutagenesis experiments are often required, to increase the affinity of the so engineered antibodies. Another approach for achieving humanized antibodies is to immunize mice which have had their innate antibody genes replaced with human antibody genes and to isolate the antibodies produced by these animals. However, this method still requires immunization with an antigen, which is not possible with all antigens because of the toxicity of some of them. Furthermore, this method is limited to the production of transgenic mice of a specific strain.

Another method to generate antibodies is to use libraries of human antibodies, such as phage display, as described, for example, for the generation of IL-13 specific antibodies in international application WO 2005/007699. Here, bacteriophages are engineered to display human scFv/Fab fragments on their surface by inserting a human antibody gene into the phage population. Unfortunately, there is a number of disadvantages of this method as well, including size limitation of the protein sequence for polyvalent display, the requirement of secretion of the proteins, i.e. antibody scFv/Fab fragments, from bacteria, the size limits of the library, limited number of possible antibodies produced and tested, a reduced proportion of antibodies with somatic hypermutations produced by natural immunization and that all phage-encoded proteins are fusion proteins, which may limit the activity or accessibility for the binding of some proteins. A further severe drawback of this technique is that the antibodies so produced bear the risk of undesired cross-reactivity against self-antigens and lack the characteristics of evolutionary optimized natural human antibodies produced by the human immune system. Furthermore, such antibodies may not be specific enough because of cross-reactivity with other proteins and/or with the target protein in context with normal physiological environment and function. Similarly, European patent application EP 0 616 640 A1 describes the production of auto-antibodies from antibody segment repertoires displayed on phage. Phage libraries are generated from unimmunized humans in this respect (see, e.g., Example 1; page 16, lines 43-51; Example 2, at page 17, paragraph [0158], lines 57-58). However, also the methods described in this patent application suffer from above mentioned general disadvantages of antibodies generated from phage libraries, in comparison to antibodies produced and matured in a mammalian, i.e. human body.

In view of the above, there is still a need for additional and new compounds for treatment and diagnosis of disorders or conditions associated with detrimental IL-32 activity, like binding molecules of high specificity for IL-32 or specific for a selected range of or a single IL-32 isotype, in particular of antibodies specific for IL-32γ, which are tolerable in humans either for monotherapy or combinatorial approaches.

The solution to this problem is provided by the embodiments of the present invention as characterized in the claims and disclosed in the description and illustrated in the Examples and Figures further below.

SUMMARY OF THE INVENTION

The present invention relates to IL-32 specific human monoclonal antibodies and IL-32 binding fragments and derivatives thereof. In particular, human monoclonal anti-IL-32 antibodies are provided with a selective binding profile towards IL-32 isotypes and displaying binding and neutralizing activity in vitro and in vivo as shown in the appended Examples and the Figures. Due to their neutralization properties, the antibodies of the present invention have therapeutic, prognostic and diagnostic utility, which make them in particular valuable for applications in relationship with diverse autoimmune and inflammatory disorders and conditions associated with/involving IL-32 activity in initiation and/or maintenance of undesired immune responses, such as various forms of arthritis (e.g., rheumatoid arthritis (RA) or spondyloarthritis), myasthenia gravis (MG), inflammatory bowel disease (IBD), pulmonary diseases such as chronic obstructive pulmonary disease (COPD) and asthma, Crohn's disease, psoriasis, vascular inflammation & atherosclerosis, atopic dermatitis and cancer; see also the Background of the invention section above for these and further possible anti-IL-32 therapeutic and diagnostic indications.

The antibodies of the present invention have been isolated from mammals, in particular humans, which are affected with an impaired central and/or peripheral tolerance or loss of self-tolerance which may be due to or associated with a disrupted or deregulated genesis of self-tolerance, preferably caused by a monogenic autoimmune disorder. Examples of mammals which provide a particularly suitable source for autoantibodies in accordance with the present invention are mammals, e.g., humans having a disorder associated with a mutation in the AIRE (Autoimmune Regulator) gene such as Autoimmune polyendocrinopathy syndrome type 1 (APS1) (Peterson et al., *Nat. Rev. Immunol.* 8 (2008), 948-957), Autoimmune polyendocrinopathy syndrome type 2 (APS2) (Baker et al., *J. Clin. Endocrinol. Metab.* 95 (2010), E263-E270) and immunodysregulation polyendocrinopathy enteropathy X-linked syndrome (IPEX) (Powell et al., *J. Pediatr.* 100 (1982), 731-737; Ochs et al., *Immunol. Rev.* 203 (2005), 156-164). Preferably, the patients from whom the antibodies were isolated were displaying seroreactivity against at least one of the human IL-32 isotypes, most preferably towards IL-32γ.

In particular, experiments performed in accordance with the present invention were successful in the isolation of IL-32, in particular of IL-32γ-specific antibodies from APS1 patients. Therefore, the present invention generally relates to high affinity IL-32 neutralizing monoclonal antibodies. Accordingly, monoclonal human antibodies (mAbs, or MABs) against several or singular IL-32 isotypes, which will be described in detail below are provided by the present invention, which are considered to be safe and effective therapeutics for disorders in which those cytokines are involved.

Naturally, the present invention extends to nucleic acids, in particular cDNA encoding at least one variable, constant and/or complementarity determining region of the antibodies of the present invention, vectors comprising such nucleic acids, antibody producing cell lines and recombinant cells. The present invention further relates to pharmaceutical compositions, diagnostic assays and kits that comprise the binding molecules or peptides recognized by the antibodies isolated in accordance with the present invention and to therapeutic methods based thereon.

Further embodiments of the present invention will be apparent from the description and Examples that follow. When doing so, and if not indicated otherwise the terms "monoclonal antibody", "mAb", "MAB" and "MAb" are used interchangeably herein.

Furthermore, while the invention is illustrated and described by way of reference to the human-derived antibody originally obtained in the experiments performed in accordance with the present invention and described in the Examples it is to be understood that the antibody or antibody fragment of the present invention include synthetic and biotechnological derivatives of an antibody which means any engineered antibody or antibody-like IL-32-binding molecule, synthesized by chemical or recombinant techniques, which retains one or more of the functional properties of the subject antibody, in particular its neutralizing activity towards IL-32. Thus, while the present invention may be described for the sake of conciseness by way of reference to an antibody, unless stated otherwise synthetic and biotechnological derivatives thereof as well as equivalent IL-32 binding molecules are meant as well and included with the meaning of the term antibody.

BRIEF DESCRIPTION OF THE DRAWINGS

FIG. 1: Amino acid sequences of the variable region, i.e. heavy chain and kappa/lambda light chain (VH, VL) of IL-32 specific human antibodies of the present invention. A: antibody 2C2 (IgG3, lambda); B: antibody 14B3 (IgG1, lambda); C: antibody 19A1 (IgG1, lambda); D: antibody 26A6 (IgG1, lambda). Framework (FR) and complementarity determining regions (CDRs) are indicated with the CDRs being underlined.

DETAILED DESCRIPTION OF THE INVENTION

The present invention generally relates to novel molecules binding IL-32 of mammal, preferably human origin, particularly human monoclonal antibodies as well as fragments, derivatives and variants thereof that recognize different isotypes of IL-32.

There have been already efforts to provide IL-32 specific antibodies, as described in the background section, however, the antibodies provided and used at present are, as indicated above, not of human origin, which greatly impairs their therapeutic use in humans due to their immunogenicity. Furthermore, while murine antibodies against IL-32α or of a broader specificity against several IL-32 isotypes are available, they may have an undesirable side effect profile due to their broad binding specificity and potentially lead therefore to adverse effects and diseases. In addition, apparently no human IL-32γ specific antibodies are available yet.

As described in the examples, the subject antibodies of the present invention were isolated by a method disclosed in applicant's co-pending international application WO 2013/098419 A1, based on screening the sera of patients with an impaired central and/or peripheral tolerance or loss of self-tolerance, such as APECED/APS1 patients for autoantibodies against IL-32 proteins. Within these screens, the surprising observation was made that autoantibodies recognizing specific IL-32 isotypes were present in these sera. This cytokine has only recently been identified as a proinflammatory cytokine, and there is still relatively little known about its role in disease (at least compared with many other pro-inflammatory cytokines). In this connection, the presence of IL-32 autoantibodies in APS1 patients, which do not develop many of the common autoimmune and inflammatory conditions and diseases, such as RA, lends further support to an important role of this cytokine in the etiology of these diseases and validates the approach of the present invention, of its targeted antibody-based inhibition for therapeutic intervention, and its use in diagnostic applications.

Figure 2:
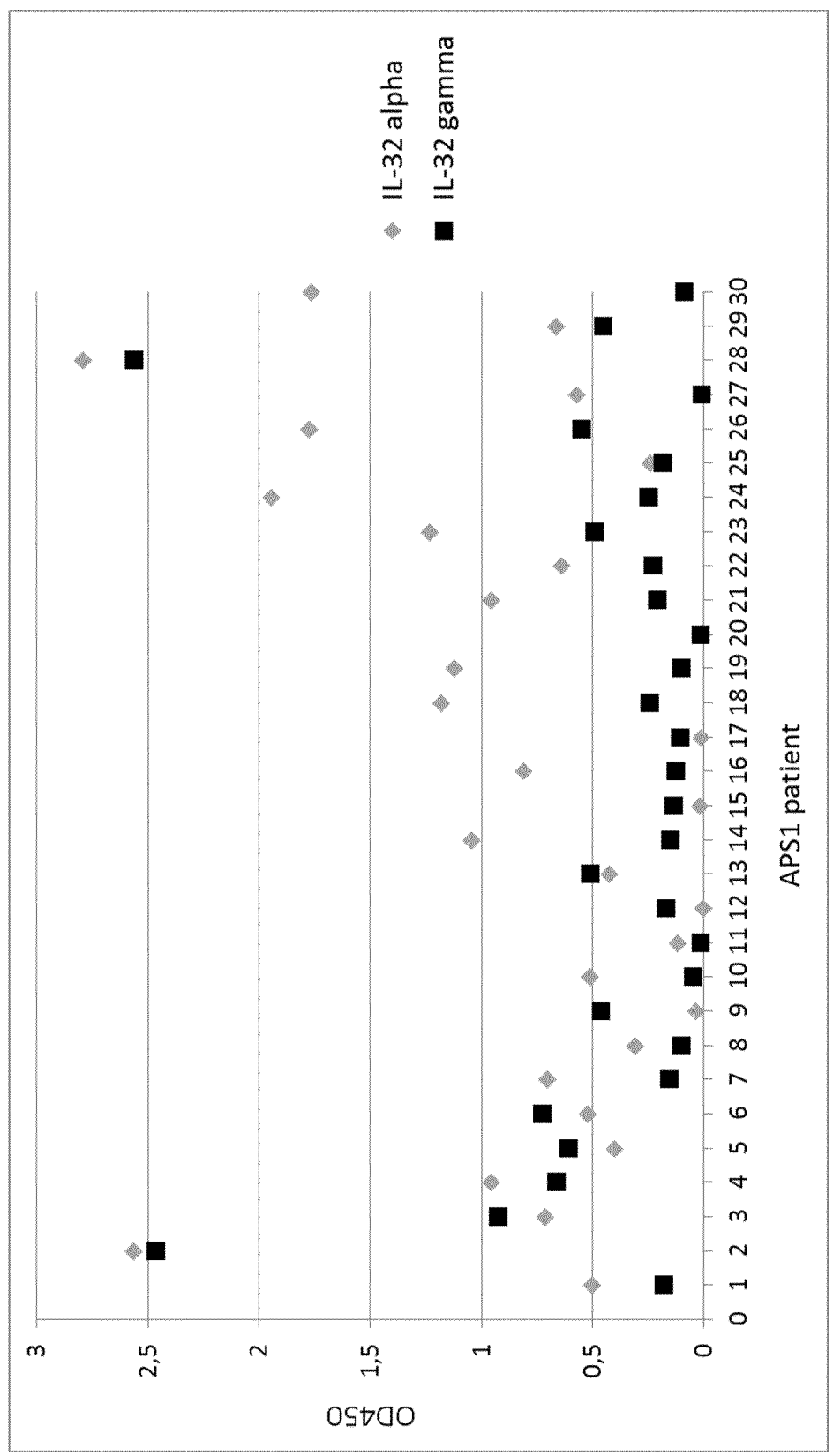
FIG. 2: Comparison of IL-32α (filled diamonds) and IL-32γ (filled squares) ELISA seroreactivities in sera isolated from APS1 patients. The individual patient is indicated on the X-axis and the OD450 measurements of MABs binding on the Y-axis.
Figure 3:
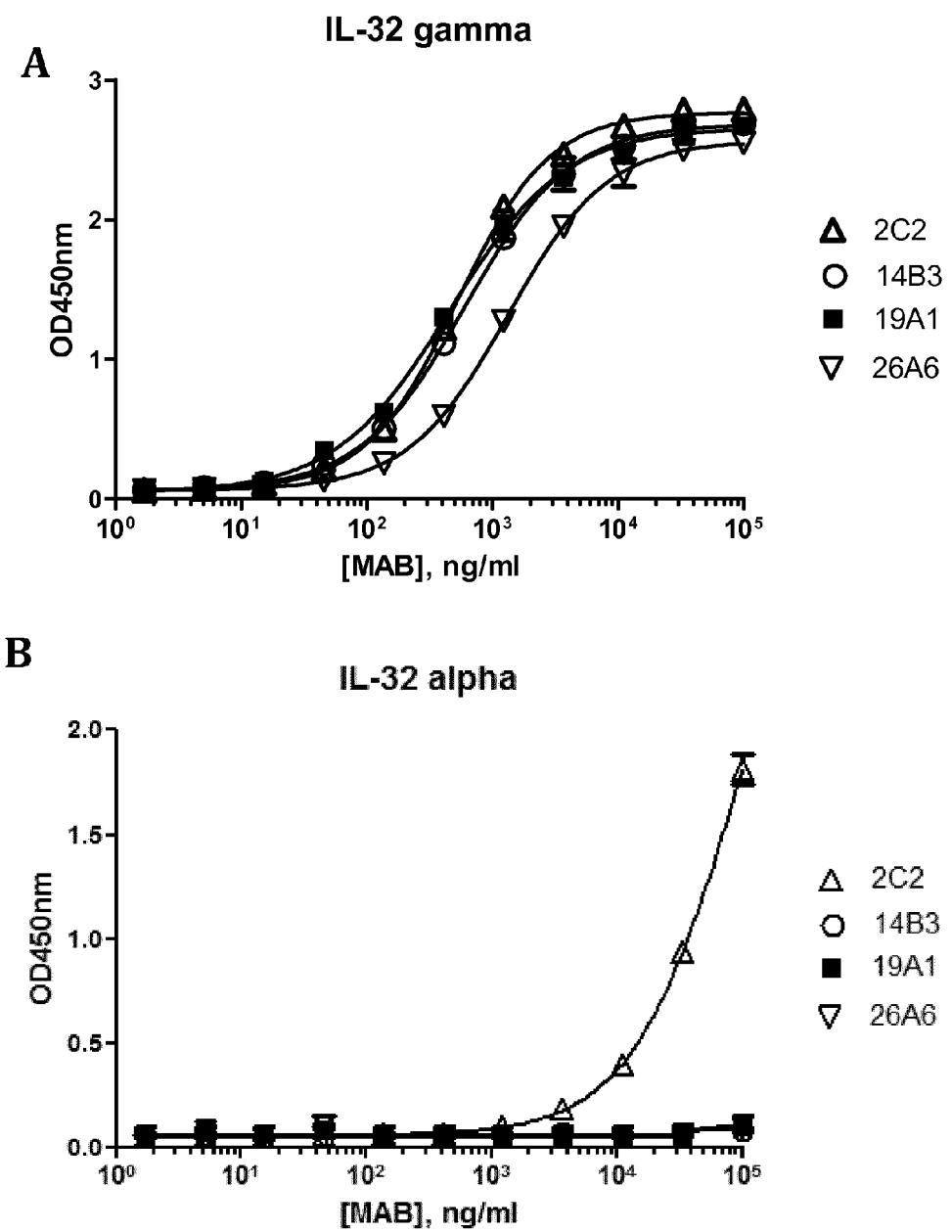
FIG. 3: EC50 ELISA determination of binding of exemplary anti-IL32 2C2, 14B3, 19A1 and 26A6 antibodies to A: IL-32γ (R&D) or B: IL-32α (ImmunoTools). All antibodies tested bind with high affinity IL-32γ. Antibody 2C2 binds with a low affinity IL-32α as well. Remaining antibodies 14B3, 19A1 and 26A6 do not show any substantial binding of IL-32α.
Figure 4:
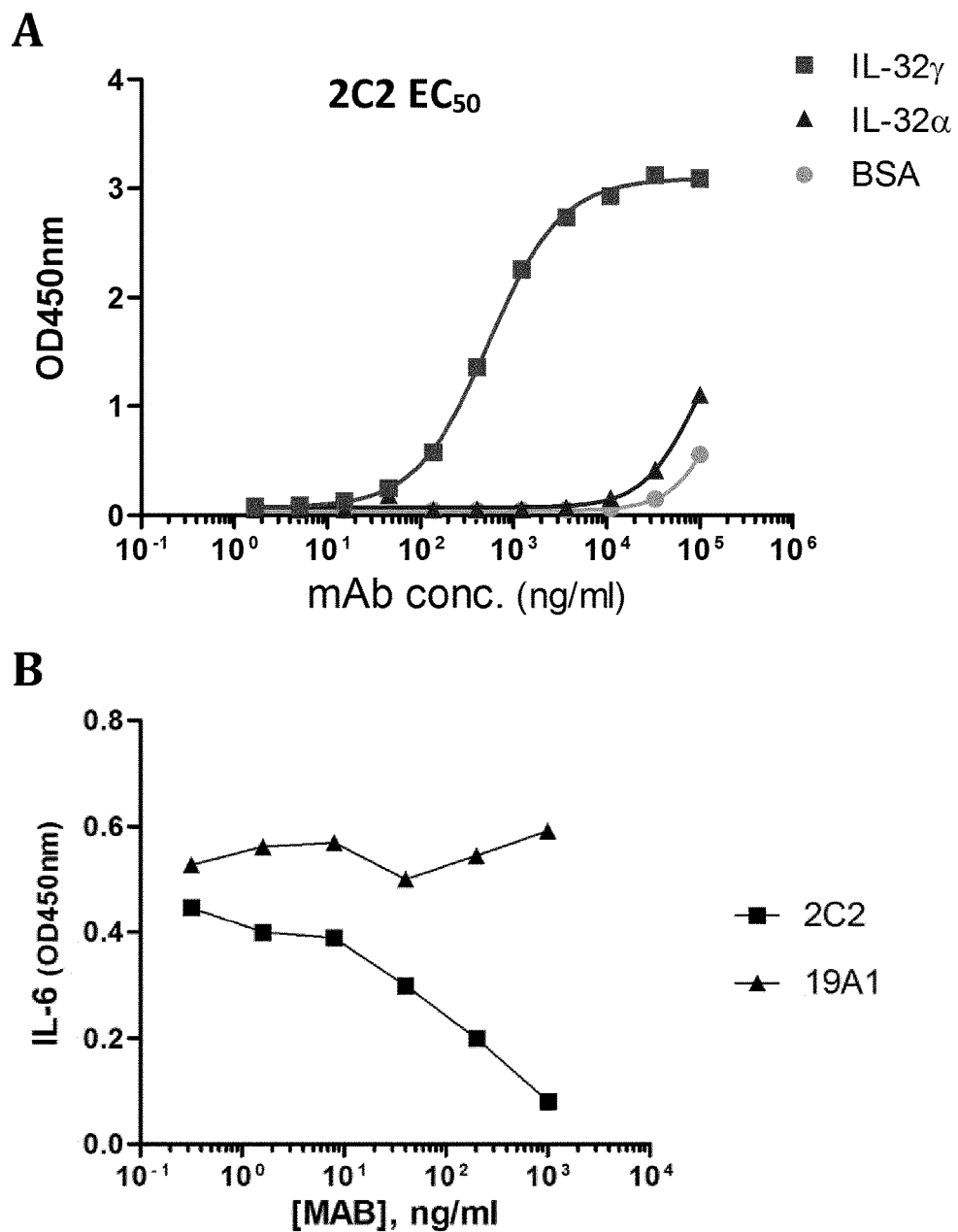
FIG. 4: Binding and neutralization characteristics of exemplary antibodies of the invention. A: EC50 ELISA determination of binding of exemplary anti-IL32 2C2 antibody to IL-32γ (R&D) and IL-32α (ImmunoTools), BSA used as control for non-specific binding. Exemplary antibody 2C2 binds with high affinity IL-32γ and with a much lower affinity IL-32α. B: Neutralization capacity of exemplary anti-IL32 antibodies 2C2 and 19A1 of IL-32γ activity.

In view of the above, experiments performed in accordance with the present invention were directed towards the provision of IL-32 binding molecules, in particular antibodies showing a binding specificity towards all IL-32 isotypes, or only a sub-range of IL-32 isotypes, or even only against a singular isotype, preferably specifically binding IL-32γ which immunoreactivity has been shown in APECED/APS1 patients to be protective against the onset of, e.g., RA and/or IBD. Preferably, the IL-32 binding molecules are capable of neutralizing a biological activity of IL-32. As illustrated by way of the exemplary anti-IL-32 2C2 antibody of the present invention in the appended Examples and Figures, in particular FIG. 3 and FIG. 4A showing the binding affinities, FIG. 4B and FIGS. 5, 6 and 9 to 12 showing the neutralizing activity and therapeutic utility of the subject antibody in an animal model, the problem underlying the present invention has been solved.

Accordingly, in its broadest aspect the present invention relates to recombinant human monoclonal anti-interleukin-32 (IL-32) antibodies and IL-32 binding fragments thereof as well as biotechnological derivatives thereof which bind one or more of the IL-32 isotypes; see also the background section supra for description of the IL-32 isotypes, including, e.g., IL-32γ, IL-32α, IL-32β and IL-32δ. In one embodiment, the human monoclonal anti-IL-32 antibody or IL-32 binding fragment thereof is capable of neutralizing a biological activity of IL-32γ and/or IL-32α. Concerning the binding and neutralization properties of the antibodies of the present invention they may be substantially equal towards the different IL-32 isotypes or may have a preferential binding and/or neutralizing activity towards the respective IL-32 isotypes.

In a preferred embodiment of the present invention, the human monoclonal anti-IL-32 antibody or IL-32 binding fragment thereof
(i) is capable of binding recombinant human IL-32gamma (IL-32γ);
(ii) is binding preferentially to human IL-32γ over IL32 alpha (IL-32α) and/or does not substantially bind IL-32α; and/or
(iii) is capable of neutralizing a biological activity of IL-32γ
Preferably, the antibody or IL-32 binding fragment thereof or an equivalent binding molecule of the present invention comprises in its variable region:
(a) at least one complementarity determining region (CDR) of the $V_H$ and/or $V_L$ variable region amino acid sequences depicted in
   (i) FIG. 1 ($V_H$) (SEQ ID NOs: 2, 10, 18 and 26); and
   (ii) FIG. 1 ($V_L$) (SEQ ID NOs: 4, 12, 20 and 28);
(b) an amino acid sequence of the $V_H$ and/or $V_L$ region as depicted in FIG. 1;
(c) at least one CDR consisting of an amino acid sequence resulted from a partial alteration of any one of the amino acid sequences of (a); and/or
(d) a heavy chain and/or light variable region comprising an amino acid sequence resulted from a partial alteration of the amino acid sequence of (b).

As described herein below in more detail, the antibody or antigen-binding fragment thereof of the present invention can be of or derived from any type, class or subclass of an immunoglobulin molecule. However, in a preferred embodiment, the antibody of the present invention is provided, which is of the IgG isotype, most preferably of the IgG1 or IgG3 subclass.

In order to provide such humanized, chimeric and in particular fully human antibodies and native Fab fragments thereof, in one embodiment the antibody or IL-32 binding fragment of the present invention further comprises a $C_H$ and/or $C_L$ constant region comprising an amino acid sequence selected from the $C_H$ and $C_L$ amino acid sequences set forth in Table 1 (SEQ ID NOs.: 6, 8, 14, 16, 22, 24 and 30) or an amino acid sequence with at least 60% identity, preferably 70% identity, more preferably 80% identity, still more preferably 90% identity, and particularly preferred at least 91%, 92%, 93%, 94%, 95%, 96%, 97%, 98% or 99%, identity to the mentioned reference sequences.

As described above, it has been found that IL-32 proinflammatory activity induces various cytokines such as TNFA/TNF-alpha, IL-1β, IL-6, IL-8, MIP-2 (see Kim et al., (2005); Netea et (2005); Netea et al., (2008); Joosten et al., (2006), supra). This activation mechanism has been used within the present invention for designing in vitro and in vivo assays for determining IL-32-activity, such as monitoring of the IL-6 expression by IL-32 stimulated RAW 264.7 macrophages and the ear inflammation assay as described in Example 3 and in FIGS. 4B, 5 and 6 to monitor the neutralizing properties of the antibodies of the present invention. As described in detail therein, the antibodies of the present invention have been found to have a potent neutralizing activity towards IL-32γ, wherein one antibody also shows residual binding activity towards IL-32α as specified in detail further below. Accordingly, in one embodiment the antibody or IL-32 binding fragment thereof of the present invention is capable of reducing the biological activity of human IL-32, preferably of IL-32γ. In a preferred embodiment the biological activity is human IL-32γ induced inflammation. Furthermore, in one embodiment of the present invention, the biological activity is determined in an IL-6 induction assay and/or ear inflammation assay.

Furthermore, the binding affinities of the antibodies of the present invention have been tested by ELISA as described herein, e.g., in Example 2 and shown in FIGS. 3 and 4A. In accordance with the results of these experiments, the present invention provides several exemplary anti-IL-32 antibodies and IL-32 binding fragments thereof showing a differential binding affinity towards distinct IL-32 isotypes, which exemplify the binding and neutralization characteristics of the IL-32 binding molecules provided herein.

Since the exemplary anti-IL-32 antibodies described in the Examples have been derived from a human patient, the present invention advantageously provides fully human antibodies particularly useful in therapeutic applications, which are substantially devoid of immunological responses otherwise typically observed for foreign antibodies, such as for mouse-derived antibodies in humans (HAMA-response) or humanized and human-like antibodies.

In this context, contrary to humanized antibodies and otherwise human-like antibodies, see also the discussion infra, the human-derived antibodies of the present invention are characterized by comprising CDRs which have been seen by human body and therefore are substantially devoid of the risk of being immunogenic. Therefore, the antibody of the present invention may still be denoted human-derived if at least one, preferably two and most preferably all three CDRs of one or both the variable light and heavy chain of the antibody are derived from the human antibodies illustrated herein.

The human-derived antibodies may also be called "human auto-antibodies" in order to emphasize that those antibodies were indeed expressed initially by the subjects and are not in vitro selected constructs generated, for example, by means of human immunoglobulin expressing phage libraries or xenogeneic antibodies generated in a transgenic animal expressing part of the human immunoglobulin repertoire, which hitherto represented the most common method for trying to provide human-like antibodies. On the other hand, the human-derived antibody of the present invention may be denoted synthetic, recombinant, and/or biotechnological in order to distinguish it from human serum antibodies per se, which may be purified via protein A or affinity column.

However, the present invention uses and envisages further studies of the antibodies of the present invention in animal models, e.g., in transgenic mice expressing human IL-32. To avoid immunogenic effects in the experimental animals analogous to the HAMA-response in humans, in one aspect, the antibody or binding fragment of the present invention is provided, which is a chimeric antibody, preferably a chimeric rodent-human or a rodentized antibody, mostly preferred a chimeric murine-human or a murinized antibody.

As mentioned above, the antibodies of the present invention have been isolated from APECED/APS1 patients. In this context, experiments disclosed in applicant's co-pending international application WO 2013/098419 A1 surprisingly revealed that APECED/APS1 patients display an auto-immunosome, i.e. an autoantibody profile comprising as well a broad spectrum of binding molecules specific for different IL-32 isotypes. APS1 is a rare autoimmune disease caused by mutations in the Autoimmune Regulator (AIRE) gene. The AIRE protein governs the expression in medullary thymic epithelium of many peripheral self-antigens (e.g., insulin) that are presented by MHC to tolerate developing thymocytes. In APS1, AIRE mutations cause aberrant negative selection, which enables autoreactive T cells to escape to the periphery. Accordingly, the patients show an extremely variable spectrum of clinical features in APS1, but usually with several autoimmune disorders of endocrine tissues. The defining APS1 triad comprises chronic mucocutaneous candidiasis, hypoparathyroidism and adrenal failure (Perheentupa, Endocrinol. Metab. Clin. North Am. 31 (2002), 295-320). Other clinical conditions seen in APECED patients include thyroid autoimmune diseases, diabetes mellitus, gonadal failure, vitiligo, alopecia, chronic hepatitis, chronic gastritis and pernicious anemia and different forms other gastrointestinal symptoms. For further details concerning APECED/APS1 patients and the screening of their auto-immunosome see the description of international application WO 2013/098419 A1 and the Examples described therein, in particular the Material and Methods section on pages 112-117; Example 1 on pages 117-118 and Example 7 on page 128 and the following Tables 1 to 14; and Example 17 on pages 168-171, the disclosure content of which is incorporated herein by reference.

As described in above, in one preferred embodiment, the antibody of the present invention is obtained or obtainable from a sample of a human subject affected with autoimmune polyendocrinopathy-candidiasis-ectodermal dystrophy (APECED/APS1) or from a patient affected with a similar autoimmune disease as described in international application WO 2013/098419 A1 and the Examples therein, in particular the Materials and Methods section on pages 112-117; Example 1 on pages 117-118; in Example 10 on pages 156-161, specifically in section "Patients and controls" on page 156 therein; and Example 17 on pages 168-171, the disclosure content of which is incorporated herein by reference. Furthermore, in a preferred embodiment the APS1 subject is characterized by displaying seroreactivity against human IL-32, preferably against IL-32γ and/or IL-32α.

In this context it is noted that the subject anti-IL-32 antibodies of the present invention have been cloned by a novel and proprietary method of isolating human antibodies, which is disclosed in applicant's co-pending international application WO 2013/098420 A1, the disclosure content of which is incorporated herein by reference.

Briefly, the sample for isolating the antibody of interest comprises or consists of peripheral blood mononuclear cells (PBMC) and serum for the detection of possible antibody reactivities. The sample derived from the subject may either be directly used for, e.g., testing seroreactivity against one or more of the desired antigen(s) or may be further processed, for example enriched for B lymphocytes. In particular, it is preferred that the sample comprises or is derived from B cells that produce the antibody of interest, most preferably memory B-cells. The memory B cells are cultured under conditions allowing only a definite life span of the B cells, typically no more than 1 to 2 weeks until singling out the cells from B cell cultures which are reactive against the desired antigen subsequently followed by RT-PCR of single sorted cells for obtaining the immunoglobulin gene repertoire; see for detailed description Examples 1 and 2 on pages 118 to 120 of WO 2013/098419 A1 and in particular Examples 1 to 4 on pages 27 to 31 of WO 2013/0984220 A1, the disclosure content of which is incorporated herein by reference. Naturally, the present invention extends to the human B memory lymphocyte and B cell, respectively, that produces the antibody having the distinct and unique characteristics as defined herein above and below.

Thus, besides using a selected patient pool, preferably an APS1 subject characterized by displaying seroreactivity against at least one of the human IL-32 isotypes neutralized by an exemplary antibody of the present invention, the anti-IL-32 antibodies have been provided by employing a particular method specifically developed and adapted for isolating human monoclonal antibodies from B cells of patients with an autoimmune disease such as APECED/APS1 patients.

In one embodiment, the antibody or IL-32 binding molecule of the present invention comprises an amino acid sequence of the $V_H$ and/or $V_L$ region as depicted in FIG. 1 or as encoded by the corresponding nucleic acids as indicated in Table 1. In addition, in another embodiment the present invention relates to an anti-IL-32 antibody or IL-32 binding molecule, which competes with an antibody of the present invention as defined hereinabove for specific binding to human IL-32, preferably to IL-32γ. In particular, anti-IL-32 antibodies are provided which demonstrate the immunological binding characteristics and/or biological properties as outlined for the antibodies illustrated in the Examples and in the Figures. Where present, the term "immunological binding characteristics," or other binding characteristics of an antibody with an antigen, in all of its grammatical forms, refers to the specificity, affinity, cross-reactivity, and other binding characteristics of an antibody.

In one embodiment, the antibody of the present invention is an antibody fragment. For example, the antibody or antibody fragment of the present invention may be s elected from the group consisting of a single chain Fv fragment (scFv), an F(ab') fragment, an F(ab) fragment, an F(ab')2 fragment and a single domain antibody fragment (sdAB).

A further advantage of the antibodies of the present invention is that due to the fact that the humoral immune response has been elicited against the native antigen in its physiologic and cellular environment, typically autoantibodies are produced and can be isolated which recognize a conformational epitope of the antigen due to its presentation in context for example with other cellular components, presentation on a cell surface membrane and/or binding to a receptor. In contrast, conventional methods of generating monoclonal antibodies such as mouse monoclonals, humanized versions thereof or antibodies obtained from phage display typically employ an antigenic fragment of the target protein for immunizing an non-human mammal and detection, respectively, upon which usually antibodies are obtained which recognize linear epitopes or conformational epitopes limited to a two-dimensional structure of the immunogen rather than the presence of the native protein in its physiological and cellular context. Accordingly, it is prudent to expect that the autoantibodies of the present invention are unique in terms of their epitope specificity. Therefore, the present invention also relates to antibodies and like-binding molecules which display substantially the same binding specificity as the autoantibodies isolated in accordance with the method of the present invention. Such antibodies can be easily tested by for example competitive ELISA or more appropriately in a cell based neutralization assay using an autoantibody and a monoclonal derivative, respectively, thereof of the present invention as a reference antibody and the immunological tests described in the Examples or otherwise known to the person skilled in the art.

The present invention exemplifies IL-32 binding molecules, i.e. antibodies and binding fragments thereof which may be generally characterized by comprising in their variable region, i.e. binding domain at least one complementarity determining region (CDR) of the $V_H$ and/or $V_L$ of the variable region comprising the amino acid sequence depicted in FIG. 1 of ($V_H$) (SEQ ID NOs: 2, 10, 18 and 26) and ($V_L$) (SEQ ID NOs: 4, 12, 20 and 28)—see the exemplary CDR sequences underlined in FIG. 1 and identified in Table 1. However, as discussed in the following the person skilled in the art is well aware of the fact that in addition or alternatively CDRs may be used, which differ in their amino acid sequence from those indicated in FIG. 1 by one, two, three or even more amino acids, in particular in case of CDR2 and CDR3.

Figure 5:
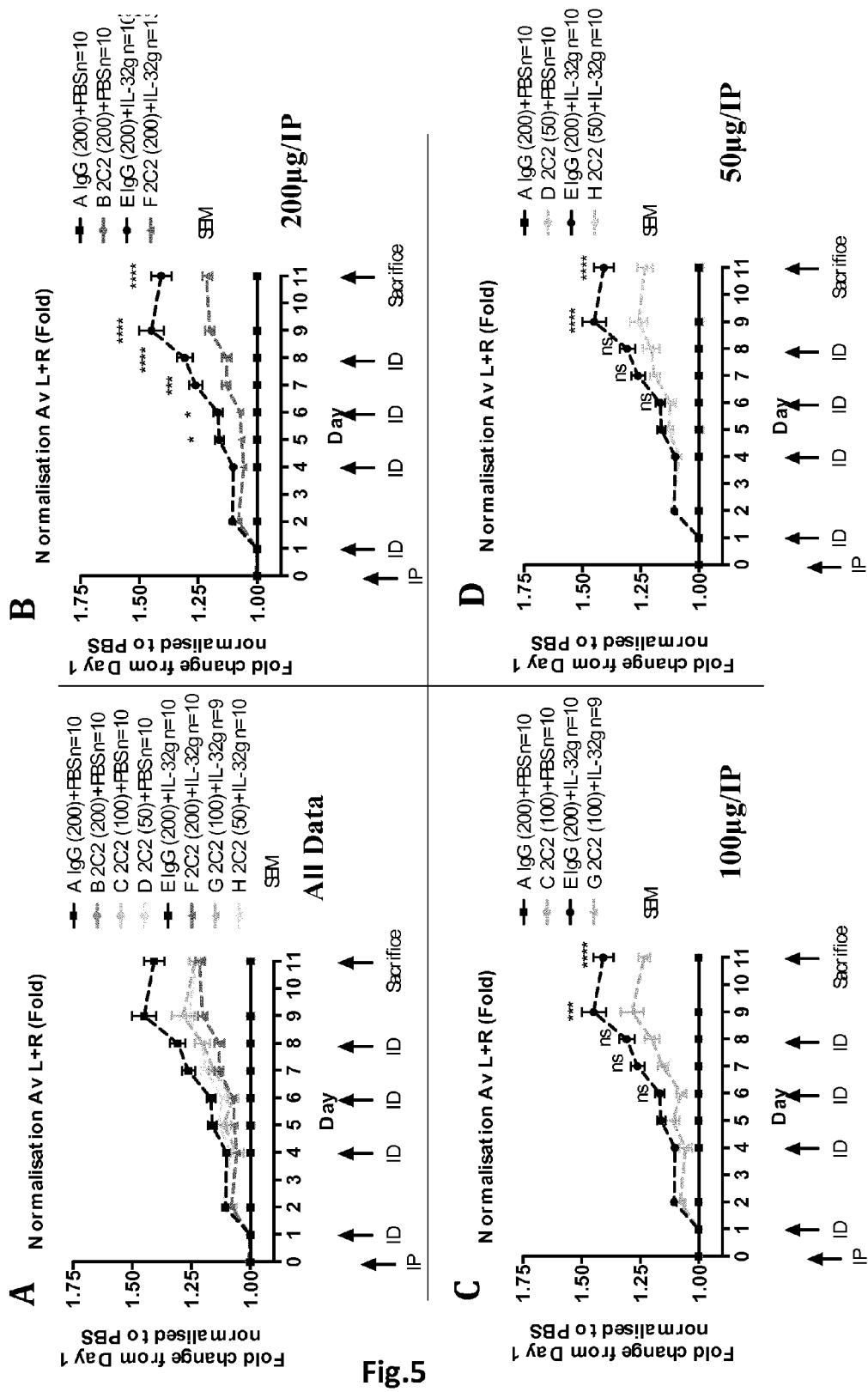
FIG. 5: CytoEar ear thickness measurements calculated as fold change relative to day 0 measurements, then normalized to relevant PBS controls, for each cohort. Mean+/−SEM, N stated on figure. P values obtained by 2-way ANOVA testing, ns (not significant)=P>0.05; *=P≤0.05; =P≤0.01; *=P≤0.001, ****=p<0.0001. IP=intraperitoneal antibody injection, ID=intradermal ear injection.
Figure 6:
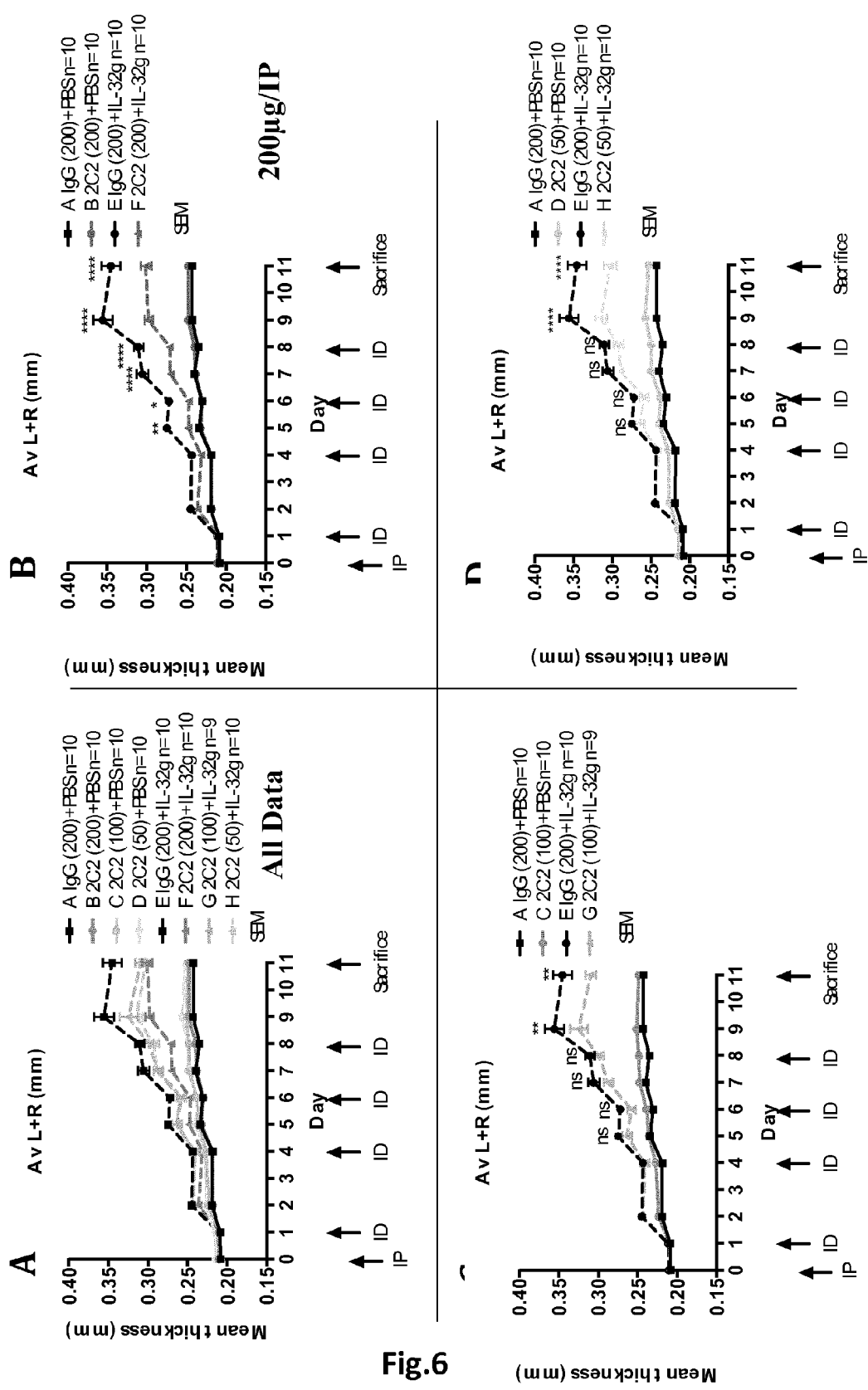
FIG. 6: CytoEar ear thickness measurements shown as absolute values (mm) for each cohort. Mean+/−SEM, N stated on figure. P values obtained by ANOVA testing. IP=intraperitoneal antibody injection, ID=intradermal ear injection. P value indications as in FIG. 5.

As has been further demonstrated for the antibodies of the present invention, they are capable of neutralizing the biological activity of their target protein; see, e.g., the results of the IL-6 neutralization assay described in Example 3, FIG. 4B and IL-32 ear inflammation assay (CytoEar assay) and ankle inflammation assay (CytoAnkle assay) described in Example 4, FIGS. 5 and 6 as well as FIGS. 9 to 12. In this context, the term "neutralizing" means that the anti-IL-32 antibody or IL-32 binding fragment thereof of the present invention is capable of intervening with the biological activity of its target protein in a biochemical, cell-based or in vivo assay as can be evaluated by performing the respective assay in the presence of the subject antibody of the present invention, wherein the biological activity of the target protein is reduced concomitantly with increasing level of the antibody of the present invention subjected to the assay compared to the biological activity of the protein without the presence of the antibody of the present invention and in the presence of a compound for example a control antibody which is known to leave the biological activity of the target protein unaffected in kind. Such biochemical, in vitro and in vivo based assay can also be performed using a reference antibody known to be capable of neutralizing the biological activity of the target protein such as has been shown for the anti-IL-32 antibodies of the present invention and subjecting the candidate antibody to the test sample, wherein either an additive neutralizing effect may be observed resulting from the combined activity of the reference and candidate antibody or a competition of the candidate antibody and reference antibody is observed which may be determined by labelling either antibody. Thus, in a preferred embodiment of the present invention, the antibody obtained by the method of the present invention is capable of neutralizing the biological activity of its antigen, e.g., at least one human IL-32 isotype, preferably of IL-32γ. The neutralizing effect may be assessed, e.g. in the terms of the amount by which the IL-32 activity is reduced or by the time, at which such a reduction can be observed after introduction of the IL-32 binding molecules of the present invention, or, of course, in the combined terms of both.

The antibodies or antigen-binding fragments, e.g., peptides, polypeptides or fusion proteins of the present invention may be provided, as indicated in detail below, by expression in a host cell or in an in vitro cell-free translation system, for example. To express the peptide, polypeptide or fusion protein in a host cell, the nucleic acid molecule encoding said peptide, polypeptide or fusion protein may be inserted into appropriate expression vector, i.e. a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (1989), and Ausubel et al., *Current Protocols in Molecular Biology* (1989); see also the sections "Polynucleotides" and "Expressions" further below and literature cited in the Examples section for further details in this respect.

A suitable host cell for expression of the product may be any prokaryotic or eukaryotic cell; e.g., bacterial cells such as *E. coli* or *B. subtilis*, insect cells (baculovirus), yeast cells, plant cell or an animal cell. For efficient processing, however, mammalian cells are preferred. Typical mammalian cell lines useful for this purpose include CHO cells, HEK 293 cells, COS cells and NSO cells.

The isolated antibodies of the present invention may of course not be applied as such to a patient, but usually have to be pharmaceutically formulated to ensure, e.g., their stability, acceptability and bioavailability in the patient. Therefore, in one embodiment, the method of the present invention is provided, further comprising the step of admixing the isolated monoclonal antibody or a fragment thereof with a pharmaceutically acceptable carrier. Pharmaceutically acceptable carriers will be described in detail further below.

As a measure to obtain a stable and permanent source of binding molecules of the present invention, heterologous genes encoding these binding molecules may be isolated by direct cloning, PCR amplification, or artificial synthesis and introduced and expressed in suitable host cells or organisms. Therefore, it is also an object of the present invention to provide a method for preparing a recombinant cell useful for the production of a recombinant human anti-IL-32 antibody or IL-32 binding fragment thereof, comprising the steps of:
(a) preparing a B-cell by a method as described above;
(b) sequencing a nucleic acid and/or obtaining from the B-cell a nucleic acid that encodes;

(i) at least one of the $C_H$ and $C_L$ amino acid sequences set forth in Table 1 (SEQ ID NOs.: 6, 8, 14, 16, 22, 24 and 30) or an amino acid sequence with at least 60% identity;

(ii) at least one complementarity determining region (CDR) of the $V_H$ and/or $V_L$ variable region amino acid sequences depicted in
FIG. 1 ($V_H$) (SEQ ID NOs: 2, 10, 18 and 26); and
FIG. 1 ($V_L$) (SEQ ID NOs: 4, 12, 20 and 28);

(iii) an amino acid sequence of the $V_H$ and/or $V_L$ region as depicted in FIG. 1;

(iv) at least one CDR consisting of an amino acid sequence resulted from a partial alteration of any one of the amino acid sequences of (a);

(v) a heavy chain and/or light variable region comprising an amino acid sequence resulted from a partial alteration of the amino acid sequence of (ii); and/or (c) inserting the nucleic acid into an expression host in order to permit expression of the antibody of interest in that host.

Host cells as described herein may be used as well in the preceding method and as described in detail in the "Host" section of this specification. In this respect, in one embodiment the above method is provided, where the expression host is a yeast cell, a plant cell or an animal cell.

In respect of the above described methods for production of the respective antibody of interest, in one embodiment the present invention provides a method, wherein the nucleic acid is manipulated between above steps (b) and (c) to introduce restriction sites, to change codon usage, and/or to add or optimize transcription and/or translation regulatory sequences.

As demonstrated in appended Examples 2 and 3 and summarized in Table 3, binding molecules, i.e. antibodies have been identified and cloned, which display a particularly high apparent binding affinity (EC50/ED50) for human IL-32. In this respect, in one embodiment of the present invention the antibody or binding fragment thereof is as defined hereinabove is provided with a high affinity for its respective target molecule, e.g., human IL-32 isotypes as defined hereinabove, preferably for IL-32γ, showing an EC50 at concentrations below 2000 ng/ml or 1500 ng/ml, preferably below 1000, 900, 800, 700, 600, 500, 400, 300, 200 or 100 ng/ml and more preferably below 50, 20 or 10 ng/ml. Alternatively or in addition, in one embodiment the antibody or antigen binding fragment thereof as defined hereinabove is provided with high neutralizing ability for a human IL-32 isotype, preferably for IL-32γ, showing IC50 at concentrations below 500 or 400 ng/ml, preferably below 300, 200 or 100 ng/ml, more preferably below 50, 20 or 10 ng/ml. For more details in respect of the binding affinity of the antibodies of the present invention see, e.g., section "Binding characteristics" further below. In one embodiment the antibody or IL-32 binding fragment of the present invention specifically binds more than one IL-32 isotype, preferably wherein IL-32γ is one of the isotypes recognized. In one embodiment, the second isotype is IL-32α. In a preferred embodiment, the anti-IL-32 antibody or IL-32 binding fragment thereof preferably binds IL-32γ over the second recognized isotype. Furthermore, in one embodiment, the anti-IL-32 antibody or IL-32 binding fragment thereof of the present invention binds one IL-32 isotype and does not or does not substantially bind any other IL-32 isotype.

The present invention also relates to polynucleotides encoding at least a variable region of an immunoglobulin chain of the antibody or antigen-binding fragment of the invention. Preferably, said variable region comprises at least one complementarity determining region (CDR) of the $V_H$ and/or $V_L$ of the variable region as set forth in FIG. 1.

In case of a derived sequence, said sequence shows at least 60% identity, more preferably (in the following order) at least 70%, at least 75%, at least 80%, at least 85%, at least 90%, and most preferably 95%, at least 96-99%, or even 100% identity to a sequence of the group consisting of those sequences referred to above and identified in the Sequence Listing. The percent identity between two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm, which is well known to those skilled in the art. The identities referred to herein are to be determined by using the BLAST programs as further referred to herein infra.

As mentioned above, in a preferred embodiment the present invention relates to substantially fully human antibodies, preferably IgG including at least the constant heavy chain I ($C_H1$) and the corresponding light chain of the constant region, i.e. γ-1, γ-2, γ-3 or γ-4 in combination with lambda or kappa. In a particularly preferred embodiment, the nucleotide and amino acid sequences of those constant regions isolated for the subject antibodies illustrated in the Examples are used as depicted in Table 1 below and in SEQ ID NOs: 5, 7, 13, 15, 21, 23 and 29 in respect of the nucleotide sequences and/or SEQ ID NOs: 6, 8, 14, 16, 22, 24 and 30 in respect of the amino acid sequences or amino acid sequences with at least 60% identity to these referenced before.

In accordance with the above, in one embodiment the present invention also provides a polynucleotide encoding at least the variable region of one immunoglobulin chain of the antibody or antigen-binding fragment of the present invention. Typically, said variable region encoded by the polynucleotide comprises at least one complementarity determining region (CDR) of the $V_H$ and/or $V_L$ of the variable region of the said antibody. Variable and constant regions of antibodies are described in more detail in the section "IgG structure" below. In a preferred embodiment of the present invention, the polynucleotide comprises, consists essentially of, or consists of a nucleic acid having a polynucleotide sequence encoding the $V_H$ or $V_L$ region of an antibody of the present invention as depicted in Table 1 below. In this respect, the person skilled in the art will readily appreciate that the polynucleotides encoding at least the variable domain of the light and/or heavy chain may encode the variable domain of either immunoglobulin chains or only one of them. In a preferred embodiment, the polynucleotide encodes the anti-IL-32 antibody or IL-32 binding fragment thereof as defined hereinabove.

TABLE 1

Nucleotide sequences of the variable and constant regions (V<sub>H</sub>, V<sub>L</sub>, C<sub>H</sub>, C<sub>L</sub>) regions of IgG3, lambda, IL-32 specific 2C2 antibody and of IgG1, lambda, IL-32 specific 14B3, 19A1 and 26A6 antibodies of the present invention. Underlined, bold nucleotides or amino acids indicate the CDR coding regions in the variable chain sequence. Underlined, italic nucleotides or amino acids indicate sequences which have not been sequenced but obtained from database. In the constant chains, such regions are aligned with and tuned in accordance with the pertinent human germ line variable region sequences in the database; see, e.g., Vbase (http://vbase.mrc-cpe.cam.ac.uk) hosted by the MRC Centre for Protein Engineering (Cambridge, UK).

| Antibody | Nucleotide and amino acid sequences of variable heavy (VH) and variable light (VL), constant heavy (CH) and constant light (CL) chains. |
|---|---|
| 2C2-V<sub>H</sub> | cagctgcgggtgcaggagtcgggcccaggactgttgaagcctgcggagacgctgtc cctcacctgcagtgtctctagtggctccgtcagcaatagtcgttattactgggcct ggatccgccagtccccagggaagggactggagtggattgggagtatgtattatcgt gggaggtcctactacaacccgtccctcaagagtcgcctcacccattttcgattgacac gtccaagaatcagttctccctgaaactgacctctctgaccgccgcagacacggccg tctattattgtgccgcagcagtttatcacgaccttgactactggggccagggaacc ctggtcaccgtctcctca SEQ ID NO: 1 |
| 2C2-V<sub>H</sub> | QLRVQESGPGLLKPAETLSLTCSVSSGSVSNSRYYWAWIRQSPGKGLEWIGSMYYR GRSYYNPSLKSRLTISIDTSKNQFSLKLTSLTAADTAVYYCAAAVYHDLDYWGQGT LVTVSS SEQ ID NO: 2 |
| 2C2-V<sub>L</sub> lambda-type | cagtctgtgttgacgcagccgccctcagtgtctgcggccccaggacagaaggtcac catctcctgctctggaagcggctccagcattgggaacaattatgtctcctggtacc agcaactcccaggagcagcccccaaactcctcatttatgacaatactaagcgaccc tcagggattcctgaccgattctctggctccaagtctggcacgtcagccaccctggc catcaccggactccaacctggggacgcggccgattattactgcggaacatgggata gtagtttcagtgttttttgggtattcggcggagggaccaagctgaccgtccta SEQ ID NO: 3 |
| 2C2-V<sub>L</sub> lambda-type | QSVLTQPPSVSAAPGQKVTISCSGSGSSIGNNYVSWYQQLPGAAPKLLIYDNTKRP SGIPDRFSGSKSGTSATLAITGLQPGDAADYYCGTWDSSFSVFWV**FGGGTKLTVL SEQ ID NO: 4 |
| 2C2-C<sub>H</sub> | gcttccaccaagggcccatcggtcttccccctggcgccctgctccaggagcacctc tggggggcacagcggccctgggctgcctggtcaaggactacttccccgaaccggtga cggtgtcgtggaactcaggcgccctgaccagcggcgtgcacaccttcccggctgtc ctacagtcctcaggactctactccctcagcagcgtggtgaccgtgccctccagcag cttgggcacccagacctacacctgcaacgtgaatcacaagcccagcaacaccaagg tggacaagagagttgagctcaaaacccccacttggtgacacaactcacacatgccca cggtgcccagagcccaaatcttgtgacacacctcccccgtgcccacggtgcccaga gcccaaatcttgtgacacacctcccccatgcccacggtgcccagagcccaaatctt gtgacacacctcccccgtgcccaaggtgcccagcacctgaactcctgggaggaccg tcagtcttcctcttcccccaaaacccaaggataccctatgatttcccggacccc tgaggtcacgtgcgtggtggtggacgtgagccacgaagaccccgaggtccagttca agtggtacgtggacggcgtggaggtgcataatgccaagacaaagtgcgggaggag cagtacaacagcacgttccgtgtggtcagcgtcctcaccgtcctgcaccaggactg gctgaacggcaaggagtacaagtgcaaggtctccaacaaagccctcccagcccca tcgagaaaaccatctccaaaaccaaaggacagccccgagaaccacaggtgtacacc ctgcccccatcccgggaggagatgaccaagaaccaggtcagcctgacctgcctggt caaaggcttctaccccagcgacatcgccgtggagtgggagagcaatgggcagccgg agaacaactacaacaccacgcctcccatgctggactccgacggctccttcttcctc tacagcaagctcaccgtggacaagagcaggtggcagcaggggaacatcttctcatg ctccgtgatgcatgaggctctgcacaaccgctacacgcagaagagcctctccctgt ctccgggtaaatga SEQ ID NO: 5 |
| 2C2-C<sub>H</sub> | ASTKGPSVFPLAPCSRSTSGGTAALGCLVKDYFPEPVTVSWNSGALTSGVHTFPAV LQSSGLYSLSSVVTVPSSSLGTQTYTCNVNHKPSNTKVDKRVELKTPLGDTTHTCP RCPEPKSCDTPPPCPRCPEPKSCDTPPPCPRCPEPKSCDTPPPCPRCPAPELLGGP SVFLFPPKPKDTLMISRTPEVTCVVVDVSHEDPEVQFKWYVDGVEVHNAKTKLREE QYNSTFRVVSVLTVLHQDWLNGKEYKCKVSNKALPAPIEKTISKTKGQPREPQVYT LPPSREEMTKNQVSLTCLVKGFYPSDIAVEWESNGQPENNYNTTPPMLDSDGSFFL YSKLTVDKSRWQQGNIFSCSVMHEALHNRYTQKSLSLSPGK SEQ ID NO: 6 |
| 2C2-C<sub>L</sub> lambda-type | agtcagcccaaggctgccccctcggtcactctgttcccgccctcctctgaggagct tcaagccaacaaggccacactggtgtgtctcataagtgacttctaccgggagccg tgacagtggcctggaaggcagatagcagccccgtcaaggcgggagtggagaccacc acaccctccaaacaaagcaacaacaagtacgcggccagcagctacctgagcctgac gcctgagcagtggaagtcccacaaaagctacagctgccaggtcaca*catgaagggagcaccgtggagaagacagtggcccctacagaatgttcatag* SEQ ID NO: 7 |

TABLE 1-continued

Nucleotide sequences of the variable and constant regions (V_H, V_L, C_H, C_L) regions of IgG3, lambda, IL-32 specific 2C2 antibody and of IgG1, lambda, IL-32 specific 14B3, 19A1 and 26A6 antibodies of the present invention. Underlined, bold nucleotides or amino acids indicate the CDR coding regions in the variable chain sequence. Underlined, italic nucleotides or amino acids indicate sequences which have not been sequenced but obtained from database. In the constant chains, such regions are aligned with and tuned in accordance with the pertinent human germ line variable region sequences in the database; see, e.g., Vbase (http://vbase.mrc-cpe.cam.ac.uk) hosted by the MRC Centre for Protein Engineering (Cambridge, UK).

| Antibody | Nucleotide and amino acid sequences of variable heavy (VH) and variable light (VL), constant heavy (CH) and constant light (CL) chains. |
|---|---|
| 2C2-C_L lambda-type | SQPKAAPSVTLFPPSSEELQANKATLVCLISDFYPGAVTVAWKADSSPVKAGVETT TPSKQSNNKYAASSYLSLTPEQWKSHKSYSCQVT*HEGSTVEKTVAPTECS* SEQ ID NO: 8 |
| 14B3-V_H | caggtgcagctggtggagtctgggggaggcgtggtccagcctggggaggtccctgag actctcctgtgtagcgtctggactcactttcaggacctatggcatgcactgggtcc gccaggctccaggcaacgggctggagtgggtggcaatcatatggcatgatggtaat aaaaaatactatgcagactccgtaaagggccgattcaccatctccagggacaattc caagaacagtctatatctccaaatgaacagcctgagagtcgaggacacggctgtgt attactgtgcgagagaaatgaatggcatcgacgtctggggccaagggaccacggtc accgtctcctca SEQ ID NO: 9 |
| 14B3-V_H | QVQLVESGGGVVQPGRSLRLSCVASGLTFRTYGMHWVRQAPGNGLEWVAIIWHDGN KKYYADSVKGRFTISRDNSKNSLYLQMNSLRVEDTAVYYCAREMNGIDVWGQGTTV TVSS SEQ ID NO: 10 |
| 14B3-V_L lambda-type | tcctatgagctgacccagccacccctcggtgtcagtgtccccaggacaaacggccag gatcacctgctctgagatgcgttgccagaaacatatgtttattggtaccagcaga gtcaggccaggccctgtgaagctcatctatgaggacagcgaacgacctccggg atccctgagagattctctggctccagctcaggggacattggccaccttgactatcag tgggggcccatgtggaggatgaagctgactactactgttactcaacagacagtagtg gtatcggggtgttcggaggagggaccaagctgaccgtccta SEQ ID NO: 11 |
| 14B3-V_L lambda-type | SYELTQPPSVSVSPGQTARITCSGDALPETYVYWYQQKSGQAPVKLIYEDSERPSG IPERFSGSSSGTLATLTISGAHVEDEADYYCYSTDSSGIGVFGGGTKLTVL SEQ ID NO: 12 |
| 14B3-C_H | gcctccaccaagggcccatcggtcttccccctggcaccctcctccaagagcacctc tggggggcacagcggccctgggctgcctggtcaaggactacttccccgaaccggtga cggtgtcgtggaactcaggcgccctgaccagcggcgtgcacaccttcccggctgtc ctacagtcctcaggactctactccctcagcagcgtggtgaccgtgccctccagcag cttgggcacccagacctacatctgcaacgtgaatcacaagcccagcaacaccaagg tggacaagagagttgagcccaaatcttgtgacaaaactcacacatgcccaccgtgc ccagcacctgaactcctggggggaccgtcagtcttcctcttccccccaaaacccaa ggacaccctcatgatctcccggacccctgaggtcacatgcgtggtggtggacgtga gccacgaagaccctgaggtcaagttcaactggtacgtggacggcgtggaggtgcat aatgccaagacaaagccgcgggaggagcagtacaacagcacgtaccgtgtggtcag cgtcctcaccgtcctgcaccaggactggctgaatggcaaggagtacaagtgcaagg tctccaacaaagcccctcccagccccatcgagaaaaccatctctcaaagccaaaggg cagccccgagaaccacaggtgtacaccctgcccccatcccgggaggagatgaccaa gaaccaggtcagcctgacctgcctggtcaaaggcttctatcccagcgacatcgccg tggagtgggagagcaatgggcagccggagaacaactacaagaccacgcctcccgtg ctggactccgacggctccttcttcctctatagcaagctcaccgtggacaagagcag gtggcagcaggggaacgtcttctcatgctccgtgatgcatgaggctctgcacaacc actacacgcagaagagcctctccctgtccccgggtaaatga SEQ ID NO: 13 |
| 14B3-C_H | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK SEQ ID NO: 14 |
| 14B3-C_L lambda-type | agtcagcccaaggctgccccctcggtcactctgttccgcccctcctctgaggagct tcaagccaacaaggccacactggtgtgtctcataagtgacttctacccgggagccg tgacagtggcctggaaggcagatagcagccccgtcaaggcgggagtggagaccacc acaccctccaaacaaagcaacaacaagtacgcggccagcagctacctgagcctgac gcctgagcagtggaagtcccacaaaagctacagctgccaggtcaca*catgaaggga gcaccgtggagaagacagtggcccctacagaatgttcatag* SEQ ID NO: 15 |

TABLE 1-continued

Nucleotide sequences of the variable and constant regions (V_H, V_L, C_H, C_L) regions of IgG3, lambda, IL-32 specific 2C2 antibody and of IgG1, lambda, IL-32 specific 14B3, 19A1 and 26A6 antibodies of the present invention. Underlined, bold nucleotides or amino acids indicate the CDR coding regions in the variable chain sequence. Underlined, italic nucleotides or amino acids indicate sequences which have not been sequenced but obtained from database. In the constant chains, such regions are aligned with and tuned in accordance with the pertinent human germ line variable region sequences in the database; see, e.g., Vbase (http://vbase.mrc-cpe.cam.ac.uk) hosted by the MRC Centre for Protein Engineering (Cambridge, UK).

| Antibody | Nucleotide and amino acid sequences of variable heavy (VH) and variable light (VL), constant heavy (CH) and constant light (CL) chains. |
|---|---|
| 14B3-C_L lambda-type | SQPKAAPSVTLFPPSSEELQANKATLVCLISDFYPGAVTVAWKADSSPVKAGVETT TPSKQSNNKYAASSYLSLTPEQWKSHKSYSCQVT*HEGSTVEKTVAPTECS* SEQ ID NO: 16 |
| 19A1-V_H | caggtgcacctggtggagtctgggggaggcgtggtccagcctggggaggtccctgag actctcctgtgtcgcgtctggactcactttcaggacctatggcatgcactgggtcc gccaggctccaggcaacgggctggagtgggtggcaattatatggcatgatggtaat aaaaaatactatgcagactccgtaaagggccgattcaccatctccagggacaattc caagaacagtctatatctccaaatgaacagcctgagagtcgaggacacggctgtgt attactgtgcgagagaaatgaatggcatcgacgtctggggccaagggaccacggtc accgtctcctca SEQ ID NO: 17 |
| 19A1-V_H | QVHLVESGGGVVQPGRSLRLSCVASGLTFRTYGMHWVRQAPGNGLEWVAIIWHDGN KKYYADSVKGRFTISRDNSKNSLYLQMNSLRVEDTAVYYCAREMNGIDVWGQGTTV TVSS SEQ ID NO: 18 |
| 19A1-V_L lambda-type | tcctatgagctgacccagccacccctcggtgtcagtgtccccaggacaaacggccag gatcacctgctctggagatgcgttgccagaaacatatgtttattggtaccagcaga gtcaggccaggcccctgtgaagctcatctatgaggacagcgaacgaccctccggg atccctgagagattctctggctccagctcaggacattggccaccttgactatcag tgggggcccatgtggaggatgaagctgactactactgttactcaacagacagtagtg gtatcggggtgttcggaggagggaccaagctgaccgtccta SEQ ID NO: 19 |
| 19A1-VL lambda-type | SYELTQPPSVSVSPGQTARITCSGDALPETYVYWYQQKSGQAPVKLIYEDSERPSG IPERFSGSSSGTLATLTISGAHVEDEADYYCYSTDSSGIGVFGGGTKLTVL SEQ ID NO: 20 |
| 19A1-C_H | gcctccaccaagggcccatcggtcttccccctggcaccctcctccaagagcacctc tggggggcacagcggccctgggctgcctggtcaaggactacttccccgaaccggtga cggtgtcgtggaactcaggcgccctgaccagcggcgtgcacaccttcccggctgtc ctacagtcctcaggactctactccctcagcagcgtggtgaccgtgccctccagcag cttgggcacccagacctacatctgcaacgtgaatcacaagcccagcaacaccaagg tggacaagagagttgagcccaaatcttgtgacaaaactcacacatgcccaccgtgc ccagcacctgaactcctggggggaccgtcagtcttcctcttccccccaaaacccaa ggacaccctcatgatctcccggacccctgaggtcacatgcgtggtggtggacgtga gccacgaagaccctgaggtcaagttcaactggtacgtggacggcgtggaggtgcat aatgccaagacaaagccgcgggaggagcagtacaacagcacgtaccgtgtggtcag cgtcctcaccgtcctgcaccaggactggctgaatggcaaggagtacaagtgcaagg tctccaacaaagcccctcccagccccatcgagaaaaccatctccaaagccaaaggg cagccccgagaaccacaggtgtacaccctgcccccatcccgggaggagatgaccaa gaaccaggtcagcctgacctgcctggtcaaaggcttctatcccagcgacatcgccg tggagtgggagagcaatgggcagccggagaacaactacaagaccacgcctcccgtg ctggactccgacggctccttcttcctctatagcaagctcaccgtggacaagagcag gtggcagcaggggaacgtcttctcatgctccgtgatgcatgaggctctgcacaacc actacacgcagaagagcctctccctgtccccgggtaaatga SEQ ID NO: 21 |
| 19A1-C_H | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPC PAPELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK SEQ ID NO: 22 |
| 19A1-C_L lambda-type | agtcagcccaaggctgccccctcggtcactctgttcccgccctcctctgaggagct tcaagccaacaaggccacactggtgtgtctcataagtgacttctacccgggagccg tgacagtggcctggaaggcagatagcagccccgtcaaggcgggagtggagaccacc acacctccaaacaaagcaacaacaagtacgcggccagcagctacctgagcctgac gcctgagcagtggaagtcccacaaaagctacagctgccaggtcaca*catgaaggga gcaccgtggagaagacagtggcccctacagaatgttcatag* SEQ ID NO: 23 |

TABLE 1-continued

Nucleotide sequences of the variable and constant regions (V$_H$, V$_L$, C$_H$, C$_L$) regions of IgG3, lambda, IL-32 specific 2C2 antibody and of IgG1, lambda, IL-32 specific 14B3, 19A1 and 26A6 antibodies of the present invention. Underlined, bold nucleotides or amino acids indicate the CDR coding regions in the variable chain sequence. Underlined, italic nucleotides or amino acids indicate sequences which have not been sequenced but obtained from database. In the constant chains, such regions are aligned with and tuned in accordance with the pertinent human germ line variable region sequences in the database; see, e.g., Vbase (http://vbase.mrc-cpe.cam.ac.uk) hosted by the MRC Centre for Protein Engineering (Cambridge, UK).

| Antibody | Nucleotide and amino acid sequences of variable heavy (VH) and variable light (VL), constant heavy (CH) and constant light (CL) chains. |
|---|---|
| 19A1-C$_L$ lambda-type | SQPKAAPSVTLFPPSSEELQANKATLVCLISDFYPGAVTVAWKADSSPVKAGVETT TPSKQSNNKYAASSYLSLTPEQWKSHKSYSCQVT*HEGSTVEKTVAPTECS* SEQ ID NO: 24 |
| 26A6-V$_H$ | caggtgcagctggtggagtctgggggaggcgtggtccagcctggggaggtccctgag actctcctgtgtagcgtctggactcactttcaggacctatggcatgcactgggtcc gccaggctccaggcaacgggctggagtgggtggcaatcatatggcatgatggtaat aaaaaatactttgctgactccgtaaagggccgattcaccatctccagggacaattc caagaacagtctatatctccaaatgaacagcctgagagtcgaggacacggctgttt attactgtgcgagagaaatgaatggcatcgacgtctggggccaagggaccacggtc accgtctcctca SEQ ID NO: 25 |
| 26A6-V$_H$ | QVQLVESGGGVVQPGRSLRLSCVASGLTFRTYGMHWVRQAPGNGLEWVAIIWHDGN KKYFADSVKGRFTISRDNSKNSLYLQMNSLRVEDTAVYYCAREMNGIDVWGQGTTV TVSS SEQ ID NO: 26 |
| 26A6-V$_L$ lambda-type | tcctatgagctgacccagccaccctcggtgtcagtgtccccaggacaaacggccag gatcacctgctctggagatgcgttgccagaaacatatgtttattggtaccagcaga agtcaggccaggcccctgtgaagctcatctatgaggacagcgaacgacctccggg atccctgagagattctctggctccagctcagggacattggccaccttgactatcag tggggcccatggaggatgaagctgactactactgttactcaacagacagtagtg gtatcggggtgttcggaggagggaccaaggtgaccgtccta SEQ ID NO: 27 |
| 26A6-V$_L$ lambda-type | SYELTQPPSVSVSPGQTARITCSGDALPETYVYWYQQKSGQAPVKLIYEDSERPSG IPERFSGSSSGTLATLTISGAHVEDEADYYCYSTDSSGIGVFGGGTKVTVL SEQ ID NO: 28 |
| 26A6-C$_L$ lambda-type | agtcagcccaaggctgcccctcggtcactctgttcccgccctcctctgaggagct tcaagccaacaaggccacactggtgtgtctcataagtgacttctacccgggagccg tgacagtggcctggaaggcagatagcagccccgtcaaggcgggagtggagaccacc acacctccaaacaaagcaacaacaagtacgcggccagcagctacctgagcctgac gcctgagcagtggaagtcccacaaaagctacagctgccaggtcaca*catgaagga gcaccgtggagaagacagtggccctacagaatgttcatag* SEQ ID NO: 29 |
| 26A6-C$_L$ lambda-type | SQPKAAPSVTLFPPSSEELQANKATLVCLISDFYPGAVTVAWKADSSPVKAGVETT TPSKQSNNKYAASSYLSLTPEQWKSHKSYSCQVT*HEGSTVEKTVAPTECS* SEQ ID NO: 30 |

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art will readily appreciate that using the variable domains or CDRs described herein antibodies can be constructed according to methods known in the art, e.g., as described in European patent applications EP 0 451 216 A1 and EP 0 549 581 A1. Furthermore, the person skilled in the art knows that binding affinity may be enhanced by making amino acid substitutions within the CDRs or within the hypervariable loops (Chothia and Lesk, *J. Mol. Biol.* 196 (1987), 901-917) which partially overlap with the CDRs as defined by Kabat. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth for V$_H$ regions in SEQ ID NOs: 2, 10, 18 and 26, and for V$_L$ regions in SEQ ID NOs: 4, 12, 20 and 28 or as indicated in FIG. 1.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. In one embodiment, the polynucleotide is a cDNA encoding the variable region and at least part of the constant domain. In a preferred embodiment a vector comprising the above polynucleotide is provided, optionally in combination with said polynucleotide which encodes the variable region of the other immunoglobulin chain of said antibody. Such vectors may comprise further genes such as marker genes which allow for the selection of said vector in a suitable host cell and under suitable conditions.

Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

In this respect, the person skilled in the art will readily appreciate that the polynucleotides encoding at least the variable domain of the light and/or heavy chain may encode the variable domains of both immunoglobulin chains or one chain only.

Likewise, said polynucleotides may be under the control of the same promoter or may be separately controlled for expression. Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GAL1 promoter in yeast or the CMV-, SV40-, RSV-promoter, CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, *Cells of Immunoglobulin Synthesis*, Academic Press, N.Y., (1979).

Furthermore, the present invention relates to vectors, particularly plasmids, cosmids, viruses and bacteriophages used conventionally in genetic engineering that comprise a polynucleotide encoding the antigen or preferably a variable domain of an immunoglobulin chain of an antibody of the invention; optionally in combination with a polynucleotide of the invention that encodes the variable domain of the other immunoglobulin chain of the antibody of the invention. Preferably, said vector is an expression vector and/or a gene transfer or targeting vector.

Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for the transformation of other cellular hosts; see Sambrook, supra.

In respect to the above, the present invention furthermore relates to a host cell comprising said polynucleotide or vector. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell; suitable host cells and methods for production of the antibodies of the present invention are described in more detail in the section "Host cells" below.

Using the above-mentioned host cells it is possible to produce and prepare an antibody of the present invention for, e.g., a pharmaceutical use or as a target for therapeutic intervention. Therefore, in one embodiment, it is also an object of the present invention to provide a method for preparing an anti-IL-32 antibody or IL-32 binding fragment thereof, said method comprising
(a) culturing the cell as defined hereinabove; and
(b) isolating said antibody or IL-32 binding fragment thereof from the culture.

Accordingly, the present invention relates to a recombinant, preferably human anti-IL-32 antibody and IL-32 binding fragment thereof, immunoglobulin chain(s) thereof encoded by the polynucleotide of the present invention or obtainable by the above-mentioned method for preparing an anti-IL-32 antibody or immunoglobulin chain(s) thereof. Means and methods for the recombinant production of antibodies and mimics thereof as well as methods of screening for competing binding molecules, which may or may not be antibodies, are known in the art. However, as described herein, in particular with respect to therapeutic applications in human the antibody of the present invention is a human antibody in the sense that application of said antibody is substantially free of an immune response directed against such antibody otherwise observed for chimeric and even humanized antibodies.

The binding molecules, antibodies or fragments thereof may be directly used as a therapeutic agent. However, in one embodiment the antibody or antigen-binding fragment which is provided by the present invention, is detectably labeled or attached to a drug, preferably wherein the detectable label is selected from the group consisting of an enzyme, a radioisotope, a fluorophore, a peptide and a heavy metal. Labeled antibodies or antigen-binding fragments of the present invention may be used to detect specific targets in vivo or in vitro including "immunochemistry/immunolabeling" like assays in vitro. In vivo they may be used in a manner similar to nuclear medicine imaging techniques to detect tissues, cells, or other material expressing the antigen of interest. Labels, their use in diagnostics and their coupling to the binding molecules of the present invention are described in more detail in section "labels and diagnostics" further below.

The antibodies of the present invention are isolated from animals or humans affected by an autoimmune disorder. On the other hand, IL-32 specific antibodies identified in the present invention may be involved in severely impairing the immune system of the affected individual, which is associated with, e.g., symptoms observed in APECED patients. Therefore, it is a further aspect of the present invention, to extinguish or at least relieve the pathological reactions of subjects suffering from autoimmune disorders by providing means and measures to minimize the number of autoantibodies and/or their effects in a diseased human patient or animal. Thus, in one embodiment the present invention also relates to a peptide or peptide-based compound comprising an epitope specifically recognized by an autoantibody of the present invention. A similar effect as by application of competitive antigens, sequestering and preventing thereby the binding of the autoantibodies to their respective targets may be obtained by anti-idiotypic antibodies, as described in detail further below. Therefore, in one embodiment the present invention also provides an anti-idiotypic antibody of an autoantibody of the present invention.

As already indicated above, the present invention also relates to the anti-idiotypic antibody or the peptide or peptide-based compound of the present invention for use in the treatment of a disorder as defined above, i.e. a disorder associated with a disrupted or deregulated genesis of self-tolerance. These isolated antibodies or fragments thereof of the present invention can be used as immunogenes to generate a panel of monoclonal anti-idiotypes. For suitable methods for the generation of anti-idiotypic antibodies see Raychadhuri et al., *J. Immunol.* 137 (1986), 1743 and for T-cells see Ertl et al., *J. Exp. Med.* 159 (1985), 1776. The anti-idiotypic antibodies will be characterized with respect to the expression of internal image and non-internal image idiotypes using standard assays routinely practiced in the art as described in detail by Raychaudhuri et al., *J. Immunol.* 137 (1986), 1743. If an anti-idiotypic antibody structurally mimics the antigen of the antibody it is binding to or bound by, it is called the "internal image" of the antigen.

Methods of providing molecules which mimic an idiotype of an autoimmune disease-associated auto-antibody (autoantibodies) are described in the art; see, e.g., international application WO03/099868, the disclosure content of which incorporated herein by reference. For example, such method may comprise the following steps: (a) providing autoantibodies in accordance with the method of the present invention; (b) binding the autoantibodies to a solid phase to form an affinity matrix; (c) contacting pooled plasma or B cells comprising immunoglobulins with the affinity matrix followed by removal of unbound plasma components; (d) eluting bound immunoglobulins, being anti-Idiotypic antibodies (anti-Id) to autoantibodies, from the matrix; (e) providing a molecular library comprising a plurality of molecule members; and (e) contacting the anti-Id with the molecular library and isolating those bound molecules which are bound by the anti-Id, the bound molecules being molecules which mimic an idiotype of autoantibodies. A method of isolating idiotypic autoantibodies in disclosed in international application WO2010/136196, the disclosure content of which incorporated herein by reference, which describes immunoglobulin preparations containing natural polyclonal IgG-reactive antibodies (Abs) isolated from normal human serum (NHS), for the treatment of autoimmune diseases and immune system disorders. The IgG-reactive Abs potently neutralize disease-associated or pathogenic autoantibodies present in sera of patients suffering from autoimmune diseases, by binding to their antigenic determinants located either within or near (e.g. overlapping with) the antigen combining sites.

The present invention also relates to compositions comprising any one of the aforementioned anti-IL32 antibodies or IL-32 binding fragments thereof, the polynucleotide, the vector, the cell, the peptide or peptide-based compound of the present invention and/or a cocktail of anti-IL32 antibodies or IL-32 binding fragments thereof which in combination display the features of anti-IL32 an antibody or IL-32 binding fragment thereof of the present invention. In addition or alternatively in one embodiment the composition or the kit of the present invention comprises the anti-idiotypic antibody of the present invention. In one embodiment the composition is a pharmaceutical composition and further comprises a pharmaceutically acceptable carrier. Pharmaceutically acceptable carriers, administration routes and dosage regimen can be taken from corresponding literature known to the person skilled in the art and are described as well in more detail in sections "Pharmaceutical carriers" and "Dosage regimen" further below.

In addition, the present invention relates to a process for the manufacture of a composition comprising the anti-IL-32 monoclonal antibody or a IL-32 binding fragment or biotechnological derivative thereof, which manufacture comprises the step of preparation of the antibody, IL-32 binding fragment or biotechnological derivative thereof by expression in a recombinant host organism of transforming DNA encoding the antibody, a IL-32 binding fragment or biotechnological derivative thereof. In one embodiment, the composition is a pharmaceutical composition, wherein the step of preparation of the antibody, IL-32 binding fragment or biotechnological derivative thereof is followed, optionally after one or more steps in between by admixing the antibody, IL-32 binding fragment or biotechnological derivative thereof with a pharmaceutically acceptable carrier in the manufacture of a pharmaceutical composition. For example, before formulating in the pharmaceutical composition, the antibody or IL-32 binding fragment thereof may be purified from the cell culture to pharmaceutical grade and/or derivatized, for example pegylated or conjugated to a diagnostic label or drug so as obtain the pharmaceutical composition.

Besides biochemical and cell based in vitro assays therapeutic utility of the antibodies of the present invention can be validated in appropriate animal models as described in detail in the Examples section further below.

In one embodiment the pharmaceutical composition further comprises an additional agent useful for treating an inflammation or an autoimmune disorder, preferably wherein said agent is selected from the group consisting of Non-Steroidal Antiinflammatory Drugs (NSAIDs), Corticosteroids, Anti-Histamines and combinations thereof. In addition or alternatively, in a further embodiment the pharmaceutical composition further comprises an additional agent useful for treating an inflammation related disease, selected from the group consisting of immunosuppressive and anti-inflammatory or "anti-rheumatic" drugs.

In another embodiment, the composition is a diagnostic composition or kit and further comprises reagents conventionally used in immuno- or nucleic acid based diagnostic methods.

Furthermore, the present invention provides the aforementioned anti-IL-32 antibody or IL-32 binding fragment thereof, or the composition as defined hereinabove for use in a method of:
(a) treating or preventing the progression of an immune mediated or autoimmune disease or condition;
(b) amelioration of symptoms associated with an immune mediated or autoimmune disease or condition; and/or
(c) diagnosing or screening a subject for the presence or for determining a subject's risk for developing an immune mediated or autoimmune disease or condition;
wherein the disorder is associated with the expression of IL-32, elevated and/or detrimental IL-32 activity in a patient.

In this respect, several application routes may be used. In one embodiment of the present invention the aforementioned antibody or antigen-binding fragment, the anti-idiotypic antibody or peptide or peptide-based compound and/or a cocktail of antibodies which in combination display the features of an antibody of the present invention is provided, which is designed to be administered intravenously, intramuscularly, subcutaneously, intraperitoneally, intranasally, parenterally or as an aerosol.

As indicated above, due to their binding specificity, the molecules of the present invention such as antibodies and fragments thereof may preferably be used in the above defined method of treatment, amelioration, diagnosing and/or screening of an immune mediated or autoimmune disorder or condition associated with and/or caused by expression of IL-32, elevated and/or detrimental activity of IL-32. For example, expression, elevated and/or detrimental IL-32 activity has been observed in rheumatoid arthritis (RA) synovial tissue biopsies, wherein the level of IL-32 expression correlated positively with the severity of inflammation (Alsaleh et al., (2010), supra; Cagnard et al., (2005), supra). Besides rheumatoid arthritis (RA), IL-32 was found functionally associated with several other disorders, e.g., ankylosing spondylitis (Ciccia et al., (2012), supra), inflammatory bowel disease (IBD), Myasthenia gravis (MG), chronic obstructive pulmonary disease (COPD), Asthma, Crohn's disease, psoriasis, Vascular inflammation & atherosclerosis (Kobayashi et al., (2010)), atopic dermatitis and cancer (Alsaleh et al., (2010); Breenan and Beech, (2007); Asquith and McInnes (2007); Dinarello and Kim, (2006); Fantini et al., (2007; all supra). IL-32 may also play a role in immune responses to tuberculosis (Kundu and Basu, (2006); Netea et al., (2006); supra). Also, increased transcription of IL-32 has been observed after infection by bacteria and viruses, such as *Mycobacterium tuberculosis* (Netea et al., (2006), supra) or Influenza A (Li at al., (2008), supra) indicating its possible role in host defense.

Therefore, in one embodiment the anti-IL-32 antibody or IL-32 binding fragment thereof or the composition as defined hereinabove for use in the above-mentioned method is provided, wherein said disease is an autoimmune disease, preferably selected from the group consisting of rheumatoid arthritis (RA), ankylosing spondylitis and other forms of spondyloarthritis including but not limited to psoriatic arthritis, inflammatory bowel disease (IBD; including Crohn's disease, ulcerative colitis and Celiac's disease), psoriasis, myasthenia gravis (MG), chronic obstructive pulmonary disease (COPD), asthma, tuberculosis, vascular inflammation and atherosclerosis, atopic dermatitis, tuberculosis and cancer including leukemia.

Due to the multitude of molecules suitable in treatment of, e.g., disorders associated with inflammation presented herein, the present invention also relates to methods of treatment, diagnosing and/or prognosticate the probable course and outcome of such disorders, preferably wherein the immune mediated or autoimmune disease or condition is associated with the expression, elevated and/or detrimental activity of IL-32 and to the use of the molecules of the present invention. In one embodiment a method for treating of such a disorder is provided, which method comprises administering to a subject in need thereof a therapeutically effective amount of the aforementioned antibody or antigen-binding fragment, the cocktail of antibodies which in combination display the features of an antibody of the present invention, the anti-idiotypic antibody or the peptide or peptide-based compound.

Furthermore, in one embodiment the present invention relates to a method of treating an immune mediated or autoimmune disease or condition associated with the expression, elevated and/or detrimental activity of IL-32 comprising administering to a subject a therapeutically effective amount of a ligand binding molecule comprising:
(i) at least one CDR of the anti-IL-32 antibody or IL-32 binding fragment thereof of the present invention; or
(ii) at least one anti-idiotypic antibody and/or peptide or peptide-based compound as defined hereinabove.

Treatment methods based on the use of only one monoclonal antibody specific for an epitope of a particular antigen, which is related or causing a disease may suffer from several shortcomings. For example, difficulties and probably inefficiency of treatment may stem from the multiplicity of the pathogenic mechanisms causing a specific disorder requiring targeting of several antigens simultaneously. Furthermore, the inherent diversity of the patient population has to be taken into account concerning, e.g., polymorphism, heterogeneity of glycosylation or slight denaturation of a given antigen, either in different or in one patient which may lead to a decreased binding efficiency of the monoclonal antibody used at least. Some of these shortcomings may be circumvented by, e.g., pretreatment screenings to determine whether the antigen is immunologically relevant to the patients intended to be treated and whether there are any epitope changes in the particular patients. However, such screenings are often omitted either due to treatment urgency or to cost restraints. Therefore, the present invention further relates to methods based on the application of more than one type of a binding molecule at once to a patient, i.e. to the application of a cocktail of binding molecules. These binding molecules may specifically bind to one IL-32 isotype at different epitopes, each of the binding molecules applied may bind specifically another IL-32 isotype or several binding molecules are used binding to several epitopes of more than one IL-32 isotype. In case the binding molecules of the present invention are directed (bind specifically) towards one IL-32 isotype as antigen, their binding specificity is directed towards distinct epitopes of said antigen. The use of such cocktails is in particular envisaged for the treatment of patients suffering from autoimmune disorders such as APS1, who in view of the presence of autoantibodies against about 3000 endogenous antigens are often not amenable to monotherapy with one particular antibody. In such cases, combination therapy with two or more monoclonal antibodies and/or peptides and peptide-based compounds of the present invention with the same or different antigen specificity are expected to achieve at least some relief of the symptoms.

Therefore, in one embodiment a further method of treating a disorder is provided comprising administering to a subject a therapeutically effective amount of a cocktail consisting essentially of at least two, three, four, five and more components selected from the groups consisting of:
- an antibody or antigen-binding fragment thereof of the present invention specifically binding the IL-32 isotype as defined hereinabove; and/or
- an anti-idiotypic antibody of the present invention, and/or from a peptide or peptide-based compound of the present invention, which peptide or peptide-based compound comprises an epitope specifically recognized by an antibody or antigen-binding fragment thereof of the present invention.

The present invention naturally extents also to diagnostic and prognostic methods directed towards diagnosing immune mediated or autoimmune conditions and disorders associated with expression, elevated and/or detrimental activity of one or more isotypes of IL-32, preferably of IL-32γ and/or prognosis of the development of the disease, i.e. its progression, response to treatment or recovery. Therefore, in one embodiment the present invention relates to a method of diagnosing an immune mediated or autoimmune disease or condition in a subject associated with the expression, elevated and/or detrimental activity of IL-32 comprising contacting a biological sample of the subject with an anti-IL-32 antibody or IL-32 binding fragment thereof of the present invention, and detecting the presence of IL-32. In a preferred embodiment, the detected IL-32 isotype is IL-32γ. Furthermore, in one embodiment the present invention relates to a method of detecting or determining IL-32 in an isolated biological sample comprising admixing the sample with an anti-IL-32 antibody of the present invention, allowing the antibody to form a complex with any IL-32 isotype present in the mixture, and detecting the complex present in the mixture, preferably wherein IL-32 is IL-32γ.

As already mentioned above, in one embodiment the present invention relates to a kit for the diagnosis of an immune mediated or autoimmune disease or condition associated with the expression of IL-32, said kit comprising the aforementioned antibody or antigen-binding fragment, the anti-idiotypic antibody or the peptide or peptide-based compound, the polynucleotide, the vector or the cell, optionally with reagents and/or instructions for use. Associated with the kits of the present invention, e.g., within a container comprising the kit can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The compositions, i.e. kits of the present invention are of course particularly suitable for the diagnosis, prevention and treatment of a disorder or condition which is accompanied with the expression of IL-32, in particular applicable for the treatment of diseases as mentioned above. In a particularly preferred embodiment the disorder is associated with expression of one or more of IL-32 isotypes.

In another embodiment the present invention relates to a diagnostic composition comprising any one of the above described binding molecules, antibodies, antigen-binding fragments, peptides or peptide-based compounds, polynucleotides, vectors or cells of the invention and optionally suitable means for detection such as reagents conventionally used in immune- or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

In this context, the present invention also relates to means specifically designed for this purpose. For example, a protein- or antibody-based array may be used, which is for example loaded with either antigens derived from one or more IL-32 isotypes and containing the disease-associated antigen in order to detect autoantibodies which may be present in patients suffering from an autoimmune diseases, in particular RA, IBD or APECED/APS1, or with antibodies or equivalent antigen-binding molecules of the present invention which specifically recognize any one of those inflammation-associated antigens. Design of microarray immunoassays is summarized in Kusnezow et al., *Mol. Cell Proteomics* 5 (2006), 1681-1696. Accordingly, the present invention also relates to microarrays loaded with binding molecules or antigens identified in accordance with the present invention.

DEFINITIONS AND EMBODIMENTS

Unless otherwise stated, a term and an embodiment as used herein is given the definition as provided and used in international application WO 2013/098419 A1 and WO 2013/098420 A1. Supplementary, a common term as used herein is given the definition as provided in the *Oxford Dictionary of Biochemistry and Molecular Biology*, Oxford University Press, 1997, revised 2000 and reprinted 2003, ISBN 0 19 850673 2.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

The term "neutralizing" and "neutralizing antibody", respectively, is used as common in the art in that an antibody is meant that reduces or abolishes at least some biological activity of an antigen or of a living microorganism. For example, a isotype-specific anti-IL-32 antibody of the present invention is a neutralizing antibody, if, in adequate amounts, it abolishes or reduces the activity of the respective IL-32 isotype(s) for example in an assay as described in the Examples. Neutralization is commonly defined by 50% inhibitory concentrations (IC 50) and can be statistically assessed based on the area under the neutralization titration curves (AUC). IC 50 values of exemplary anti-IL-32 antibodies of the present invention are described and shown herein, e.g., exemplary antibody 2C2 has an IL-32γ IC 50 value of 300 ng/ml.

Central and Peripheral Tolerance

Self-tolerance is the process whereby the immune system does not respond to an antigen that is a constituent of that organism. Self-tolerance is achieved by death or inactivation of self-reactive T and B-cells, which may occur as part of central tolerance in a central (generative) immune organ (thymus or bone marrow) or as peripheral tolerance in what are most commonly regarded as secondary immune tissues (e.g. spleen, lymph node, intestine). Self-tolerance is a central feature of the normal immune system. Failure to establish and/or maintain self-tolerance leads to autoimmunity, which may result in autoimmune diseases that have severe health implications for the host organism.

T- and B-cells can develop central tolerance towards those antigens that are present in generative immune organs. In the bone marrow, B cells develop tolerance to ubiquitously expressed, bone-marrow specific antigens and to antigens imported by the blood circulation. In the thymus, thymic medullary epithelial cells can express many hundreds of self-antigens that are presented to developing T-cells. The gene responsible for the broad expression of self-antigens in thymic medullary epithelial cells is AIRE (autoimmune regulator). AIRE activates multiple tissue specific genes that normally are expressed only in particular peripheral organs such as insulin in pancreatic Langerhans islands. In the absence of the functional AIRE gene, antigens are not presented, T cells are not inactivated, and autoimmunity to self-antigens develops, leading to pathology in APECED patients and in Aire deficient mice.

Another important gene in the induction of tolerance is foxp3. This encodes a transcription factor that induces a immunosuppressive, regulatory fate in T lymphocytes that engage self-antigen in the thymus, and possibly also in the periphery. Failure to encode a functional FOXP3 protein is a characteristic of IPEX patients that as a consequence, also suffer widespread autoimmune disease.

Central and peripheral tolerance are described in more detail in the respective chapter of international application WO 2013/098419 A1 on pages 62-63, the disclosure content of which is incorporated herein by reference.

Peptides and Polypeptides:

The term "peptide" is understood to include the terms "polypeptide" and "protein" (which, at times, may be used interchangeably herein) and any amino acid sequence such as those of the heavy and light chain variable region as well as constant region of the present invention within its meaning. Similarly, fragments of proteins and polypeptides are also contemplated and may be referred to herein as "peptides". Nevertheless, the term "peptide" preferably denotes an amino acid polymer including at least 5 contiguous amino acids, preferably at least 10 contiguous amino acids, more preferably at least 15 contiguous amino acids, still more preferably at least 20 contiguous amino acids, and particularly preferred at least 25 contiguous amino acids. In addition, the peptide in accordance with present invention typically has no more than 100 contiguous amino acids, preferably less than 80 contiguous amino acids and more preferably less than 50 contiguous amino acids.

As used herein, the term "polypeptide" is intended to encompass a singular "polypeptide" as well as plural "polypeptides" such as antibodies of the present invention, and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Nevertheless, the term "polypeptide" preferably denotes an amino acid polymer including at least 100 amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan. Proteins or polypeptides expressed in yeast may have a glycosylation pattern different from that expressed in mammalian cells.

Also included as polypeptides of the present invention are fragments, derivatives, analogs and variants of the foregoing polypeptides and any combination thereof. The terms "fragment," "variant," "derivative" and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the preferred peptides of the present invention, in particular to antibodies or antibody fragments, or to synthetic peptide or peptide-based compound comprising epitopes recognized by the antibodies of the present invention or fragments, variants, derivatives or analogs of either of them. Such variants generally retain the functional activity of the peptides of the present invention, i.e. are bound by the antibodies of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of binding molecules of the present invention, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Anti-Idiotypic Antibodies:

The term "anti-idiotypic antibodies" when referring to antibodies or other binding molecules includes molecules which bind to the unique antigenic peptide sequence located on an antibody's variable region near or at the antigen binding site, inhibiting by this a specific immune response by otherwise caused by the given auto-antibody. In an analogous manner synthetic peptide or peptide-based compound comprising an epitope specifically recognized by an antibody of the present invention may be used.

Anti-idiotypic antibodies may be obtained in a similar fashion as other antibodies. The particular anti-idiotypic antibody is detected by any sort of cross-linking, either by agglutination (in turbidimetric or nephelometric assays), precipitation (radial immunodiffusion), or sandwich immunoassays such as ELISAs. U.S. patent application No. 20020142356 provides a method for obtaining anti-idiotypic monoclonal antibody populations directed to an antibody that is specific for a high-concentration, high-molecular-weight target antigen wherein said anti-idiotypic antibody populations have a wide range of binding affinities for the selected antibody specific to said target antigen and wherein a subset of said anti-idiotypic antibody populations can be selected having the required affinity for a particular application.

U.S. patent application No. 20020142356 describes a competitive immunoassay of an antigen using an antibody as coat and an anti-idiotypic antibody as detection or vice-versa. Other references disclosing use of an anti-idiotypic antibody as a surrogate antigen include Losman et al., Cancer Research, 55 (1995) (23 suppl. S):S5978-S5982; Becker et al., J. of Immunol. Methods 192 (1996), 73-85; Baral et al., International J. of Cancer, 92 (2001), 88-95; and Kohen et al., Food and Agriculture Immunology, 12 (2000), 193-201. Use of anti-idiotypic antibodies in treatment of diseases or against parasites is known in the art; see, e.g., in Sacks et al., J. Exper. Medicine, 155 (1982), 1108-1119.

Determination of Similarity and/or Identity of Molecules:

"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

The determination of percent identity or similarity between two sequences is preferably accomplished using the mathematical algorithm of Karlin and Altschul (1993) Proc. Natl. Acad. Sci USA 90: 5873-5877. Such an algorithm is incorporated into the BLASTn and BLASTp programs of Altschul et al. (1990) J. Mol. Biol. 215: 403-410 available at NCBI (http://www.ncbi.nlm.nih.gov/blast/Blast.cge).

The determination of percent identity or similarity is performed with the standard parameters of the BLASTn and BLASTp programs.

BLAST polynucleotide searches are performed with the BLASTn program.

For the general parameters, the "Max Target Sequences" box may be set to 100, the "Short queries" box may be ticked, the "Expect threshold" box may be set to 10 and the "Word Size" box may be set to 28. For the scoring parameters, the "Match/mismatch Scores" may be set to 1, −2 and the "Gap Costs" box may be set to linear. For the Filters and Masking parameters, the "Low complexity regions" box may not be ticked, the "Species-specific repeats" box may not be ticked, the "Mask for lookup table only" box may be ticked, and the "Mask lower case letters" box may not be ticked.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or not fused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA), small hairpin RNA (shRNA), small interfering RNA (siRNA) or any other RNA product.

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse ß-glucuronidase. However, intracellular production of the polypeptides, in particular of the immunoglobulins and fragments thereof of the present invention is also possible.

Expression:

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., small interfering RNA (siRNA), a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

To express the peptide, polypeptide or fusion protein (hereinafter referred to as "product") in a host cell, a procedure such as the following can be used. A restriction fragment containing a DNA sequence that encodes said product may be cloned into an appropriate recombinant plasmid containing an origin of replication that functions in the host cell and an appropriate selectable marker. The plasmid may include a promoter for inducible expression of the product (e.g., pTrc (Amann et al, Gene 69 (1988), 301 315) and pET1 Id (Studier et al., *Gene Expression Technology: Methods in Enzymology* 185, Academic Press, San Diego, Calif. (1990), 60 89). The recombinant plasmid may be introduced into the host cell by, for example, electroporation and cells containing the recombinant plasmid may be identified by selection for the marker on the plasmid. Expression of the product may be induced and detected in the host cell using an assay specific for the product.

In some embodiments, the DNA that encodes the product/peptide may be optimized for expression in the host cell. For example, the DNA may include codons for one or more amino acids that are predominant in the host cell relative to other codons for the same amino acid. Alternatively, the expression of the product may be performed by in vitro synthesis of the protein in cell-free extracts which are also particularly suited for the incorporation of modified or unnatural amino acids for functional studies; see also infra. The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases. The most frequently used cell-free translation systems consist of extracts from rabbit reticulocytes, wheat germ and *Escherichia coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract must be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors known in the art ($Mg^{2+}$, $K^+$, etc.). Appropriate transcription/translation systems are commercially available, for example from Promega Corporation, Roche Diagnostics, and Ambion, i.e. Applied Biosystems (Anderson, C. et al., *Meth. Enzymol.* 101 (1983), 635-644; Arduengo, M. et al. (2007), *The Role of Cell-Free Rabbit Reticulocyte Expression Systems in Functional Proteomics* in, Kudlicki, Katzen and Bennett eds., *Cell-Free Expression* Vol. 2007. Austin, Tx: *Landes Bioscience*, pp. 1-18; Chen and Zubay, *Meth. Enzymol.* 101 (1983), 674-90; Ezure et al., *Biotechnol. Prog.* 22 (2006), 1570-1577).

Host Cells:

In respect of the present invention, host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably HEK 293, NSO, CSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, *Molecular Cloning: A Laboratory Manual*, Cold Spring Harbor Laboratory, Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "*Protein Purification*", Springer Verlag, N.Y. (1982). The antibody or its corresponding immunoglobulin chain(s) of the invention can then be isolated from the growth medium, cellular lysates, or cellular membrane fractions. The isolation and purification of the, e.g., recombinantly expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.

ELISA-Assays:

Enzyme-linked immunosorbent assays (ELISAs) for various antigens include those based on colorimetry, chemiluminescence, and fluorometry. ELISAs have been successfully applied in the determination of low amounts of drugs and other antigenic components in plasma and urine samples, involve no extraction steps, and are simple to carry out. ELISAs for the detection of antibodies to protein antigens often use direct binding of short synthetic peptides to the plastic surface of a microtitre plate. The peptides are, in general, very pure due to their synthetic nature and efficient purification methods using high-performance liquid chromatography. A drawback of short peptides is that they usually represent linear, but not conformational or discontinuous epitopes. To present conformational epitopes, either long peptides or the complete native protein is used. Direct binding of the protein antigens to the hydrophobic polystyrene support of the plate can result in partial or total denaturation of the bound protein and loss of conformational epitopes. Coating the plate with an antibody, which mediates the immobilization (capture ELISA) of the antigens, can avoid this effect.

However, frequently, overexpressed recombinant proteins are insoluble and require purification under denaturing conditions and renaturation, when antibodies to conformational epitopes are to be analyzed. See, for example, U.S. patent application No. 20030044870 for a generic ELISA using recombinant fusion proteins as coat proteins.

Binding Molecules:

A "binding molecule" as used in the context of the present invention relates primarily to antibodies, and fragments thereof, but may also refer to other non-antibody molecules that bind to the "molecules of interest" of the present invention, wherein the molecules of interest are proteins of the class of glycoproteins known as cytokines, in particular interleukines selected from the group of different IL-32 isotypes. In a particularly preferred embodiment, the molecule of interest is IL-32γ. The molecules of interest of the present invention are defined in further detail within the description of the particular embodiments of the present invention above and below. The binding molecules of the present invention include but are not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

Antibodies:

The terms "antibody" and "immunoglobulin" are used interchangeably herein. An antibody or immunoglobulin is a molecule binding to a molecule of interest of the present invention as defined hereinabove and below, which comprises at least the variable domain of a heavy chain, and normally comprises at least the variable domains of a heavy chain and a light chain. Basic immunoglobulin structures in vertebrate systems are relatively well understood; see, e.g., Harlow and Lane, Antibodies: A Laboratory Manual, (Cold Spring Harbor Laboratory Press, 2nd ed. 1988). The terms "binds" and "recognizes" are used interchangeably in respect of the binding affinity of the binding molecules of the present invention, e.g., antibodies.

Any antibody or immunoglobulin fragment which contains sufficient structure to specifically bind to the molecules of interest, as defined hereinabove and below, is denoted herein interchangeably as a "binding molecule", "binding fragment" or an "immunospecific fragment."

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No.

5,892,019. In this respect, antigen-binding fragment of the antibody can be as well domain antibodies (dAb) also known as single domain antibodies (sdAB) or Nanobodies™ (Ablynx, Gent, Belgium), see, e.g., De Haard et al., *J. Bacteriol.* 187 (2005), 4531-4541; Holt et al., *Trends Biotechnol.* 21 (2003), 484-490. As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgE, IgM, IgD, IgA, and IgY, respectively. The immunoglobulin subclasses (isotypes) e.g., IgG1, IgG2, IgG3, IgG4, IgA1, etc. are well characterized and are known to confer functional specialization. Immunoglobulin or antibody molecules of the invention can be of any type (e.g., IgG, IgE, IgM, IgD, IgA, and IgY), class (e.g., IgG1, IgG2, IgG3, IgG4, IgA1, IgA2, etc.) or subclass of immunoglobulin molecule. Modified versions of each of these classes and isotypes are readily discernable to the skilled artisan in view of the instant disclosure and, accordingly, are within the scope of the instant invention. Although all immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

As evident from the classification of the exemplary anti-IL-32 antibodies of the present invention enlisted in Table 1 above, the exemplary antibodies of the present invention are of the IgG3 or IgG1 class, possibly implicating regulatory T-cell responses and/or epithelia in their initiation in these AIRE-deficiency states. These findings are confirmed by the classification of corresponding autoantibodies found in the AIRE-deficient mice described by Kärner et al., in Clin. Exp. Immunol. (2012); doi: 10.1111/cei.12024, the disclosure content of which is incorporated herein by reference. Accordingly, in a preferred embodiment of the present invention, the antibodies of the present invention are of the IgG type, even more preferred IgG3 or IgG1.

IgG Structure:

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to a molecule of interest of the present invention is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., *U.S. Department of Health and Human Services,* (1983); and Chothia and Lesk, *J. Mol. Biol.* 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., *U.S. Dept. of Health and Human Services,* "Sequences of Proteins of Immunological Interest" (1983) and by Chothia and Lesk, *J. Mol. Biol.* 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 2 as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 2

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 2 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particularly preferred embodiment, the antibody of the present invention is not a polyclonal antibody, i.e. it substantially consists of one particular antibody species rather than being a mixture obtained from a plasma immunoglobulin sample.

Antibody Fragments, Animalization:

Antibody fragments, including single-chain antibodies, may comprise the variable region(s) alone or in combination with the entirety or a portion of the following: hinge region, CH1, CH2, and CH3 domains. Also included in the invention are fragments binding to a molecule of interest of the present invention, said fragments comprising any combination of variable region(s) with a hinge region, CH1, CH2, and CH3 domains. Antibodies or immunospecific fragments thereof of the present invention equivalent to the monoclonal antibodies isolated in accordance with the method of the present invention, in particular to the human monoclonal antibodies may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In a particularly preferred embodiment of the present invention, the antibodies are naturally occurring human monoclonal antibodies or binding fragments, derivatives and variants thereof cloned from human subjects, which bind specifically to specific IL-32 isotypes of the present invention, preferably to IL-32γ, as defined in detail above and below, e.g., in Table 1, the Figures, in particular FIGS. 1 to 4 and in the Examples, e.g., in Examples 2 and 6.

Optionally, the framework region of the human antibody is aligned and adopted in accordance with the pertinent human germ line variable region sequences in the database; see, e.g., Vbase (http://vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural IL-32 isotypes in their relevant conformation in the human body, (ii) having protected the individual from or minimized at least significant the presence of symptoms of a disease, e.g., SLE, and (iii) since the antibody is of human origin the risks of cross-reactivity against self-antigens is minimized. Thus, in accordance with the present invention the terms "human monoclonal antibody", "human monoclonal autoantibody", "human antibody" and the like are used to denote a IL-32 binding molecule of a particular IL-32 isotype specificity which is of human origin, i.e. which has been isolated from a human cell such as a B cell or hybridoma thereof or the cDNA of which has been directly cloned from mRNA of a human cell, for example a human memory B cell. A human antibody is still considered as "human" even if amino acid substitutions are made in the antibody, e.g., to improve its binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility.

Grafted Antibodies (Equivalents)

The invention also relates to grafted antibodies (interchangeably referred to as equivalents) containing CDRs derived from the antibodies of the present invention, such as IL-32 antibodies, respectively. Such grafted CDRs include animalized antibodies, in which CDRs from the antibodies of the present invention have been grafted or in which a CDR containing one or more amino acid substitutions is grafted. The CDRs can be grafted directly into a human framework or an antibody framework from animal origin as indicated above. If desired, framework changes can also be incorporated by generating framework libraries. The optimization of CDRs and/or framework sequences can be performed independently and sequentially combined or can be performed simultaneously, as described in more detail below.

To generate grafted antibodies donor CDRs of the antibodies of the present invention are grafted onto an antibody acceptor variable region framework. Methods for grafting antibodies and generating CDR variants to optimize activity have been described previously (see, e.g., international patent applications WO 98/33919; WO 00/78815; WO 01/27160). The procedure can be performed to achieve grafting of donor CDRs and affinity reacquisition in a simultaneous process. The methods similarly can be used, either alone or in combination with CDR grafting, to modify or optimize the binding affinity of a variable region. The methods for conferring donor CDR binding affinity onto an acceptor variable region are applicable to both heavy and light chain variable regions and as such can be used to simultaneously graft and optimize the binding affinity of an antibody variable region.

The donor CDRs can be altered to contain a plurality of different amino acid residue changes at all or selected positions within the donor CDRs. For example, random or biased incorporation of the twenty naturally occurring amino acid residues, or preselected subsets, can be introduced into the donor CDRs to produce a diverse population of CDR species. Inclusion of CDR variant species into the diverse population of variable regions allows for the generation of variant species that exhibit optimized binding affinity for a predetermined antigen. A range of possible changes can be made in the donor CDR positions. Some or all of the possible changes that can be selected for change can be introduced into the population of grafted donor CDRs. A single position in a CDR can be selected to introduce changes or a variety of positions having altered amino acids can be combined and screened for activity.

One approach is to change all amino acid positions along a CDR by replacement at each position with, for example, all twenty naturally occurring amino acids. The replacement of each position can occur in the context of other donor CDR amino acid positions so that a significant portion of the CDR maintains the authentic donor CDR sequence, and therefore, the binding affinity of the donor CDR. For example, an acceptor variable region framework, either a native or altered framework, can be grafted with a population of CDRs containing single position replacements at each position within the CDRs. Similarly, an acceptor variable region framework can be targeted for grafting with a population of CDRs containing more than one position changed to incorporate all twenty amino acid residues, or a subset of amino acids. One or more amino acid positions within a CDR, or within a group of CDRs to be grafted, can be altered and grafted into an acceptor variable region framework to generate a population of grafted antibodies. It is understood that a CDR having one or more altered positions can be combined with one or more other CDRs having one or more altered positions, if desired.

A population of CDR variant species having one or more altered positions can be combined with any or all of the CDRs which constitute the binding pocket of a variable region. Therefore, an acceptor variable region framework can be targeted for the simultaneous incorporation of donor CDR variant populations at one, two or all three recipient CDR locations in a heavy or light chain. The choice of which CDR or the number of CDRs to target with amino acid position changes will depend on, for example, if a full CDR grafting into an acceptor is desired or whether the method is being performed for optimization of binding affinity.

Another approach for selecting donor CDR amino acids to change for conferring donor CDR binding affinity onto an antibody acceptor variable region framework is to select known or readily identifiable CDR positions that are highly variable. For example, the variable region CDR3 is generally highly variable. This region therefore can be selectively targeted for amino acid position changes during grafting procedures to ensure binding affinity reacquisition or augmentation, either alone or together with relevant acceptor variable framework changes.

Murinized Antibodies:

An example of antibodies generated by grafting, as described above, are murinized antibodies. As used herein, the term "murinized antibody" or "murinized immunoglobulin" refers to an antibody comprising one or more CDRs from a human antibody of the present invention; and a human framework region that contains amino acid substitutions and/or deletions and/or insertions that are based on a mouse antibody sequence. The human immunoglobulin providing the CDRs is called the "parent" or "acceptor" and the mouse antibody providing the framework changes is called the "donor". Constant regions need not be present, but if they are, they are usually substantially identical to mouse antibody constant regions, i.e. at least about 85-90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody.

Antibody Fragments:

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimere are identical to those on a second polypeptide chain of the multimere. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

Thus, as also exemplified in the Examples, in one embodiment the constant region of the antibody of the present invention or part thereof, in particular the CH2 and/or CH3 domain but optionally also the CH1 domain is heterologous to the variable region of the native human monoclonal antibody isolated in accordance with the method of the present invention. In this context, the heterologous constant region(s) are preferably of human origin in case of therapeutic applications of the antibody of the present invention but could also be of for example rodent origin in case of animal studies; see also the Examples.

As used herein, the term "light chain portion" includes amino acid sequences derived from an immunoglobulin light chain. Preferably, the light chain portion comprises at least one of a $V_L$ or $C_L$ domain.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., *J. Immunol.* 161 (1998), 4083.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide. Accordingly, in one embodiment the polynucleotide is a cDNA encoding the variable region and at least part of the constant domain. In one embodiment, the polynucleotide is a cDNA encoding the variable region and the constant domain of an antibody of the present invention as defined herein.

Epitopes:

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, between about 15 to about 30 or between about 30 to about 50 contiguous or non-contiguous amino acids of a molecule of interest of the present invention, i.e. at least one IL-32 isotype, or the homologous sequences of the other IL-32 isotypes, in case the antibody recognizes more than one isotype.

Binding Characteristics:

By "binding" or "recognizing", used interchangeably herein, it is generally meant that a binding molecule, e.g., an antibody binds to a predetermined epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D". Unrelated epitopes are usually part of a nonspecific antigen (e.g., BSA, casein, or any other specified polypeptide), which may be used for the estimation of the binding specificity of a given binding molecule. In this respect, term "specific binding" refers to antibody binding to a predetermined antigen with a $K_D$ that is at least twofold less than its $K_D$ for binding to a nonspecific antigen. The term "highly specific" binding as used herein means that the relative $K_D$ of the antibody for the specific target epitope is at least 10-fold less than the $K_D$ for binding that antibody to other ligands.

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope. In respect of particular antigens, such as specific IL-32 isotypes the term "preferentially binding" means that the binding molecule, e.g., antibody specifically binds to an IL-32 isotype more readily than it would bind to a related, similar, homologous, or analogous IL-32 isotypes.

By way of non-limiting example, a binding molecule, e.g., an antibody may be considered to bind a first epitope preferentially if it binds said first epitope with dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind a molecule of interest of the present invention, a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, an antibody of the invention may be said to bind a molecule of interest of the present invention or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

A binding molecule, e.g., an antibody or antigen-binding fragment, variant, or derivative disclosed herein may be said to bind a molecule of interest of the present invention or a fragment or variant thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, an antibody of the invention may be said to bind a molecule of interest of the present invention or a fragment or variant thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., *Antibodies: A Laboratory Manual*, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In *Fundamental Immunology*, Paul, W. E., Ed., Raven Press New York, N Y (1984), Kuby, *Janis Immunology*, W. H. Freeman and Company New York, N Y (1992), and methods described therein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to a molecule of interest of the present invention. Preferred binding affinities include those with a dissociation constant or $K_D$ less than $5\times10^{-2}$M, $10^{-2}$M, $5\times10^{-3}$M, $10^{-3}$M, $5\times10^{-4}$M, $10^{-4}$ M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$M, $10^{-14}$ M, $5\times10^{-15}$ M, or $10^{-15}$ M. Typically, the antibody binds with a dissociation constant ($K_D$) of $10^{-7}$ M or less to its predetermined antigen. Preferably, the antibody binds its cognate antigen with a dissociation constant ($K_D$) of $10^{-9}$ M or less and still more preferably with a dissociation constant ($K_D$) of $10^{-11}$M or less.

Modifications of Antibodies:

The immunoglobulin or its encoding cDNAs may be further modified. Thus, in a further embodiment the method of the present invention comprises any one of the step(s) of producing a chimeric antibody, humanized antibody, single-chain antibody, Fab-fragment, bispecific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies provided by the present invention (Schier, *Human Antibodies Hybridomas* 7 (1996), 97-105; Malmborg, *J. Immunol. Methods* 183 (1995), 7-13). The production of chimeric antibodies is described, for example, in international application WO89/09622. Methods for the production of humanized antibodies are described in, e.g., European application EP-A1 0 239 400 and international application WO90/07861. Further sources of antibodies to be utilized in accordance with the present invention are so-called xenogeneic antibodies. The general principle for the production of xenogeneic antibodies such as human antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)$_2$, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as a label or a drug. Antigen binding molecules generated this way may be used for drug localization to cells expressing the appropriate surface structures of the diseased cell and tissue, respectively. This targeting and binding to cells could be useful for the delivery of therapeutically or diagnostically active agents and gene therapy/gene delivery. Molecules/particles with an antibody of the invention would bind specifically to cells/tissues expressing the particular antigen of interest, and therefore could have diagnostic and therapeutic use.

Samples:

As used herein, the term "sample" or "biological sample" refers to any biological material obtained from a subject or patient. In one aspect, a sample can comprise blood, cerebrospinal fluid ("CSF"), or urine. In other aspects, a sample can comprise whole blood, plasma, mononuclear cells enriched from peripheral blood (PBMC) such as lymphocytes (i.e. T-cells, NK-cell or B-cells), monocytes, macrophages, dendritic cells and basophils; and cultured cells (e.g., B-cells from a subject). A sample can also include a biopsy or tissue sample including tumor tissue. In still other aspects, a sample can comprise whole cells and/or a lysate of the cells. In one embodiment a sample comprises peripheral blood mononuclear cells (PBMC). Samples can be collected by methods known in the art.

Identification of Anti-IL-32 Antibodies, Isolation of Corresponding B Cells and Recombinant Expression of Anti-IL-32 Antibodies:

Identification of B-cells specific for the anti-IL-32 antibodies of the present invention, as enlisted in Table 1, and as exemplary shown in respect of the IL-32γ isotype and molecular cloning of antibodies displaying specificity of interest as well as their recombinant expression and functional characterization can be generally performed as described in the international applications WO 2013/098419 A1 and WO 2013/098420 A1; see Examples sections therein, in particular Examples 1 and 2 on pages 118 to 120 of WO 2013/098419 A1 and Examples 1 to 4 on pages 27 to 31 of WO 2013/098420 A1, the disclosure content of which is incorporated herein by reference.

Briefly, in one embodiment of the present invention cultures of single or oligoclonal B-cells were cultured and the supernatant of the culture, which contains antibodies produced by said B-cells was screened for presence and affinity of antibodies specific for one or more of the IL-32 isotypes, as described in the Examples. In another embodiment, patient sera were first screened for the presence of autoantibodies against IL-32 isotypes and then those with high titer were selected for peripheral blood mononuclear cells isolation; see Example 2 on pages 118-120 of WO 2013/098419 A1, the disclosure content of which is incorporated herein by reference. The screening process comprises screening for binding on fragments, peptides or derivatives of IL-32 isotypes. Subsequently, the antibody for which binding is detected or the cell producing said antibody were isolated; see Example 3 on page 120 of WO 2013/098419 A1, the disclosure content of which is incorporated herein by reference. Thus, a preliminary screen can be done on a panel of candidate donors, using samples containing antibody secreting cells (such as total peripheral blood or serum). In particular, mononuclear cells can be isolated from blood or lymphatic tissues using standard separation techniques for isolating peripheral blood mononuclear cells (PBMCs), such as gradient centrifugation. After and/or before this separation step, the samples of sera (or plasma), cell culture supernatants, or cells (obtained from different patients, from different tissues, and/or at different time points) can be prescreened using standard technologies for detecting the presence of antibodies and antibody-secreting cells (e.g. ELISA, BIACORE, Western blot, FACS, SERPA, antigen arrays, neutralization of viral infection in a cell culture system, or ELISPOT assays). The literature provides several examples of these technologies showing, for example, the use of ELISPOT for characterizing the immune response in vaccinated donors (Crotty et al., Immunol Meth. 286 (2004), 111-122), the use of antigen microarrays as diagnostic tools for newly infected patients (Mezzasoma et al., Clin Chem. 48 (2002), 121-130, and other technologies for measuring antigen-specific immune responses (Kern et al., Trends Immunol. 26 (2005), 477-484).

After identification of candidate anti-IL-32 antibodies and B cells secreting them, respectively, the nucleic acid sequence that encodes the antibody of interest is obtained, comprising the steps of preparing a B cell and obtaining/sequencing nucleic acid from the B cell that encodes the antibody of interest and further inserting the nucleic acid into or using the nucleic acid to prepare an expression host that can express the antibody of interest, culturing or sub-culturing the expression host under conditions where the antibody of interest is expressed and, optionally, purifying the antibody of interest. It goes without saying that the nucleic acid may be manipulated in between to introduce restriction sites, to change codon usage, and/or to add or optimize transcription and/or translation regulatory sequences. These techniques are state of the art and can be performed by the person skilled in the art without undue burden. For example, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, in Gilliland et al., *Tissue Antigens* 47 (1996), 1-20; Doenecke et al., *Leukemia* 11 (1997), 1787-1792. In a preferred embodiment of the present invention however, B cells are obtained and the corresponding antibody is expressed by the methods described in international application WO 2013/098420 A1, in particular in Example 3, on pages 28-30, the disclosure content of which is incorporated herein by reference.

Diseases and Disorders:

Unless stated otherwise, the terms "disorder" and "disease" are used interchangeably herein. The term "autoimmune disorder" as used herein is a disease or disorder arising from and directed against an individual's own tissues or organs or a co-segregate or manifestation thereof or resulting condition therefrom. Autoimmune diseases are primarily caused by dysregulation of adaptive immune responses and autoantibodies or autoreactive T cells against self-structures are formed. Nearly all autoimmune diseases have an inflammatory component, too. Autoinflammatory diseases are primarily inflammatory, and some classic autoinflammatory diseases are caused by genetic defects in innate inflammatory pathways. In autoinflammatory diseases, no autoreactive T cells or autoantibodies are found. In many of these autoimmune and autoinflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to a theory regarding B-cell mediated autoimmune disorder, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

As used herein, an "autoimmune disorder" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems including but not limited to systemic lupus erythematosus (SLE), rheumatoid arthritis, polymyositis, autoimmune polyendocrinopathy syndrome type 1 (APS1)/autoimmune polyendocrinopathy-candidiasis-ectodermal dystrophy (APECED) etc. Preferred such diseases include but are not limited to multiple sclerosis (MS), various forms of autoimmune rheumatologic disorders including but not limited to rheumatoid arthritis, spondyloarthritis, psoriatic arthritis, Sjogren's syndrome, scleroderma, lupus, including but not limited to SLE and lupus nephritis, polymyositis/dermatomyositis, and psoriatic arthritis), autoimmune dermatologic disorders (including but not limited to psoriasis, pemphigus group diseases, bullous pemphigoid diseases, and cutaneous lupus erythematosus), and autoimmune endocrine disorders (including but not limited to diabetic-related autoimmune diseases such as type 1 or insulin dependent diabetes mellitus (T1DM or IDDM), autoimmune thyroid disease (including but not limited to Graves' disease and thyroiditis)) and diseases affecting the generation of autoimmunity including but not limited to autoimmune polyendocrinopathy syndrome type 1 (APS1)/autoimmune polyendocrinopathy-candidiasis-ectodermal dystrophy (APECED) myasthenia gravis (MG/Thymoma).

Preferred diseases include, for example, SLE, RA, spondyloarthritis, psoriatic arthritis, T1DM, MS, psoriasis, Sjogren's syndrome, Graves' disease, thyroiditis, and glomerulonephritis, and APS1. Still more preferred are RA, SLE, and MS, and mostly preferred SLE.

Labels and Diagnostics:

Labeling agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., international application WO94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list. Traunecker, *Int. J. Cancer Surp. SuDP* 7 (1992), 51-52, describe the bispecific reagent janusin in which the Fv region directed to CD3 is coupled to soluble CD4 or to other ligands such as OVCA and IL-7. Similarly, the variable regions of the antibody of the invention can be constructed into Fv molecules and coupled to alternative ligands such as those illustrated in the cited article. Higgins, *J. Infect. Disease* 166 (1992), 198-202, described a hetero-conjugate antibody composed of OKT3 cross-linked to an antibody directed to a specific sequence in the V3 region of GP120. Such hetero-conjugate antibodies can also be constructed using at least the variable regions contained in the antibody of the invention methods. Additional examples of specific antibodies include those described by Fanger, *Cancer Treat. Res.* 68 (1993), 181-194 and by Fanger, *Crit. Rev. Immunol.* 12 (1992), 101-124. Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, *Seminars Cell. Biol.* 2 (1991), 59-70 and by Fanger, *Immunol. Today* 12 (1991), 51-54.

The above described fusion protein may further comprise a cleavable linker or cleavage site for proteinases. These spacer moieties, in turn, can be either insoluble or soluble (Diener et al., *Science* 231 (1986), 148) and can be selected to enable drug release from the antigen at the target site. Examples of therapeutic agents which can be coupled to the antibodies and antigens of the present invention for immunotherapy are chemokines, homing molecules, drugs, radioisotopes, lectins, and toxins. The drugs with which can be conjugated to the antibodies and antigens of the present invention depend on the disease context in which the conjugated molecules are intended to be used. For example, antibodies specific for targets useful in treatment of tumor diseases can be conjugated to compounds which are classically referred to as anti-neoplastic drugs such as mitomycin C, daunorubicin, and vinblastine. In using radioisotopically conjugated antibodies or antigens of the invention for, e.g., tumor immunotherapy, certain isotopes may be more preferable than others depending on such factors as leukocyte distribution as well as stability and emission. Depending on the autoimmune response, some emitters may be preferable to others. In general, α and ß particle emitting radioisotopes are preferred in immunotherapy. Preferred are short range, high energy α emitters such as $^{212}$Bi. Examples of radioisotopes which can be bound to the antibodies or antigens of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody or antigen of the invention, as well as ex vivo and in vivo therapeutic protocols, are known, or can be easily ascertained, by those of ordinary skill in the art. Non-limiting examples of suitable radionuclides for labeling are $^{198}$Au, $^{212}$Bi, $^{11}$C, $^{14}$C, $^{57}$Co, $^{67}$CH, $^{18}$F, $^{67}$Ga, $^{68}$Ga, $^{3}$H, $^{197}$Hg, $^{166}$Ho, $^{111}$In, $^{113m}$In, $^{123}$I, $^{125}$I, $^{127}$I, $^{131}$I, $^{111}$In, $^{177}$Lu, $^{15}$O, $^{13}$N, $^{32}$P, $^{33}$P, $^{203}$Pb, $^{186}$Re, $^{188}$Re, $^{105}$Rh, $^{97}$Ru, $^{35}$S, $^{153}$Sm and $^{99m}$Tc. Other molecules suitable for labeling are a fluorescent or luminescent dye, a magnetic particle, a metal, and a molecule which may be detected through a secondary enzymatic or binding step such as an enzyme or peptide tag. Commercial fluorescent probes suitable for use as labels in the present invention are listed in the Handbook of Fluorescent Probes and Research Products, 8th Edition, the disclosure contents of which are incorporated herein by reference. Magnetic particles suitable for use in magnetic particle-based assays (MPAs) may be selected from paramagnetic, diamagnetic, ferromagnetic, ferromagnetic and superpara-magnetic materials.

General methods in molecular and cellular biochemistry useful for diagnostic purposes can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996). Reagents, detection means and kits for diagnostic purposes are available from commercial vendors such as Pharmacia Diagnostics, Amersham, Bio-Rad, Stratagene, Invitrogen, and Sigma-Aldrich as well as from the sources given any one of the references cited herein, in particular patent literature.

Treatment and Drugs:

As used herein, the terms "treat" or "treatment" refer to both therapeutic treatment and prophylactic or preventative measures, wherein the object is to prevent or slow down (lessen) an undesired physiological change or disorder, such as the development of an autoimmune and/or autoinflammatory disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug," "medicine," or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents," "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug," "medicine," or "medicament" at an intended target location within the body of man or other animals, e.g., at the skin, in the stomach or the intestine. The terms "agent," "compound" or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

Examples of "anti-rheumatic drugs" and immunosuppressive drugs include chloroquine, hydroxycloroquine, myocrisin, auranofin, sulfasalazine, methotrexate, leflunomide, etanercept, infliximab (plus oral and subcutaneous methotrexate), adalimumab etc., azathioprine, D-penicilamine, gold salts (oral), gold salts (intramuscular), minocycline, cyclosporine including cyclosporine A and topical cyclosporine, tacrolimus, mycophenolate mofetil, cyclophosphamide, staphylococcal protein A (Goodyear and Silverman, J. Exp. Med., 197 (2003), 125-39), including salts and derivatives thereof, etc.

Examples of "non-steroidal anti-inflammatory drugs" or "NSAIDs" include aspirin, acetylsalicylic acid, ibuprofen and ibuprofen retard, fenoprofen, piroxicam, flurbiprofen, naproxen, ketoprofen, naproxen, tenoxicam, benorylate, diclofenac, naproxen, nabumetone, indomethacin, ketoprofen, mefenamic acid, diclofenac, fenbufen, azapropazone, acemetacin, tiaprofenic acid, indomethacin, sulindac, tolmetin, phenylbutazone, diclofenac and diclofenac retard, cyclooxygenase (COX)-2 inhibitors such as GR 253035, MK966, celecoxib (CELEBREX®; 445-(4-methylphenyl)-3-(trifluoromethyl)-1H-pyrazol-1-yl), benzenesulfonamide and valdecoxib (BEXTRA®), and meloxicam (MOBIC®), including salts and derivatives thereof, etc. Preferably, they are aspirin, naproxen, ibuprofen, indomethacin, or tolmetin. Such NSAIDs are optionally used with an analgesic such as codenine, tramadol, and/or dihydrocodinine or narcotic such as morphine.

By "subject" or "individual" or "animal" or "patient" or "mammal," is meant any subject, particularly a mammalian subject, e.g., a human patient, for whom diagnosis, prognosis, prevention, or therapy is desired.

Pharmaceutical Carriers:

Pharmaceutically acceptable carriers and administration routes can be taken from corresponding literature known to the person skilled in the art. The pharmaceutical compositions of the present invention can be formulated according to methods well known in the art; see for example Remington: *The Science and Practice of Pharmacy* (2000) by the University of Sciences in Philadelphia, ISBN 0-683-306472, *Vaccine Protocols*. 2nd Edition by Robinson et al., Humana Press, Totowa, N.J., USA, 2003; Banga, *Therapeutic Peptides and Proteins: Formulation, Processing, and Delivery Systems*. 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are preferably adjusted to a pH and isotonic state compatible with the nasal mucous membranes. Pharmaceutical compositions for oral administration, such as single domain antibody molecules (e.g., "Nanobodies™") etc are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., *Nature Reviews, Drug Discovery* 2(9) (2003), 727-735. Further guidance regarding formulations that are suitable for various types of administration can be found in *Remington's Pharmaceutical Sciences*, Mace Publishing Company, Philadelphia, Pa., 17th ed. (1985) and corresponding updates. For a brief review of methods for drug delivery see Langer, *Science* 249 (1990), 1527-1533.

Dosage Regimen:

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as anti-tumor agents and cytotoxic drugs, depending on the intended use of the pharmaceutical composition.

In addition, co-administration or sequential administration of other agents may be desirable. A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Preferably, the therapeutic agent in the composition is present in an amount sufficient for preventing inflammation or suppression of the immune response.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, *TIBTECH* 12 (1994), 352-364.

The above disclosure generally describes the present invention. Several documents are cited throughout the text of this specification. Full bibliographic citations may be found at the end of the specification immediately preceding the claims. The contents of all cited references (including literature references, issued patents, published patent applications as cited throughout this application, including the disclosure in the background section and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The Examples 1 to 6 which follow and corresponding FIGS. 1 to 12 further illustrate the invention, but should not be construed to limit the scope of the invention in any way. Detailed descriptions of conventional methods, such as those employed herein can be found in the cited literature; see also "*The Merck Manual of Diagnosis and Therapy*" Seventeenth Ed. ed. by Beers and Berkow (Merck & Co., Inc., 2003).

The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) *Molecular Cloning: A Laboratory Manual*, 2nd ed., Cold Spring Harbor Laboratory Press); *DNA Cloning*, Volumes I and II (Glover ed., 1985); *Oligonucleotide Synthesis* (Gait ed., 1984); *Nucleic Acid Hybridization* (Hames and Higgins eds. 1984); *Transcription And Translation* (Hames and Higgins eds. 1984); *Culture Of Animal Cells* (Freshney and Alan, Liss, Inc., 1987); *Gene Transfer Vectors for Mammalian Cells* (Miller and Calos, eds.); *Current Protocols in Molecular Biology and Short Protocols in Molecular Biology*, 3rd Edition (Ausubel et al., eds.); and *Recombinant DNA Methodology* (Wu, ed., Academic Press). *Gene Transfer Vectors For Mammalian Cells* (Miller and Calos, eds., 1987, Cold Spring Harbor Laboratory); *Methods In Enzymology*, Vols. 154 and 155 (Wu et al., eds.); *Immobilized Cells And Enzymes* (IRL Press, 1986); *Perbal, A Practical Guide To Molecular Cloning* (1984); the treatise, *Methods In Enzymology* (Academic Press, Inc., N.Y.); *Immunochemical Methods In Cell And Molecular Biology* (Mayer and Walker, eds., Academic Press, London, 1987); *Handbook Of Experimental Immunology*, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., *Curr. Opin. Biotechnol.* 8 (1997), 148); Serum-free Media (Kitano, Biotechnology 17 (1991), 73); Large Scale Mammalian Cell Culture (*Curr. Opin. Biotechnol.* 2 (1991), 375); and Suspension Culture of Mammalian Cells (Birch et al., *Bioprocess Technol.* 19 (1990), 251.

Material and Methods

Patients selection, peripheral blood mononuclear cells (PBMC) isolation from APECED/APS1 Patients memory, B cell culture and antibody isolation were carried out as described in the international applications WO 2013/098419 A1 and WO 2013/098420 A1 with the difference that specificity of the antibodies isolated and analyzed was directed towards IL-32 isotypes as defined hereinabove and below instead of IL-17 and IL-22, which were specifically used in the mentioned PCT applications; see Examples sections therein, in particular Examples 1 and 2 on pages 117 to 120 and Example 17 on pages 168-171 of WO 2013/098419 A1 and Examples 1 to 4 on pages 27 to 31 of WO 2013/098420 A1, the disclosure content of which is incorporated herein by reference.

The molecular cloning of human antibodies of the present invention and subsequent antibody production and purification were performed as described in the international application WO 2013/098419 A1, see the Examples section of the application and in particular Examples 1 to 3 on pages 117-120 therein, the disclosure content of which is incorporated herein by reference.

Mutation analysis of the AIRE gene was performed as described in the international application WO 2013/098419 A1; see the Examples therein, in particular the "Mutation analysis of the AIRE gene" section in Materials and Methods of the Examples, on pages 115-116, the disclosure content of which is incorporated herein by reference, with particular steps performed as described in WO99/15559. In this concern, genotyping of the respective mutations in the AIRE (APECED) gene is performed as described in international application WO99/15559 in Example 2 at pages 12 to 13; a confirmation of the mutations in exons 2 and 6 of the AIRE gene as described in Example 3 of international application WO99/15559 at page 13, line 5 bridging to page 14, line 13, the disclosure content of which is incorporated herein by reference in its entirety. In particular, for the mutation analysis the DNA samples are purified from peripheral blood mononuclear cells from patients with APECED and from suspected carriers of APECED and from normal healthy controls (according to Sambrook et al. 1989, *Molecular Cloning. A Laboratory Manual*. CSH Press) and subjected to PCR using primers specific for all identified exons.

Example 1: Detection of Human Cytokine Specific Antibodies in the Serum of Patients by ELISA The general presence of various cytokine and disease specific antibodies in the sera of the patients suffering from the genetic condition APECED (Autoimmune polyendocrinopathy candidiasis epidermal dysplasia, also called Autoimmune polyendocrinopathy type 1 (APS1)) has been obtained by Protoarray analysis as described in Example 7 on page 128 and indicated Tables 1 and 2 on pages 128-130 of applicant's international application WO 2013/098419 A1, the disclosure content of which is incorporated herein by reference. Furthermore, ELISA (Enzyme linked immunosorbent assay) was used for differential analysis of IL-32gamma vs. alpha analysis in the sera of the patients suffering from the genetic condition APECED (Autoimmune polyendocrinopathy candidiasis epidermal dysplasia, also called Autoimmune polyendocrinopathy type 1 (APS1). Altogether sera from 30 patients, presented by codes from APS1-1 to APS1-30 were used in the assays (see FIG. 2). ELISA—IL-32γ and IL-32α

96 well microplates (Costar, USA) were coated with human IL-32γ (R&D) or IL-32α (ImmunoTools). Plates were washed with PBS-T and blocked 1 h at room temperature with PBS containing 2% BSA (Sigma, Buchs, Switzerland). Patient sera, B cell conditioned medium, or recombinant antibody preparations were incubated for 2 h at room temperature. Binding of human IgG to the antigen of interest was determined using a horseradish peroxidase conjugated goat anti human Fc-gamma-specific antibody (Jackson ImmunoResearch, Europe Ltd., Cambridgeshire, UK) followed by measurement of the HRP activity using a TMB substrate solution (TMB, Sigma, Buchs, Switzerland).

Example 2: EC50 ELISA Determination of the Antibodies of the Present Invention EC50 binding of exemplary anti-IL-32 antibodies of the present invention to IL-32γ (R&D) or IL-32α (ImmunoTools), was determined by ELISA. Serial dilutions of MABs (from 100,000 ng/ml down to 1.69 ng/ml) were incubated for 2 hours with antigen-coated plates (coating overnight at 1 μg/ml in PBS, followed by wash out and blocking with 2% BSA in PBS). The plates were subsequently washed and binding of MABs was detected with anti-human HRP-conjugated Fc-gamma-specific secondary antibody (Jackson ImmunoResearch, Europe Ltd., Cambridgeshire, UK). Concentrations of MAB resulting in half of maximal binding to respective antigens (EC50, ng/ml) were calculated using Prism 4 GraphPad software on sigmoidal dose-response curves (variable slope, 4 parameters) obtained by plotting the log of the concentration versus OD 450 nm measurements; for the results see FIG. 3 and Table 4 below.

TABLE 3

Summary of EC50 values of binding of MABs to IL-32gamma and IL-32alpha MABs 14B3, 19A1, 26A6 did not bind to IL-32alpha at the highest concentration tested (100 ug/ml). MAB 2C2 bound to IL-32alpha only at very high concentrations indicating that EC50 binding is higher than 30 μg/ml.

| | EC50 (ng/ml) | | | |
|---|---|---|---|---|
| | 14B3 | 19A1 | 26A6 | 2C2 |
| IL-32gamma | 604 | 460 | 1332 | 526 |
| IL-32alpha | n.b. | n.b. | n.b. | >30.000 |

Example 3: IL-6 Neutralization Assay

The neutralizing assays are carried out on cell lines that respond to the studied cytokine. The ligand binding to receptor in general activates a corresponding signaling pathway, translocation of transcription factors to the nucleus and upregulate responder gene transcription, translation and if applicable product secretion. The cytokine concentration used is selected from the beginning of the linear part of the dose-response curve to maximize the sensitivity of the assay. To test the neutralizing capacity of antibodies the optimal concentration of the target cytokine is preincubated with serial dilutions of serum, supernatant or purified antibody samples. The results are expressed as titer or concentration of antibody that show the value half-way between the positive and negative controls. Although the interleukin-32 receptor has not yet been reported, it is known that interleukin-32 can induce other inflammatory cytokines such as IL-6 from monocytes/macrophages in vitro and in vivo (Shoda et al., Arthritis Res Ther. 8 (2006); R166). Accordingly, secreted IL-6 may be and was used as readout of IL-32 activity and was quantitated with a commercial ELISA kit (Biolegend) in the neutralization assay of the present invention.

RAW 264.7 macrophages were conditioned in serum-free DMEM overnight. IL-32gamma (R&D, final concentration 50 ng/ml) was preincubated with serial dilutions of serum-free supernatant of HEK293T cells expressing the indicated monoclonal antibodies in serum-free DMEM for 2 hours at 37° C. in the wells of 96-well culture plate. Cells were added at 10,000 cells per well and incubated 18 hours at 37° C. in CO2 incubator. Subsequently, secretion of IL-6 was used to monitor the neutralizing activity of the anti-IL-32 antibodies of the present invention; see FIG. 4B

Example 4: Validation of Subject Antibodies

Ear Inflammation Assay

Ear inflammation phenotype was induced in 8 weeks old C57BL/6J (WT; from Charles River) mice by intradermal injection of human cytokine IL-32γ, or IgG control in 20 μl of PBS (or PBS control) into each ear given on alternate days at Day 1, Day 4, Day 6 and Day 8 (20 μl/ear, 125 ng/ear, 250 ng/mouse/day) using a 30-gauge needle. Treatment with the exemplary anti-IL-32 2C2 antibody of the present invention was tested on these animals in respect of its neutralizing potential to reduce the induced ear inflammation phenotype. Only one IP injection of 2C2 or control human IgG [200 μg, 100 μg or 50 μg/IP] was administered to the animals at Day 0, prior to induction of ear inflammation. The mice were sacrificed at day 11.

To test a potential therapeutic effect of the antibodies of the present invention ear thickness measurements of the animals were taken with a Mitutoyo digital micrometer during the IL-32 administration by daily measurements prior to IL-32 injection.

Figure 7:
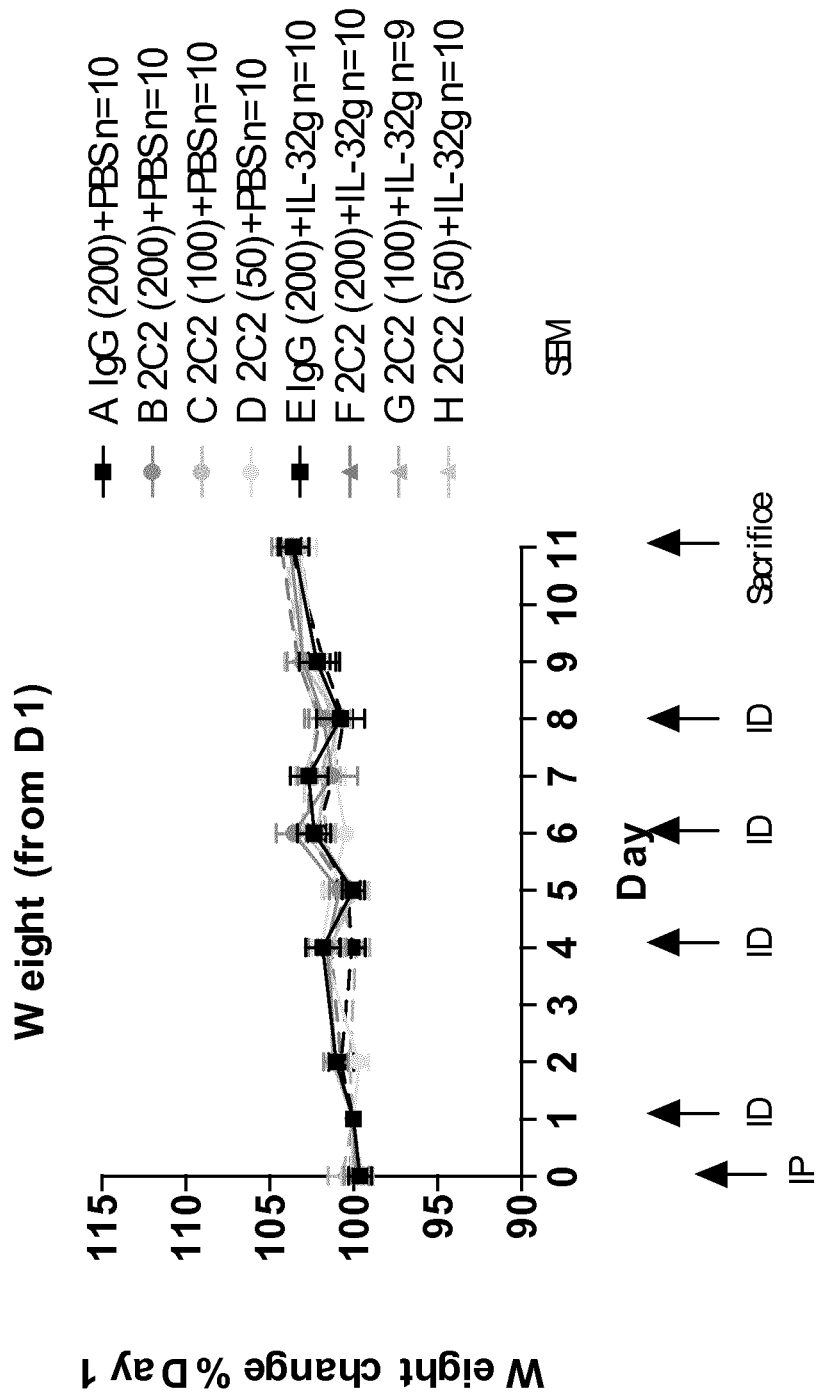
FIG. 7: CytoEar assay—weight monitoring. No significant weight changes were observed in either of the animals tested in the experiment.
Figure 8:
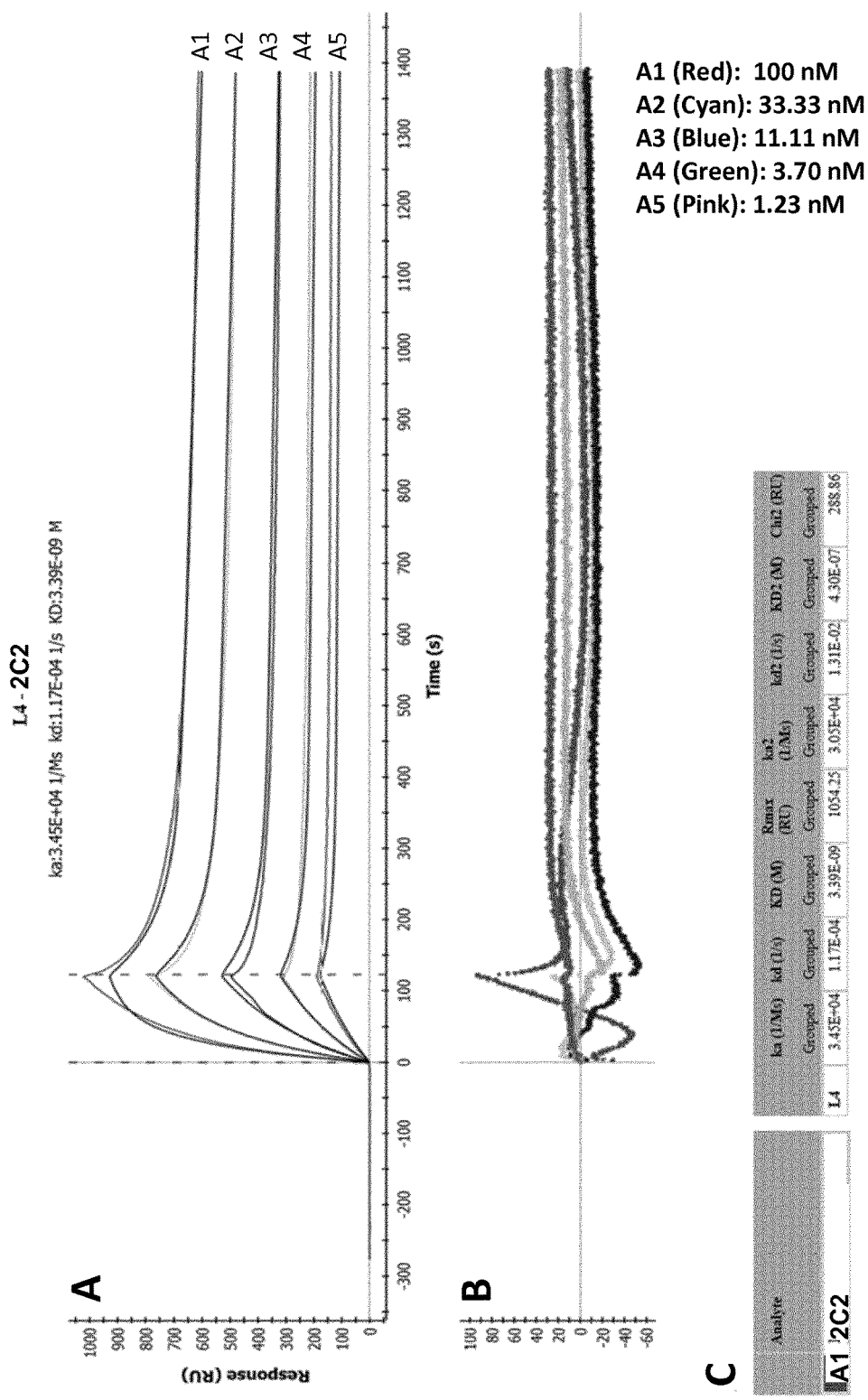
FIG. 8: Detailed analysis of the sensograms concerning the binding of IL-32 to the anti-IL-32 2C2 antibody of the present invention. Non 1:1 behavior was observed, which allows best fit to a heterogeneous ligand. (A) Overlayed graphs for the Langmuir fit and experimental data of the binding reaction indicate a good fit to 1.1 Langmuir model. IL-32 was injected in concentrations of A1: 100 nM, A2: 33.33 nM, A3: 11.11 nM A4: 3.70 nM A5: 1.23 nM. Residuals plot (B) shows a random scatter with the magnitude of the noise level indicating a good residual fit. (C) Table below the figures shows the kinetic parameters derived from the fitted curves for the association (ka), dissociation (kd), Rmax and the calculated dissociations constant KD. KD of the exemplary anti-IL-32 2C2 antibody of the present invention appears to be in nM range.

Furthermore, body weight has been monitored during the treatment, however, no significant weight changes have been observed in any of the animal groups due to the treatment applied; see FIG. 7. In addition, after sacrifice of the animals H&E (hematoxylin and eosin; see Harris, H. F., J. Appl. Microscopy III (1900), 777-781 and Mallory, F. B.: Pathological technique. Philadelphia, Saunders, (1938)) histology stainings of the ears are performed.

Combination of two independent experiments shows that the induction of ear swelling with intradermal injection of human IL-32γ is reduced in the presence of 2C2 neutralizing antibody; see FIGS. 5 and 6. This is significant at Day 9 for the lower antibody doses of 100 μg, respective 50 μg/IP; see FIG. 5C, D and FIG. 6 C, D. For the highest dosage of 200 μg/IP, significant reduction of the ear swelling can be even observed starting with day 5; see FIG. 5B and FIG. 6B. The level of ear swelling following the continuous intradermal injection of PBS control is not affected by the presence of IgG or 2C2; see FIG. 6A-D.

Figure 9:
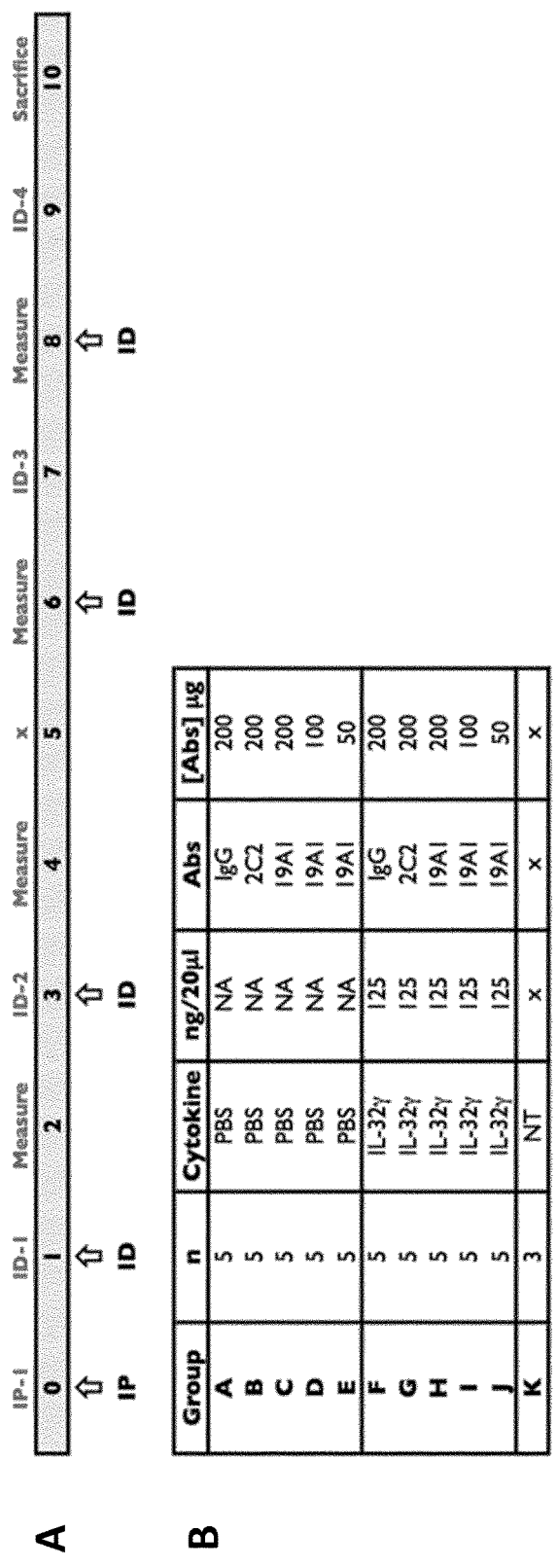
FIG. 9: Effect of 19A1 blocking antibody following hIL-32γ induced inflammation in comparison to 2C2 in CytoEar assay. To induce inflammation hIL-32γ was injected at a concentration of 6.25 µg/ml, 125 ng/ear. A: Exemplary 10-day experimental timeline. B: Overview of the experimental treatment of the experimental animal groups A to F. C-F: Mice cohorts (C57/BL6, 8 weeks) were IP injected with stated amounts of 2C2 or 19A1 antibodies (or IgG control) at experiment initial day, while 125 ng hrIL-32γ cytokine in 20 ul of PBS (or PBS control) was intradermally injected into mice ears every 48-72 hours. Ear thickness measurements were taken with a Mitutoyo digital micrometer. CytoEar ear thickness measurements calculated as fold change relative to initial day measurements, then normalised to relevant PBS controls, for each cohort. Mean+/−SEM, N stated on figure. P values obtained by ANOVA testing. IP=intraperitoneal antibody injection, ID=intradermal ear injection, NT=non-treated control.
Figure 9:
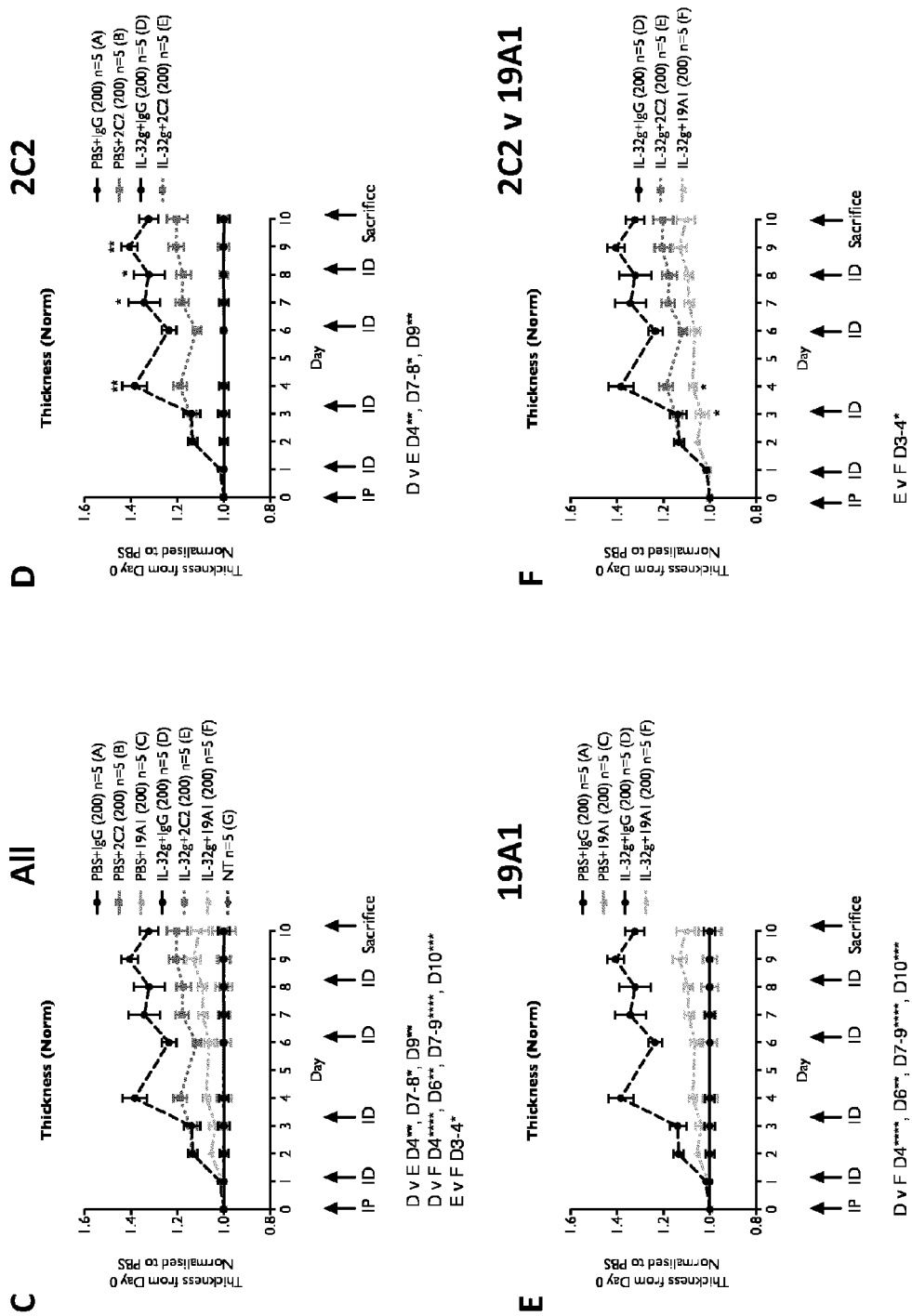
Figure 10:
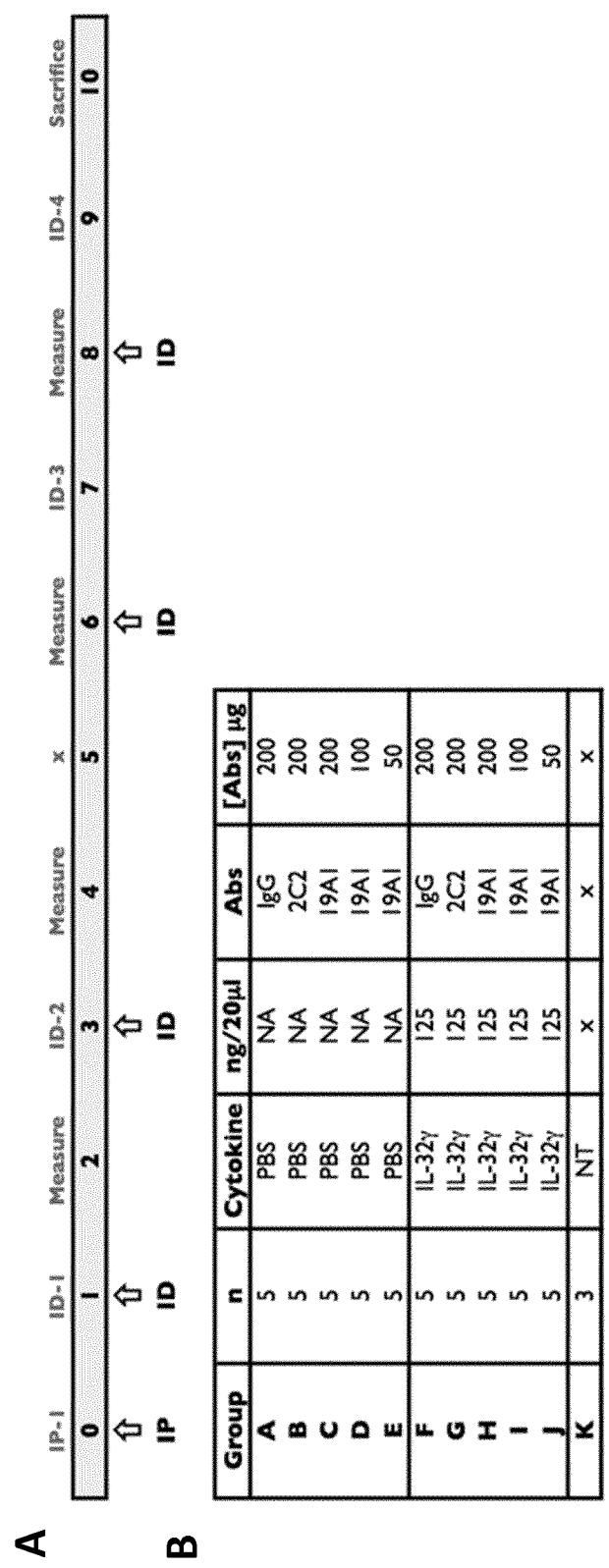
FIG. 10: Effect of different doses of 19A1 antibody following hIL-32γ induced inflammation in CytoEar assay. To induce inflammation hIL-32γ was injected at a concentration of 6.25 µg/ml, 125 ng/ear. A: Exemplary 10-day experimental timeline. B: Overview of the experimental treatment of the experimental animal groups A to K. C-F: Mice cohorts (C57/BL6, 8 weeks) were IP injected with stated amounts of 2C2 or 19A1 antibodies (or IgG control) at experiment initial day, while 125 ng hrIL-32γ cytokine in 20 ul of PBS (or PBS control) was intradermally injected into mice ears every 48-72 hours. Ear thickness measurements were taken with a Mitutoyo digital micrometer. CytoEar ear thickness measurements calculated as fold change relative to initial day measurements, then normalised to relevant PBS controls, for each cohort. Mean+/−SEM, N stated on figure. P values obtained by ANOVA testing. IP=intraperitoneal antibody injection, ID=intradermal ear injection, NT=non-treated control.
Figure 10:
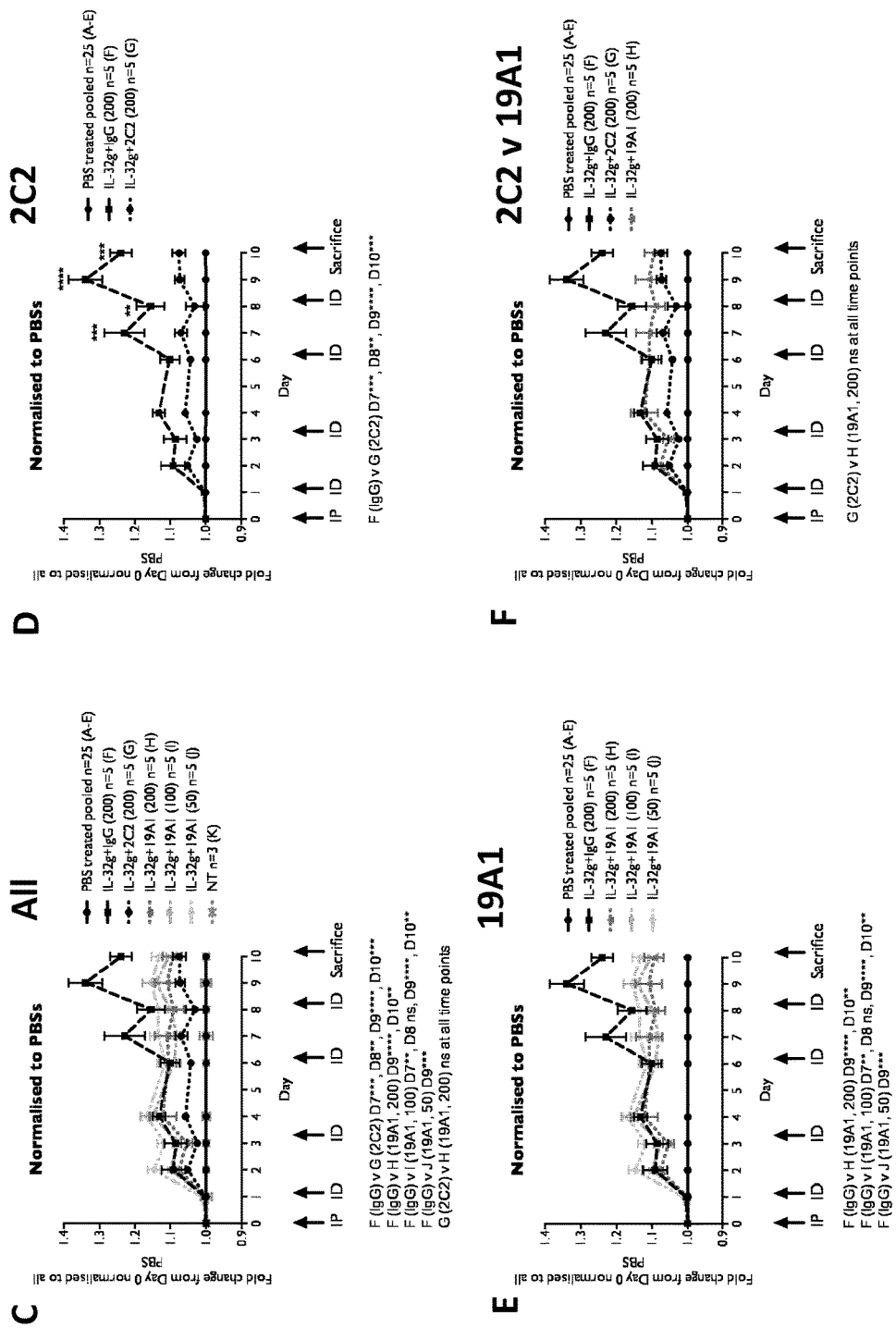

Exemplary anti-IL-32 antibody 2C2 demonstrates dose dependent effects and is able to neutralize the injected IL-32γ in a mouse model. Furthermore, as shown in FIGS. 9 and 10 antibody 19A1 effectively neutralizes hIL-32γ induced inflammation in comparison to antibody 2C2 in the CytoEar assay. Accordingly, the data presented herein indicate that the anti-IL-32 antibody of the present invention is effective against IL-32γ in cytokine induced ear inflammation experiments, demonstrating the therapeutic value of the IL-32 specific binding molecules of the present invention.

CytoAnkle Assay:

Despite the fact that no mouse homologue of IL-32 has been identified yet, there are hints, as for example the induced ear swelling phenotype as described supra, that at least some members of the IL-32 pathway are present in the mice as well. Furthermore, Joosten et al. (2006) have injected human IL-32 into the knee joints of mice, which led to the induction of joint swelling, and used such experiments as a model for RA. Such experiments have been also performed in connection with the present invention, however, the animals have demonstrated no measurable swelling after IL-32 injections, which might be due to the difficulty of measuring knee thickness through intervening muscle tissue. Due to this fact the present invention established a novel assay to test the effects of IL-32 in mice and in particular of the exemplary anti-IL-32 antibodies of the present invention, as described below.

In this assay mice cohorts (C57/BL6, 7-8 weeks) are intraarticular (IA) injected with 62.5-250 ng cytokine, e.g., an IL-32 isotype such as IL32γ or IL-32α or mixtures of several IL-32 isotypes in 10 ul of PBS (or PBS control) into ankles every 48-72 hours. Axial ankle thickness measurements are than taken with a Mitutoyo digital micrometer. Animals are weighed each day and respective IL-32 isotype or isotypes are administered while the mice are anaesthetized with isofluorane. The experimental time frame is designed as indicated above for the ear inflammation assay, with injections of the anti-IL-32 antibody or antibodies of the present invention, respective the control groups obtaining either PBS or human IgGs of IL-32 non-related binding specificity as indicated above. Reduction of the ankle swelling is used as a readout of the therapeutic effect of the antibodies.

In addition the weight of the anti-IL32 antibody treated and of the control animals is monitored during the treatment, and after sacrifice of the animals H&E (hematoxylin and eosin) histology stainings of the ears are performed.

Figure 11:
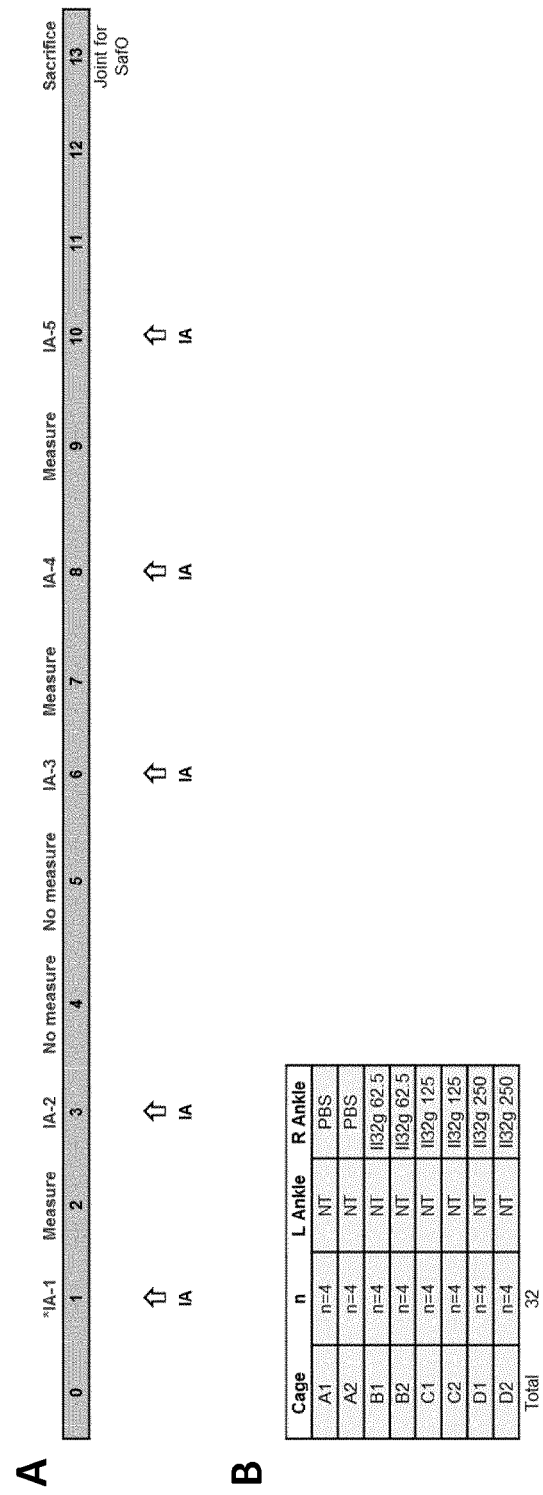
FIG. 11: Dose dependency of IL-32 in inducing inflammation in CytoAnkle assay. To induce inflammation mice obtained intraarticular ankle injections of 10 µl hIL-32γ in the right ankle, whereas the left ankle was injected with PBS. A: Exemplary 13-day experimental timeline. B: Overview of the experimental treatment of the experimental animal cages A1 to D2. C-D: Mice cohort (C57/BL6, 8 weeks) were IA injected with stated amounts of hrIL-32γ cytokine in 10 ul of PBS (or PBS control) into mice ankles every 48-72 hours. Axial ankle thickness measurements were taken with a Mitutoyo digital micrometer. CytoAnkle thickness measurements calculated as fold change relative to initial day measurements, then normalised to relevant PBS controls, for each cohort. Mean+/−SEM, N stated on figure. P values obtained by ANOVA testing. IA=intraarticular ankle injection.
Figure 12:
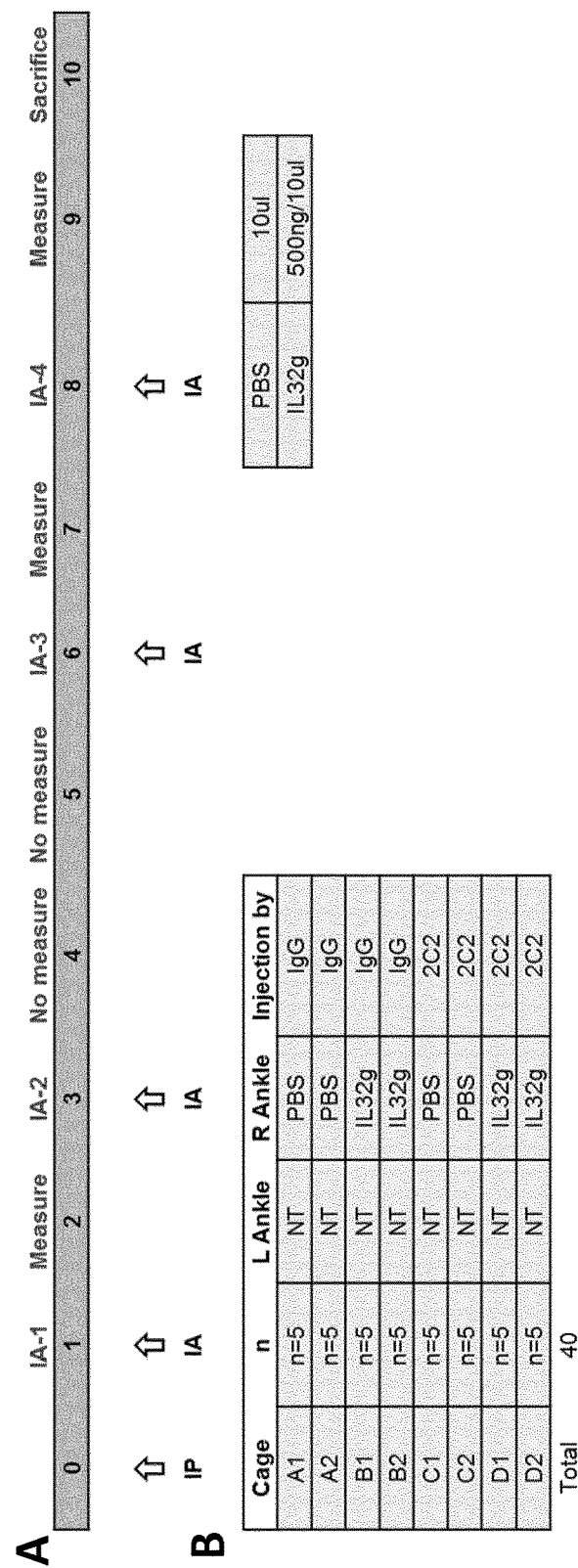
FIG. 12: Effect of 2C2 antibody following hIL-32γ induced inflammation in CytoAnkle assay. CytoAnkle test: +/−IL-32γ+/−2C2. A: Exemplary 10-day experimental timeline. B: Overview of the experimental treatment of the experimental animal cages A1 to D2. C-D: Mice cohort (C57/BL6, 8 weeks) were IP injected with 200 µg of 2C2 antibodies (or IgG control) at experiment initial day, while 500 ng of hrIL-32γ cytokine in 10 µl of PBS (or PBS control) was IA injected into mice ankles every 48-72 hours. Axial ankle thickness measurements were taken with a Mitutoyo digital micrometer. CytoAnkle thickness measurements calculated as fold change relative to initial day measurements, then normalised to relevant PBS controls, for each cohort. Mean+/−SEM, N stated on figure. P values obtained by ANOVA testing. IP=intraperitoneal antibody injection, IA=intraarticular ankle injection.
Figure 12:
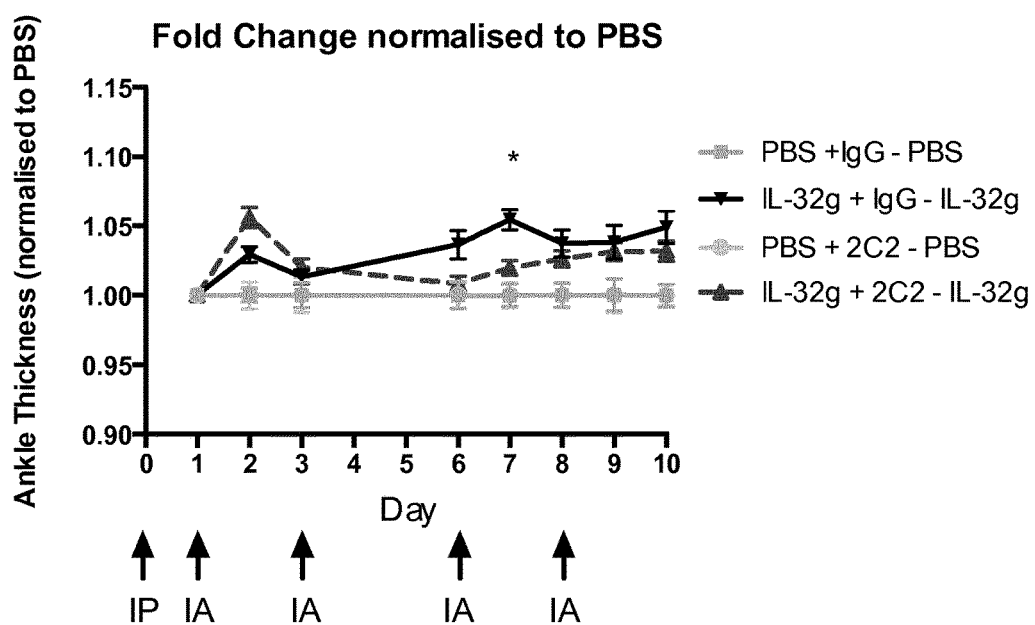

FIG. 11 shows an exemplary experimental set up of the CytoAnkle assay (FIG. 11 A, B) and the dose dependency of IL-32 in inducing inflammation in the CytoAnkle assay (FIG. 11 C, D). As further shown in FIG. 12, the anti-IL-32 inflammatory effect of the 2C2 antibody could be confirmed in the CytoAnkle assay (FIG. 12 C-E).

Example 5: Epitope Mapping of Exemplary IL-32 Antibodies

As a first step of mapping, differential binding of a-IL-32 MABs to distinct antigen binding sites is examined to determine the number of different binding sites.

For this purpose, two approaches are used. In the first approach MABs are expressed either with human (hMAB) or mouse (hmMAB) Fc and cross-competition experiments are carried out by coating antigen on plates and by detecting binding of hmMABs in the presence of large excess of human MABs. Detection of hmMABs bound to the ligand is performed by a HRP-conjugated secondary antibody directed against the Fc portion of the primary antibody.

Subsequent the binding regions of MABs to their respective antigens are attempted to map using PepStar™ analysis. Herein, overlapping 20mer peptides (15 amino acid overlap) are designed to cover the IL-32 isotypes of interest, e.g., IL-32γ, IL-32α, IL-32δ. IL32β and the remaining isotypes 5 and 6, including all known variants. The peptides and full length antigen (as positive control) are spotted on microarray and the peptide microarray is incubated with the primary antibody followed by a fluorescently labelled secondary antibody directed against the Fc portion of the primary antibody. To avoid false negatives caused by steric hindrance, an optimized hydrophilic linker moiety is inserted between the glass surface and the antigen derived peptide sequence.

Example 6: Antibody Affinity Measurements Using SPR Technology

For affinity determination of the antibodies of the present invention surface plasmon resonance SPR measurements were performed using a ProteOn™ XPR36 instrument, according to the instructions of the manufacturer (BIO-RAD; Hercules Calif., USA) using the molecules of interest of the present invention in an analogous experimental setup as described in Example 14 of international application WO 2013/098419 A1 on pages 163-165, the disclosure content of which is incorporated herein by reference. By this method, affinity of the exemplary IL-32 antibody of the present invention, 2C2 has been determined by SPR to be in the nanomolar range at about 4 nM; see FIG. 8 and the table in FIG. 8C.

The invention claimed is:

1. A chimeric monoclonal anti-interleukin-32 (IL-32) antibody or IL-32 binding fragment thereof wherein the antibody or antigen-binding fragment thereof comprises in its variable regions the complementarity determining regions (CDRs)
V$_H$ CDRs: (a) the amino acid sequence of amino acids 31-37 of SEQ ID NO:2 and
(b) the amino acid sequence of amino acids 52-67 of SEQ ID NO:2 and
(c) the amino acid sequence of amino acids 100-107 of SEQ ID NO:2; and
V$_L$ CDRs: (d) the amino acid sequence of amino acids 23-35 of SEQ ID NO:4 and
(e) the amino acid sequence of amino acids 51-57 of SEQ ID NO:4 and
(f) the amino acid sequence of amino acids 90-101 of SEQ ID NO:4;
wherein the antibody:
binds to human IL-32gamma (IL-32γ); and
(ii) neutralizes the biological activity of IL-32γ,
wherein the antibody or fragment thereof comprises a human IgG1 constant region.

2. The monoclonal anti-IL-32 antibody or IL-32 binding fragment thereof of claim 1 comprising in its variable regions:
(a) the amino acid sequence of the V$_H$ and/or V$_L$ region as depicted in SEQ ID NOs: 2 and 4, respectively; or
(b) a heavy chain and/or light chain variable region comprising an amino acid sequence at least 95% identical to the amino acid sequence of (a).

3. The monoclonal anti-IL-32 antibody or IL-32 binding fragment thereof of claim 1 comprising a C$_H$ and/or C$_L$ constant region comprising an amino acid sequence selected from SEQ ID NOs:14 and 16.

4. The monoclonal anti-IL-32 antibody or IL-32 binding fragment thereof of claim 1, wherein the variable region comprises an amino acid sequence selected from the group consisting of SEQ ID NOs:2 and 4.

5. The monoclonal anti-IL-32 antibody or IL-32 binding fragment thereof of claim 1, wherein the constant region comprises an amino acid sequence selected from the group consisting of SEQ ID NOs: 14 and 16.

6. The monoclonal anti-IL-32 antibody or IL-32 binding fragment thereof of claim 1, which is a human monoclonal antibody or IL-32 binding fragment thereof.

7. The monoclonal anti-IL-32 antibody or IL-32 binding fragment thereof of claim 1, which is
(i) detectably labeled with a label selected from the group consisting of an enzyme, a radioisotope, a fluorophore, a peptide and a heavy metal; or
(ii) attached to a drug.

8. The monoclonal anti-IL-32 antibody or IL-32 binding fragment thereof of claim 1, wherein the variable region is encoded by a polynucleotide selected from the group consisting of SEQ ID NOs:1 and 3.

9. The monoclonal anti-IL-32 antibody or IL-32 binding fragment thereof of claim 1, wherein the constant region is encoded by a polynucleotide selected from the group consisting of SEQ ID NOs: 13 and 15.

10. A method of treating an inflammatory or autoimmune disease or condition comprising administering to a subject in need of such treatment the monoclonal anti-IL-32 antibody or IL-32 binding fragment thereof of claim 1, wherein the inflammatory or autoimmune disease or condition is associated with the expression of IL-32, and is selected from the group consisting of inflammatory bowel disease (IBD; including Crohn's Disease, ulcerative colitis and Celiac's Disease), psoriasis, rheumatoid arthritis (RA), ankylosing spondylitis and other forms of spondyloarthritis, psoriatic arthritis, myasthenia gravis, chronic obstructive pulmonary disease (COPD), asthma, tuberculosis, cancer including leukemia, vascular inflammation and atherosclerosis.

11. A method for diagnosing an inflammatory or autoimmune disease or condition in a subject associated with the expression of IL-32 comprising contacting a biological sample of the subject with an anti-IL-32 antibody or IL-32 binding fragment thereof of claim 1, and detecting the presence of IL-32γ in the biological sample.

12. A polynucleotide encoding the monoclonal anti-IL-32 antibody or IL-32 binding fragment thereof of claim 1.

13. A monoclonal anti-IL-32 antibody or IL-32 binding fragment thereof, which is selected from the group consisting of a single chain Fv fragment (scFv), an F(ab') fragment, an F(ab) fragment, and an F(ab')$_2$ fragment and comprises in its variable regions the complementarity determining regions (CDRs)
$V_H$ CDRs:
(a) the amino acid sequence of amino acids 31-37 of SEQ ID NO:2 and
(b) the amino acid sequence of amino acids 52-67 of SEQ ID NO:2 and
(c) the amino acid sequence of amino acids 100-107 of SEQ ID NO:2; and
$V_L$ CDRs:
(d) the amino acid sequence of amino acids 23-35 of SEQ ID NO:4 and
(e) the amino acid sequence of amino acids 51-57 of SEQ ID NO:4 and
(f) the amino acid sequence of amino acids 90-101 of SEQ ID NO:4;
wherein the antibody
(i) binds to human IL-32gamma (IL-32γ); and
(ii) neutralizes the biological activity of IL-32γ, and
wherein the antibody, F(ab') fragment, F(ab) fragment, or F(ab')$_2$ fragment comprises a human IgG1 constant region.

14. A cDNA molecule encoding a monoclonal anti-interleukin-32 (IL-32) antibody or IL-32 binding fragment thereof wherein the antibody or antigen-binding fragment thereof comprises in its variable region the complementarity determining regions (CDRs):
$V_H$ CDRs: (a) the amino acid sequence of amino acids 31-37 of SEQ ID NO:2 and
(b) the amino acid sequence of amino acids 52-67 of SEQ ID NO:2 and
(c) the amino acid sequence of amino acids 100-107 of SEQ ID NO:2; and
$V_L$ CDRs: (d) the amino acid sequence of amino acids 23-35 of SEQ ID NO:4 and
(e) the amino acid sequence of amino acids 51-57 of SEQ ID NO:4 and
(f) the amino acid sequence of amino acids 90-101 of SEQ ID NO:4; and wherein the antibody:
binds to human IL-32gamma (IL-32γ); and
(ii) neutralizes the biological activity of IL-32γ.

15. The cDNA molecule of claim 14, wherein the anti-IL-32 antibody or IL-32 binding fragment thereof comprises in its variable regions:

(a) the amino acid sequence of the $V_H$ and/or $V_L$ region as depicted in SEQ ID NO: 2 and 4, respectively; or
(b) a heavy chain and/or light chain variable region comprising an amino acid sequence at least 95% identical to the amino acid sequence of (a).

16. The cDNA molecule of claim 14, wherein the anti-IL-32 antibody or IL-32 binding fragment thereof comprises a $C_H$ and/or $C_L$ constant region at least 95% identical to an amino acid sequence selected from SEQ ID NOs: 6, 14 and 16.

17. The cDNA molecule of claim 14, wherein the anti-IL-32 antibody or IL-32 binding fragment thereof is selected from the group consisting of a single chain Fv fragment (scFv), an F(ab') fragment, an F(ab) fragment, an F(ab')$_2$ fragment and a single domain antibody fragment (sdAB).

18. The cDNA molecule of claim 14, wherein the anti-IL-32 antibody or IL-32 binding fragment thereof is a human monoclonal antibody or IL-32 binding fragment thereof.

19. A vector comprising the cDNA molecule of claim 14.

20. The vector of claim 19, wherein the vector is an expression vector.

21. An isolated host cell comprising the vector of claim 20.

22. The host cell of claim 21, which is a prokaryotic or eukaryotic host cell.

23. A method of producing a monoclonal anti-IL-32 antibody or IL-32 binding fragment thereof, comprising:
(a) culturing in a cell culture the host cell of claim 22 under conditions allowing the expression of the antibody encoded by the cDNA molecule; and
(b) isolating the antibody from the cell culture.

24. A polynucleotide linked to a heterologous nucleic acid, wherein the polynucleotide is selected from the group consisting of:
(a) a polynucleotide encoding an immunoglobulin heavy chain or a fragment thereof comprising a heavy chain variable region (VH) comprising the complementarity determining regions (CDRs) of the VH variable region amino acid sequence depicted in SEQ ID NO: 2, wherein the immunoglobulin heavy chain VH when paired with a light chain variable region (VL) comprising the amino acid sequence depicted in SEQ ID NO: 4 binds to human IL-32gamma (IL-32γ) and neutralizes the biological activity of IL-32γ;
(b) a polynucleotide encoding an immunoglobulin light chain or a fragment thereof comprising a light chain variable region (VL) comprising the complementarity determining regions (CDRs) of the VL variable region amino acid sequence depicted in SEQ ID NO: 4, wherein the immunoglobulin light chain VL when paired with a heavy chain variable region (VH) comprising the amino acid sequence depicted in SEQ ID NO: 2 binds to recombinant human IL-32gamma (IL-32γ) and neutralizes the biological activity of IL-32γ;
(c) a polynucleotide encoding
(i) an immunoglobulin heavy chain or a fragment thereof comprising a heavy chain variable region (VH) comprising the complementarity determining regions (CDRs) of the VH variable region amino acid sequence depicted in SEQ ID NO: 2; and
(ii) an immunoglobulin light chain or a fragment thereof comprising a light chain variable region (VL) comprising the complementarity determining regions (CDRs) of the VL variable region amino acid sequence depicted in SEQ ID NO: 4;

(d) a polynucleotide encoding an immunoglobulin heavy chain or a fragment thereof comprising the amino acid sequence of SEQ ID NO: 2;
(e) a polynucleotide encoding an immunoglobulin light chain or a fragment thereof comprising the amino acid sequence of SEQ ID NO: 4; and
(f) a polynucleotide encoding an immunoglobulin heavy chain or a fragment thereof comprising the amino acid sequence of SEQ ID NO: 2 and an immunoglobulin light chain or a fragment thereof comprising the amino acid sequence of SEQ ID NO: 4.

25. The polynucleotide of claim 24, wherein the polynucleotide further encodes an amino acid sequence of a $C_H$ and/or $C_L$ constant region at least 95% identical to an amino acid sequence selected from SEQ ID NOs.: 6, 8, 14, 16, 22, 24 and 30.

26. The polynucleotide of claim 25, wherein the heterologous nucleic acid is a regulatory element.

27. The polynucleotide of claim 26, wherein the regulatory element is a promoter, an enhancer, a transcription termination sequence, or a leader sequence.

28. A vector comprising one or more of polynucleotides of claim 24.

29. The vector of claim 28, wherein the vector is an expression vector.

30. An isolated host cell comprising one or more vectors of claim 29.

31. The host cell of claim 30, which is a prokaryotic or eukaryotic host cell.

32. A method of producing a monoclonal antibody or an immunoglobulin chain thereof encoded by the polynucleotide in the vector in the host cell of claim 30, which comprises:
(a) culturing in a cell culture the host cell of claim 30 under conditions allowing the expression of the antibody or immunoglobulin chain; and
(b) isolating the antibody or immunoglobulin chain from the cell culture.

33. The method of claim 32, wherein the monoclonal antibody is a human antibody.

34. A method of treating an inflammatory or autoimmune disease or condition comprising administering to a subject in need of such treatment an effective amount of the human monoclonal anti-IL-32 antibody or IL-32 binding fragment thereof produced by the method of claim 23 or 32, wherein the inflammatory or autoimmune disease or condition is associated with the expression of IL-32, and is selected from the group consisting of inflammatory bowel disease (IBD; including Crohn's Disease, ulcerative colitis and Celiac's Disease), psoriasis, rheumatoid arthritis (RA), ankylosing spondylitis and other forms of spondyloarthritis, psoriatic arthritis, myasthenia gravis, chronic obstructive pulmonary disease (COPD), asthma, tuberculosis, cancer including leukemia, vascular inflammation and atherosclerosis.

35. A method of treating an inflammatory or autoimmune disease or condition comprising administering to a subject in need of such treatment an effective amount of a human monoclonal anti-IL-32 antibody or IL-32 binding fragment thereof encoded by the cDNA molecule of claim 14 or encoded by one or more of polynucleotides of claim 24, wherein the inflammatory or autoimmune disease or condition is associated with the expression of IL-32, and is selected from the group consisting of inflammatory bowel disease (IBD; including Crohn's Disease, ulcerative colitis and Celiac's Disease), psoriasis, rheumatoid arthritis (RA), ankylosing spondylitis and other forms of spondyloarthritis, psoriatic arthritis, myasthenia gravis, chronic obstructive pulmonary disease (COPD), asthma, tuberculosis, cancer including leukemia, vascular inflammation and atherosclerosis.

* * * * *